United States Patent [19]

Žmitek et al.

[11] Patent Number: 5,840,714
[45] Date of Patent: Nov. 24, 1998

[54] INCLUSION COMPLEXES OF RACEMIC IBUPROXAM AND OF OPTICALLY ACTIVE IBUPROXAM WITH CYCLODEXTRIN DERIVATIVES, PHARMACEUTICAL PREPARATIONS CONTAINING SAID INCLUSION COMPLEXES AND METHODS FOR USING SAME

[75] Inventors: Janko Žmitek; Katarina Verhnjak; Darja Ferčej-Temeljotov; Mateja Kovačič; Anton Lavrič; Breda Bole-Vunduk, all of Ljubljana, Slovenia

[73] Assignee: LEK, tovarna farmacevtskih in kemicnih izdelkov, d.d., Ljubljana, Slovenia

[21] Appl. No.: 602,729
[22] PCT Filed: Sep. 6, 1994
[86] PCT No.: PCT/SI94/00015
  § 371 Date: Feb. 20, 1996
  § 102(e) Date: Feb. 20, 1996
[87] PCT Pub. No.: WO95/07076
  PCT Pub. Date: Mar. 16, 1995

[30] Foreign Application Priority Data

Sep. 10, 1993 [SI] Slovenia .............................. P-9300470

[51] Int. Cl.⁶ .............................. A61K 47/40; C07H 21/00
[52] U.S. Cl. ........................... 514/58; 514/532; 514/777; 514/965; 536/46; 536/103
[58] Field of Search .............................. 514/58, 532, 777, 514/965; 536/46, 103

[56] References Cited

U.S. PATENT DOCUMENTS

| | | |
|---|---|---|
| 4,082,707 | 4/1978 | Orzalesi et al. |
| 4,727,064 | 2/1988 | Pitha |
| 4,869,904 | 9/1989 | Vekama et al. |
| 4,952,565 | 8/1990 | Žmitek et al. |
| 5,100,918 | 3/1992 | Sunshine et al. |
| 5,324,718 | 6/1994 | Loftsson |

FOREIGN PATENT DOCUMENTS

| | | |
|---|---|---|
| 0274444 | 7/1988 | European Pat. Off. |
| 9209308 | 6/1992 | WIPO |

*Primary Examiner*—James O. Wilson
*Attorney, Agent, or Firm*—Pollock, Vande Sande & Priddy

[57] ABSTRACT

Inclusion Complexes of Racemic Ibuproxam and of Optically Active Ibuproxam with Cyclodextrin Derivatives, Process for the Preparation Thereof, Pharmaceutical Preparations Containing these Inclusion Complexes or Containing Optically Active S-(+)-Ibuproxam, and Use Thereof There are disclosed novel inclusion complexes of racemic ibuproxam and of optically active S-(+)-ibuproxam with hydrophilic and hydrophobic cyclodextrin derivatives and, in the case of optically active S-(+)-ibuproxam, also with β-cyclodextrin alone. Further a process for preparing S-(+)-ibuproxam and inclusion complexes of racemic ibuproxam and of optically active S-(+)-ibuproxam with hydrophilic and hydrophobic derivatives of β-cyclodextrin and, in the case of optically active S-(+)-ibuproxam, also with β-cyclodextrin alone, is disclosed.

Disclosed are also pharmaceutical compositions containing these inclusion complexes or optically active S-(+)-ibuproxam.

Optically active S-(+)-ibuproxam and novel inclusion complexes of racemic ibuproxam and of optically active ibuproxam with cyclodextrin derivatives and, in the case of optically active S-(+)-ibuproxam, also with β-cyclodextrin alone, are better soluble in water and have improved biopharmaceutical properties such as lesser toxicity, better anti-inflammatory action and non-irritation of the gastric mucous membrane.

29 Claims, 51 Drawing Sheets

RACEMIC IBUPROXAM

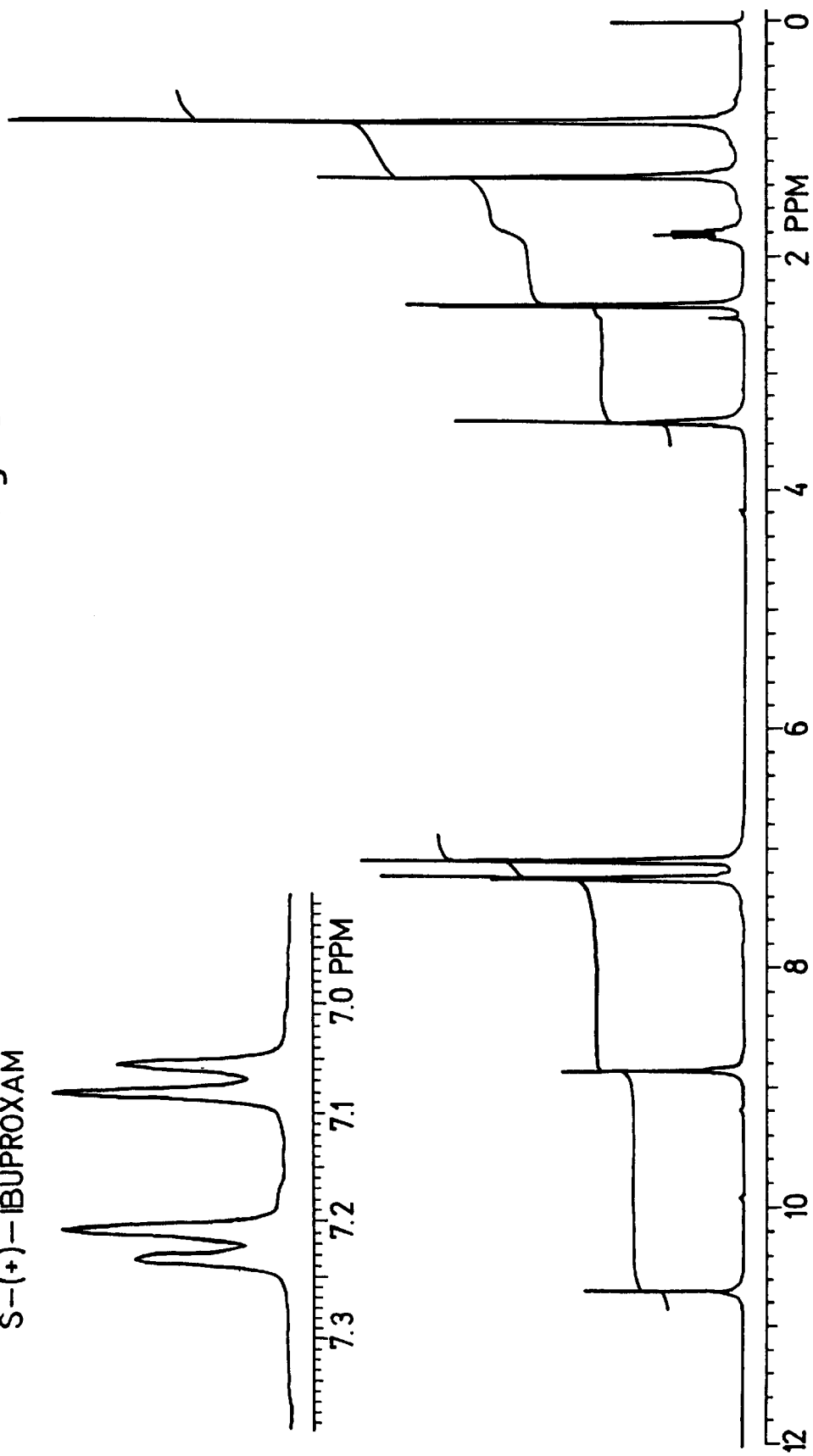

PHYSICAL MIXTURE

INCLUSION COMPLEX

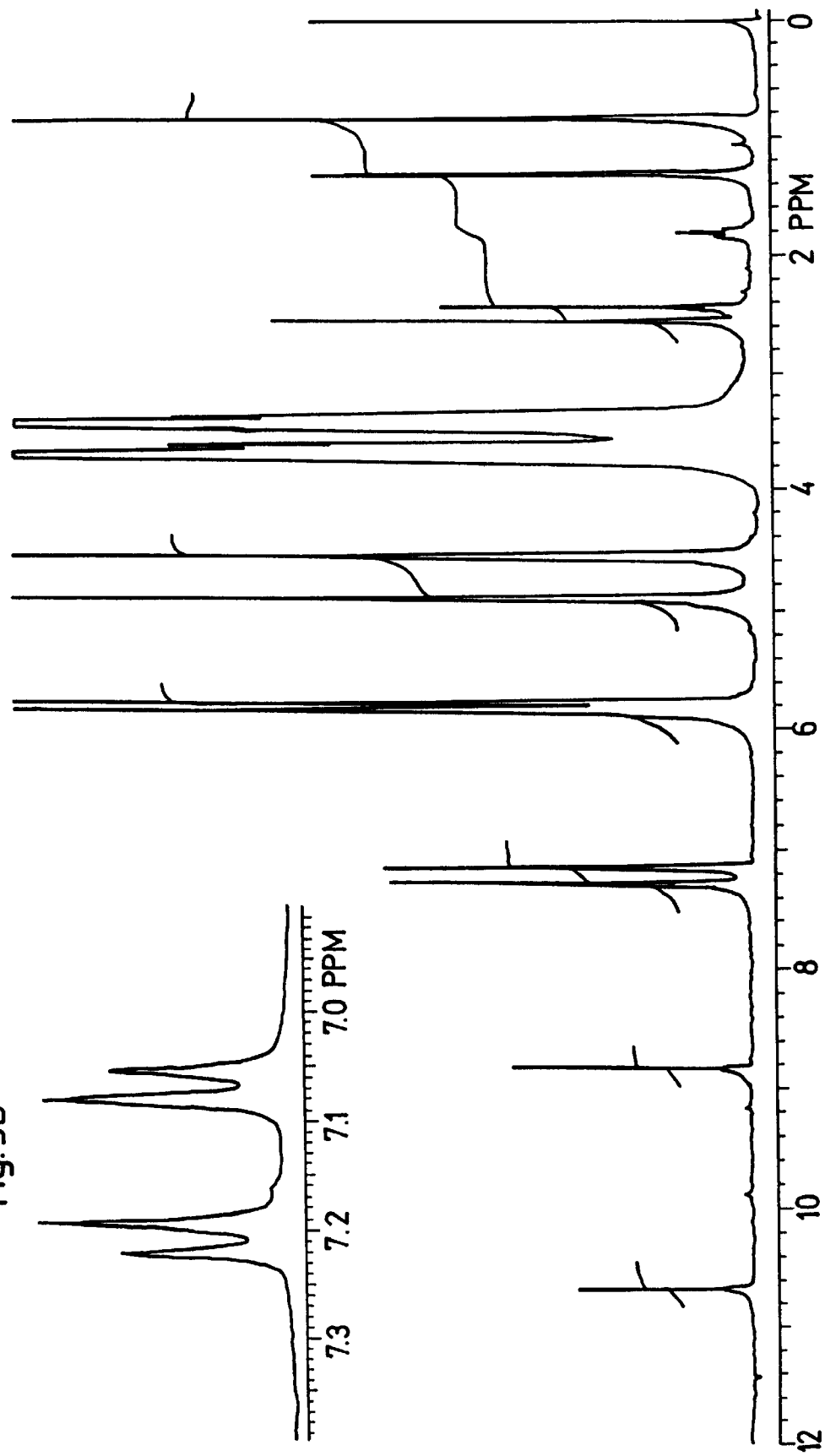

PHYSICAL MIXTURE

INCLUSION COMPLEX

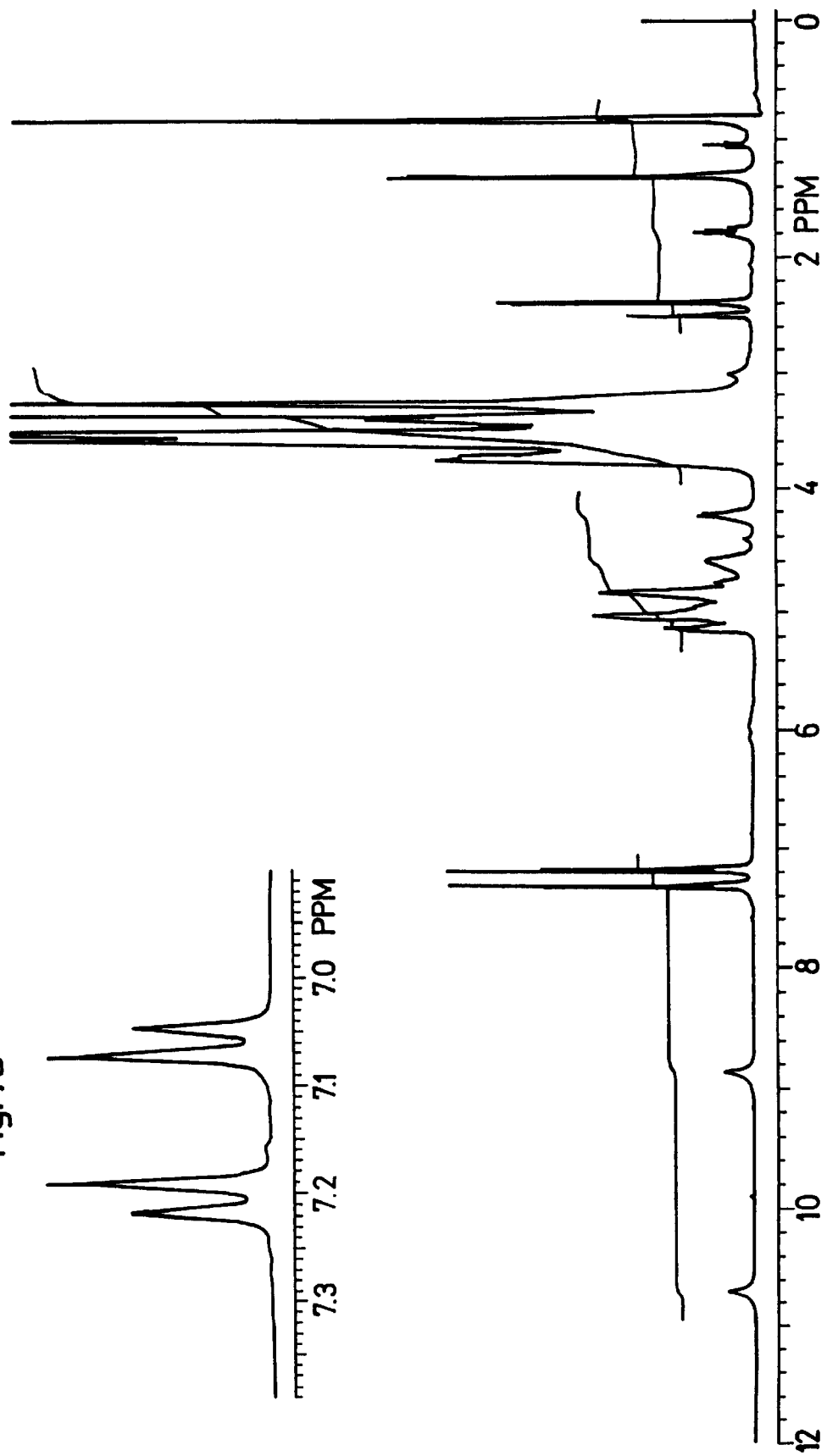

PHYSICAL MIXTURE

INCLUSION COMPLEX

PHYSICAL MIXTURE

INCLUSION COMPLEX

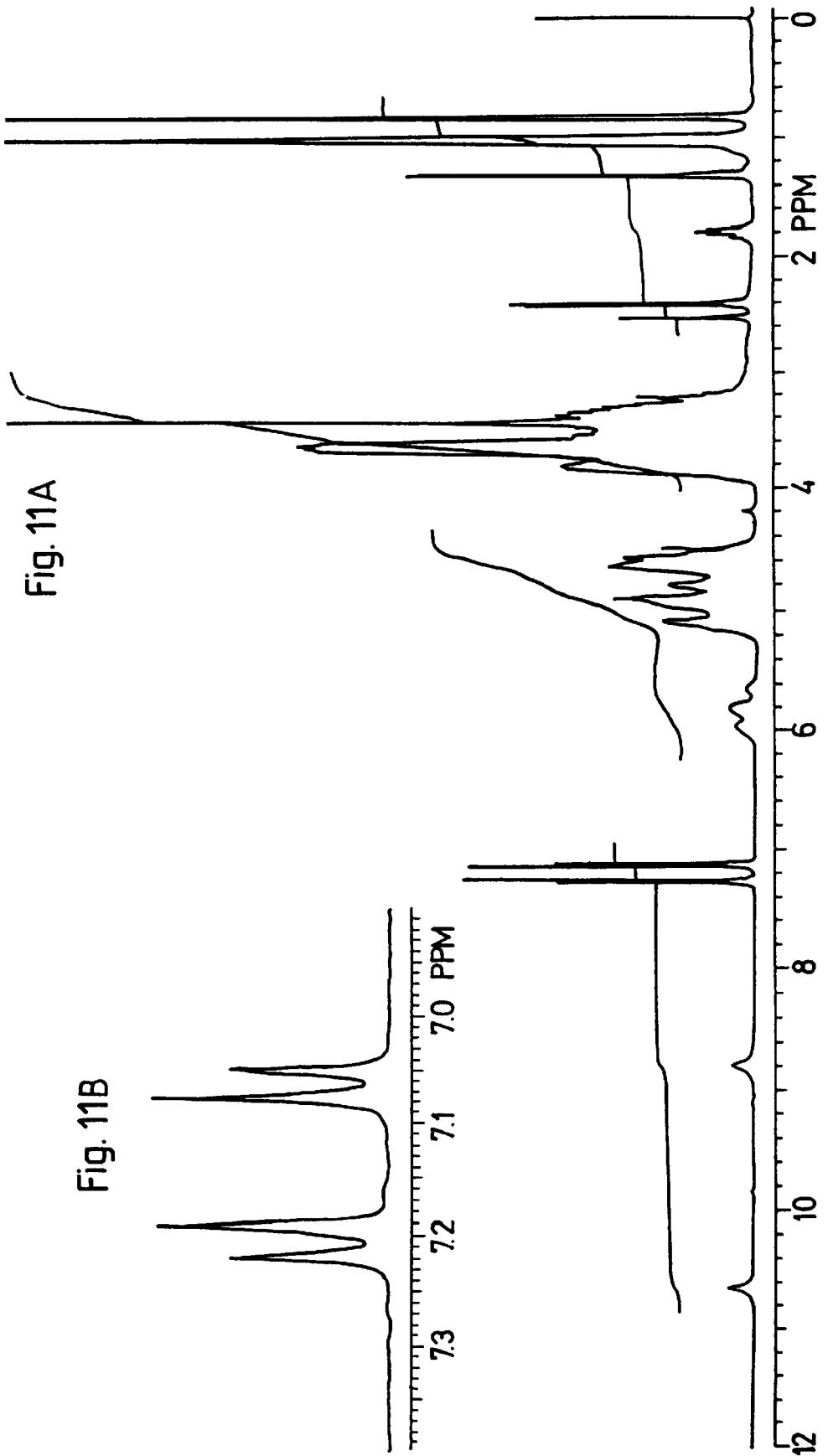

PHYSICAL MIXTURE

INCLUSION COMPLEX

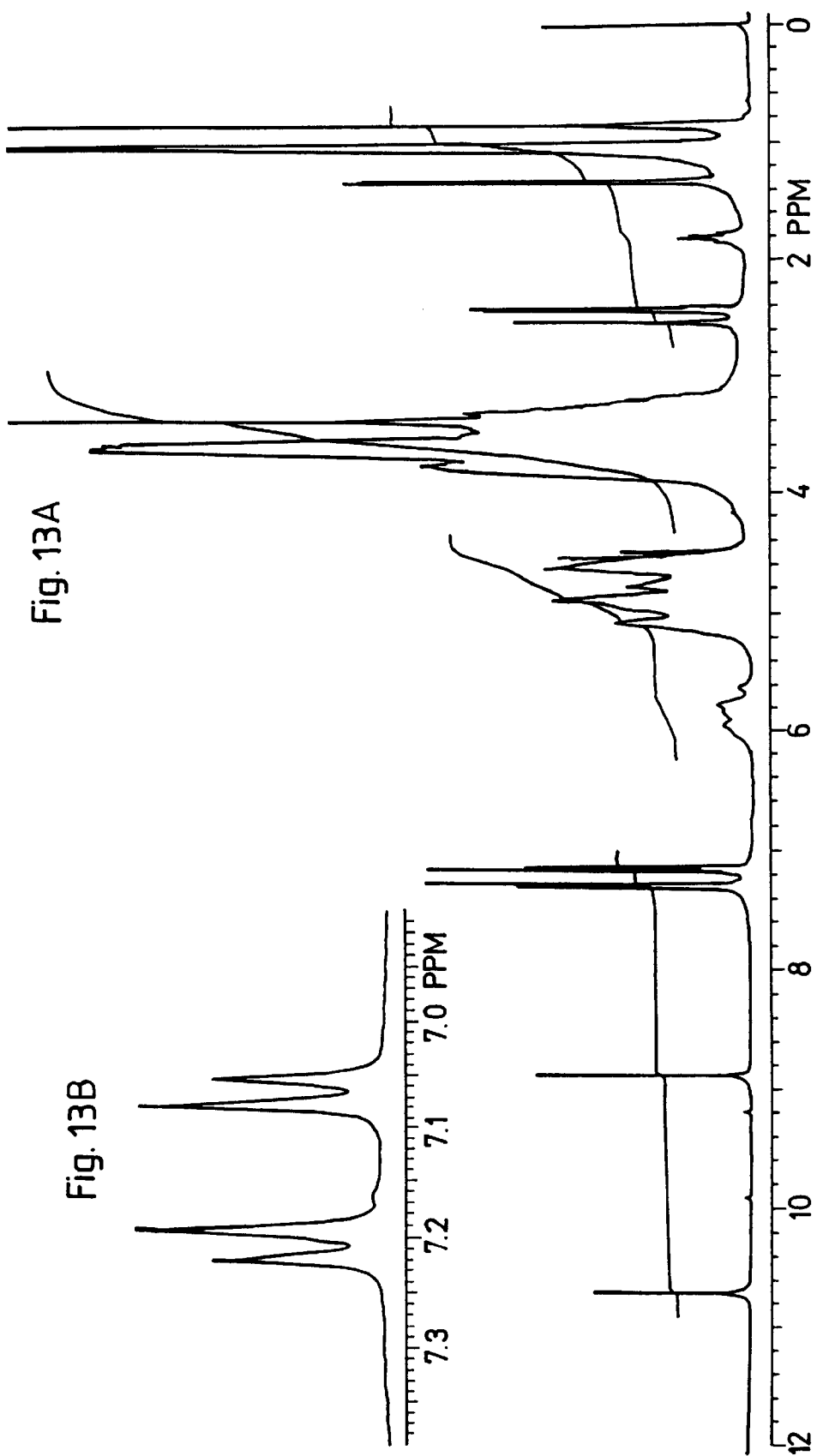

PHYSICAL MIXTURE

INCLUSION COMPLEX

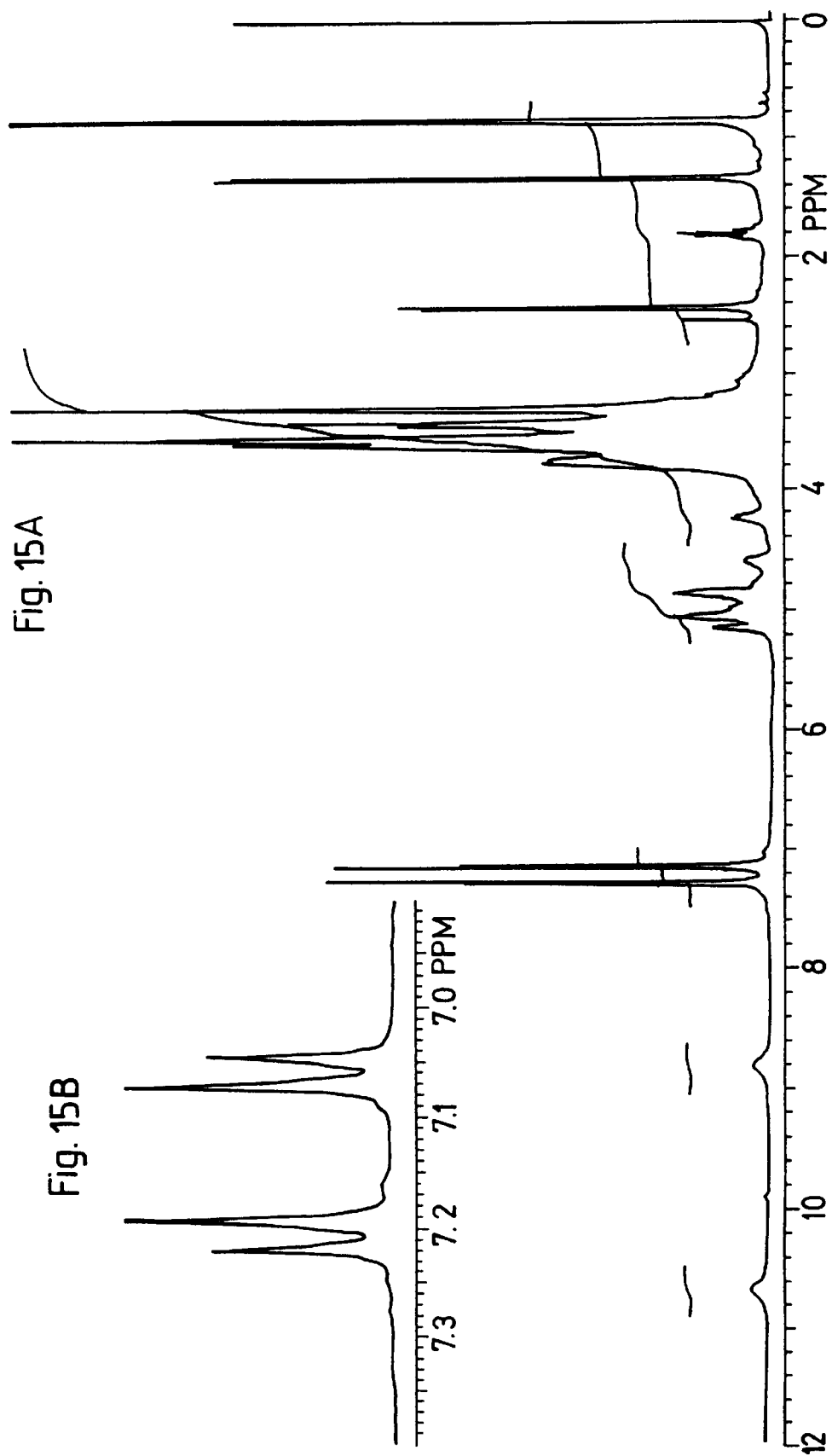

PHYSICAL MIXTURE

INCLUSION COMPLEX

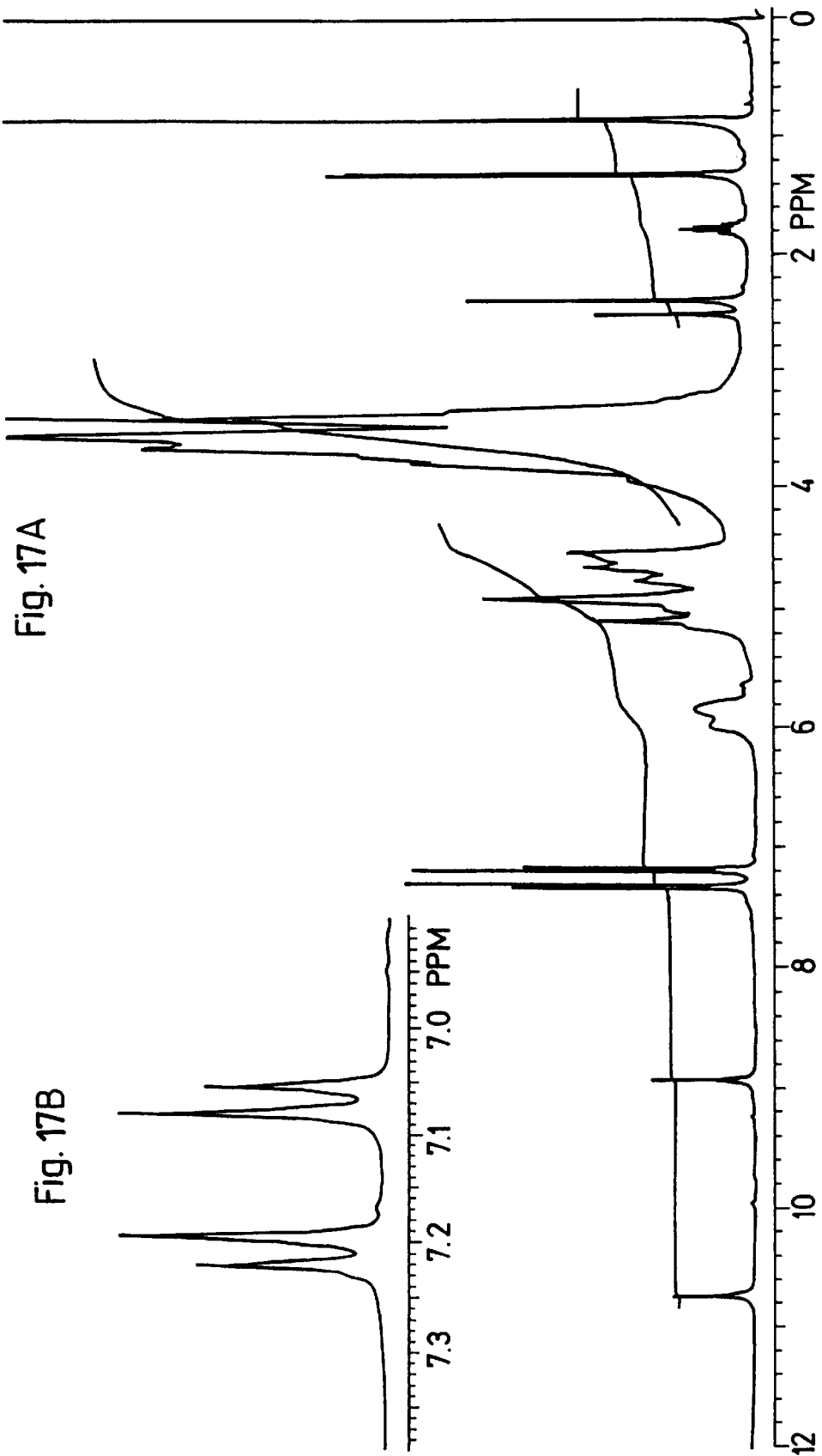

PHYSICAL MIXTURE

INCLUSION COMPLEX

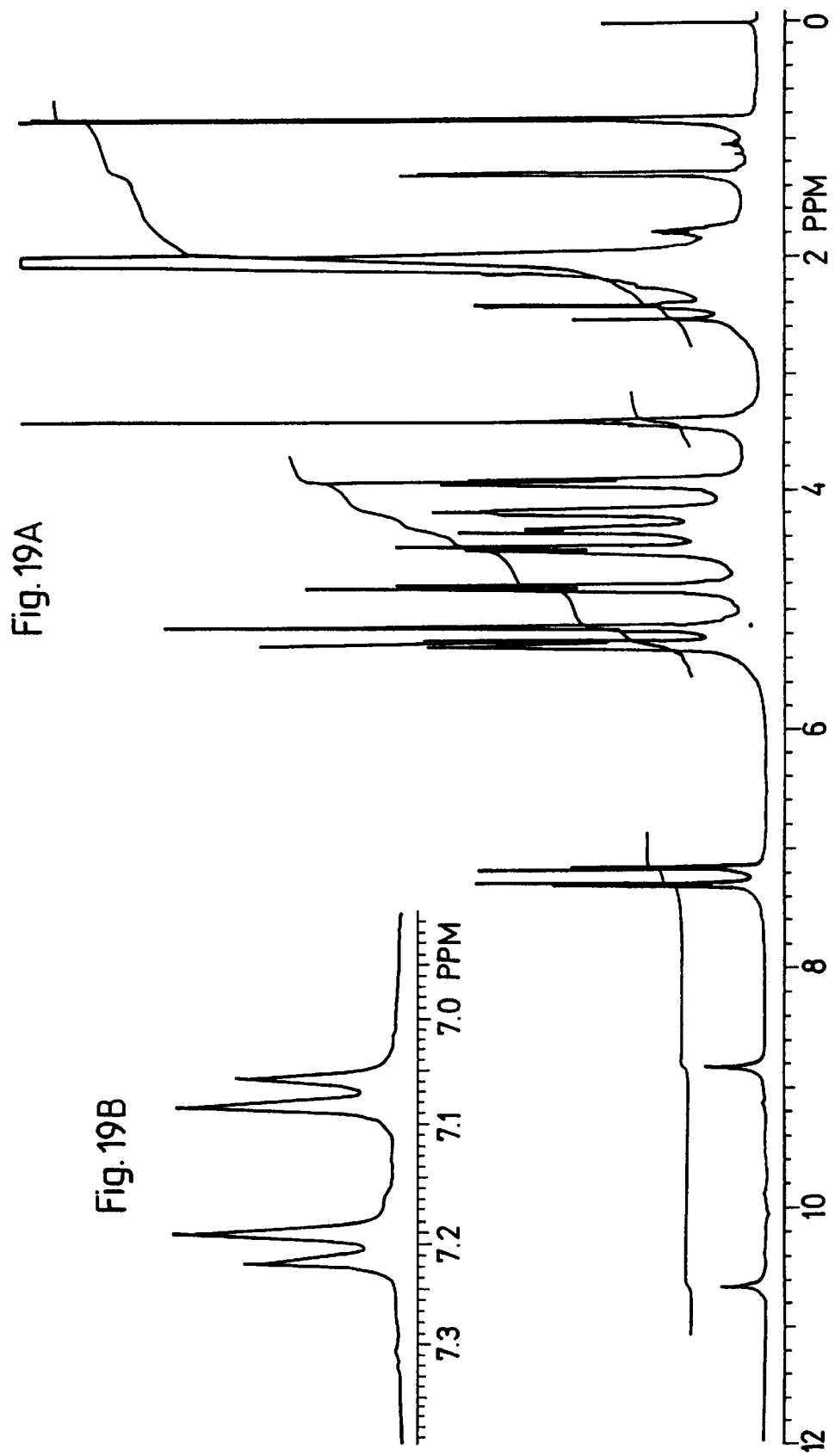

PHYSICAL MIXTURE

INCLUSION COMPLEX

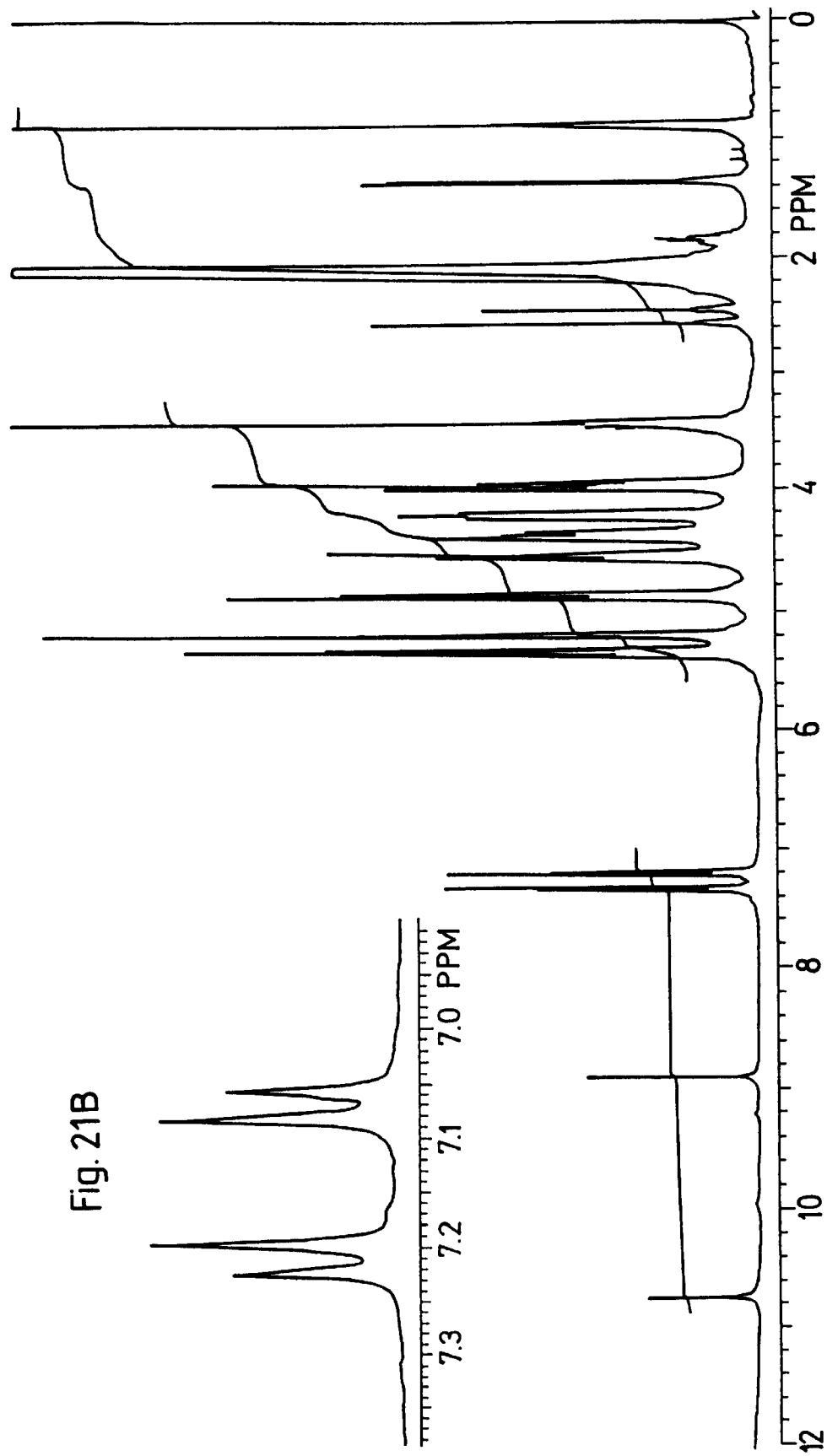

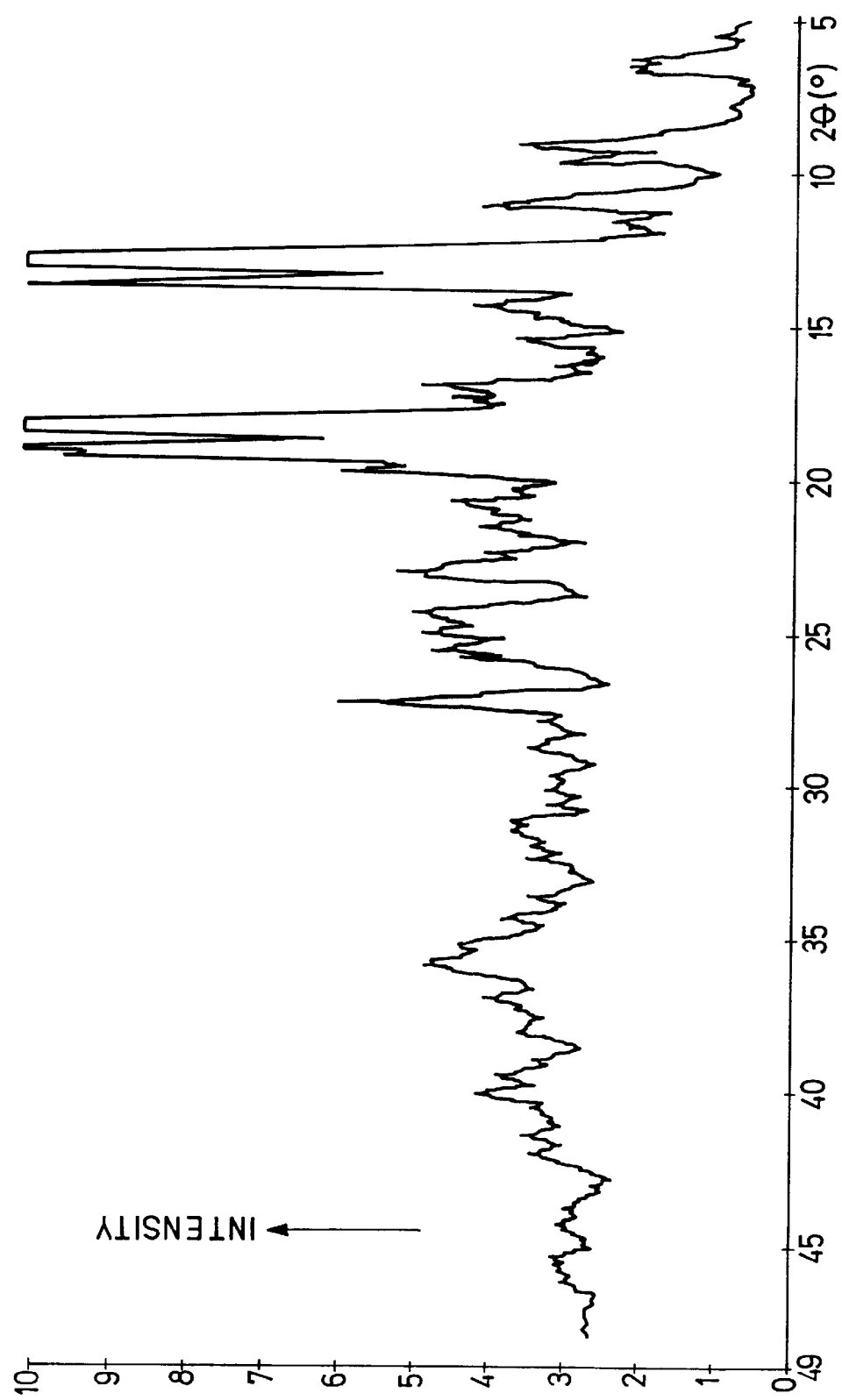

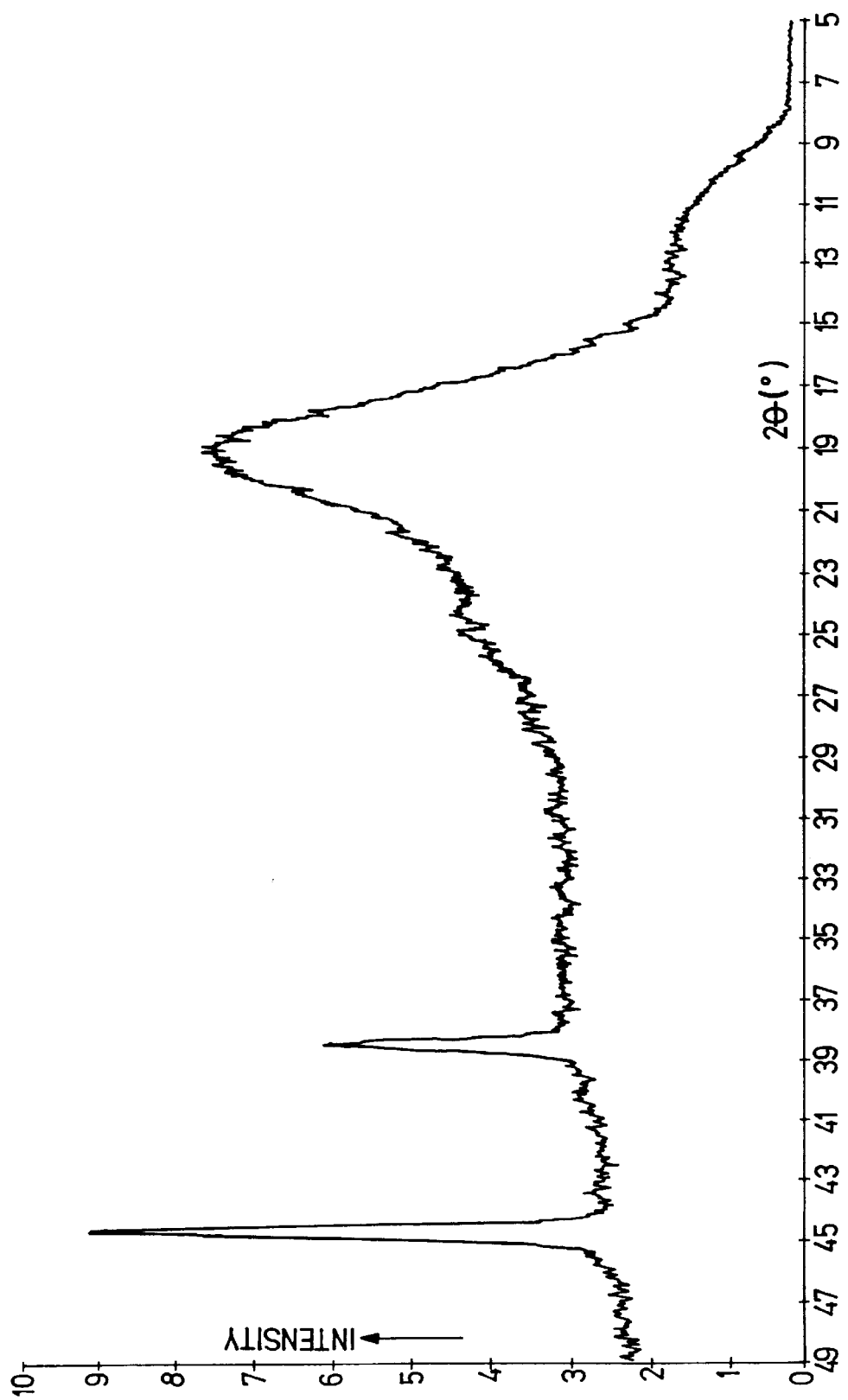

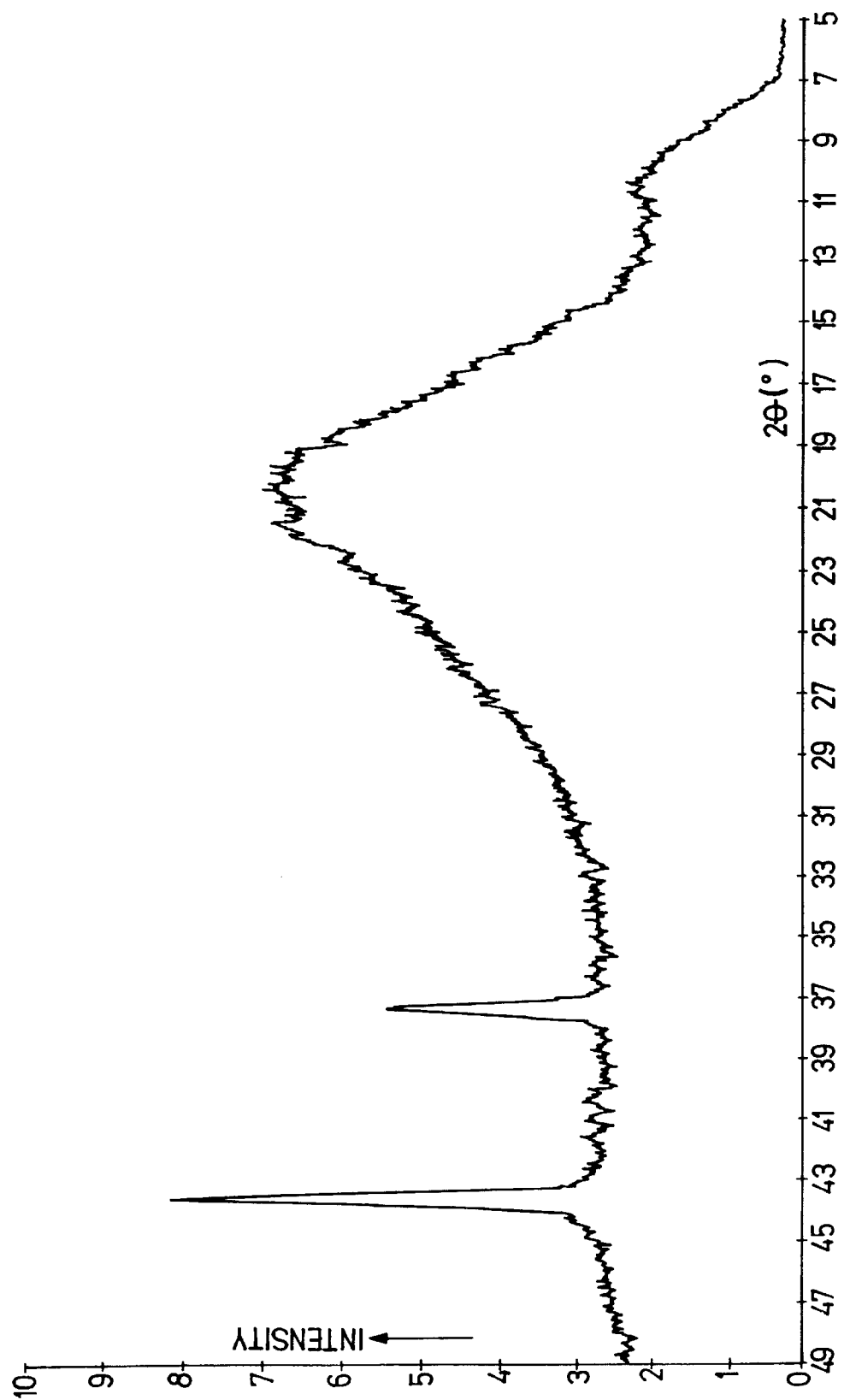

INCLUSION COMPLEXES OF RACEMIC IBUPROXAM AND OF OPTICALLY ACTIVE IBUPROXAM WITH CYCLODEXTRIN DERIVATIVES, PHARMACEUTICAL PREPARATIONS CONTAINING SAID INCLUSION COMPLEXES AND METHODS FOR USING SAME

TECHNICAL FIELD (IPC A 61K 31/185)

The present invention belongs to the field of pharmaceutical industry and relates to novel inclusion complexes of racemic ibuproxam and optically active S-(+)-ibuproxam with cyclodextrin derivatives such as methyl-β-cyclodextrin, dimethyl-β-cyclodextrin, hydroxypropyl-βcyclodextrin, hydroxyethyl-β-cyclodextrin, triacetyl-β-cyclodextrin and, in the case of optically active S-(+)-ibuproxam, also with β-cyclodextrin. The invention also relates to a process for the preparation thereof, to pharmaceutical compositions containing these inclusion complexes or optically active S-(+)-ibuproxam, and to the use thereof in the treatment of inflammations and febrile conditions as well as in alleviating pain.

TECHNICAL PROBLEM

There exists a constant need for preparing novel galenic forms of ibuproxam, racemic as well as optically active one, having improved biopharmaceutical properties such as low toxicity, better antiinflammatory action and non-irritation of gastric mucous membrane.

PRIOR ART

Ibuproxam is a generic name for 2-(4-isobutylphenyl)-propiohydroxamic acid of the formula

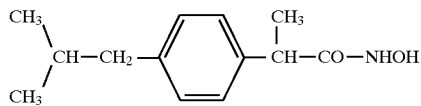

The substance was described for the first time in U.S. Pat. No. 4,082,707 as a solid crystalline substance in the form of white shining thin platelets having analgetic, antipyretic and antiinflammatory properties. The substance is soluble in methanol, ethanol, acetone and ethyl ether and is insoluble in water and petroleum ether.

The substance is ibuprofen (2-(4-isobutylphenyl)-propionic acid) prodrug. It has been experimentally confirmed that, irrespective of the ibuproxam application route, there occurs a rapid and almost complete metabolic conversion into ibuprofen. In the article by Orzalesi G. et al., Arzneim.-Forsch./Drug Res. 30 (II), the determination of ibuproxam and ibuprofen in blood is disclosed. The presence of ibuproxam and ibuprofen in blood was measured 15 minutes after application. The value of ibuprofen was 2.5 times higher than the value of ibuproxam, thus indicating a high rate of the conversion of ibuproxam into ibuprofen. In the article by Orzalesi G. et al., Arzneim.-Forsch./Drug Res. 27 (I) there are disclosed comparisons between the properties of ibuprofen and ibuproxam evidencing the same analgetic, antipyretic and antiinflammatory action of both substances. The introduction of hydroxylamine radical into the ibuprofen molecule increases the tolerance of the molecule, which is especially the result of different pharmakinetics of ibuproxam. The latter is less toxic for the mucous membrane of the alimentary tract with the result that the by-effects and toxicity of the active substance are essentially reduced. Simultaneously, the chemical conversion of ibuprofen into ibuproxam makes possible an increase of the transfer rate and an increase of ibuprofen concentration in blood in comparison with ibuprofen. The better bioavailability of ibuproxam in comparison with ibuprofen is the result of different physicochemical properties of either substance. In the same article a comparison between parenteral and peroral application of ibuprofen and ibuproxam is also disclosed. At parenteral application $LD_{50}$ is the same for both substances, whereas $LD_{50}$ at peroral application of ibuproxam is twice to three times greater than that of ibuprofen.

It is well-known that several biologically active substances exist in the form of a stereoisomeric mixture whereas usually only one isomer is biologically active. It has been proven that only S-(+)-enantiomer of ibuprofen is pharmacologically active. In the body of mammals (in liver and kidneys) R-(−)-enantiomer is to a varying extent converted by means of metabolic steroisomeric inversion into the active form of S-(+)-ibuprofen (Ching-Shih C. et al., Biochimica et Biophysica Acta, 1078 (1991)). According to data from the article by Geisslinger G. et al., Agents and Actions, Vol. 27, 3/4 (1989), in humans only R-(−)-enantiomer, yet only one third thereof, is converted to S-(+)-enantiomer.

In the literature there are disclosed several advantages of S-(+)-ibuprofen over racemic ibuprofen. From EP-B1-267 321 there are known sustained-release medicaments in the form of tablets or capsules containing ibuprofen only in the optically active form. In WO 89/00421 methods for increasing analgetic response in the organisms of mammals by means S-(+)-enantiomer of ibuprofen are disclosed. A pharmaceutical preparation for the treatment of fever and inflammations and for alleviating pain, said preparation containing S-(+)-ibuprofen sodium salt, is disclosed in WO 92/20334. In U.S. Pat. No. 5,100,918 a method for the treatment of sunburns with S-(+)-ibuprofen is disclosed.

Combinations of optically active ibuprofen with other optically active substances are disclosed as well. Thus in WO 92/05783 there is disclosed a combination with antihistaminics, in WO 92/17177 a combination with antitussives and expectorants and in WO 92/17171 a combination with sympathomimetics.

Ibuprofen as well as ibuproxam are very poorly soluble in water, which affects the rate and extent of absorption from the gastrointestinal tract and the bioavailability after peroral application.

Inclusion complexes with cyclodextrins are known from numerous literature sources such as J. Szejtli, Cyclodextrins and their Inclusion Complexes, Akademiai Kiado, Budapest, 1982, and J. Szejtly, Cyclodextrin Technology, Kluwer Academic Publishers, 1988. Cyclodextrins are cyclic compounds comprising 6, 7 or 8 glucopyranose units bound with α-1,4-glycosidic bonds. They are characterized by a cylindrical structure and special arrangement of hydroxylic groups, the outer surface of cyclodextrin ring being hydrophilic, which ensures water solubility, whereas its interior surface is lipophilic, which allows other molecules known as "guest molecules" or parts thereof that are less polar than water (hydrophobic molecules) and are of suitable dimensions, to be bound into the lipophilic cavity in the interior of the cylindrical cyclodextrin molecule and to form an inclusion complex.

An inclusion complex of S-(+)-ibuprofen with cyclodextrin and/or its derivatives, a process for the preparation thereof and its use in pharmaceutical formulations are disclosed in WO 92/09308. For ibuprofen bound into a complex with cyclodextrin, there are given better dissolution characteristics, a reduced offensive smell, taste and effect to the mucous membrane as well as better bioavailability.

The advantages of binding substances into inclusion complexes with cyclodextrin are also known in other active substances. Thus in U.S. Pat. No. 4,603,123 an inclusion complex of piroxicam with β-cyclodextrin and advantages thereof are disclosed: a four times greater solubility, increased therapeutic activity together with a lesser effect upon the gastric mucous membrane, a greater therapeutic index, the level of the active substance in plasma is higher and it appears soon after application. In U.S. Pat. No. 5,079,237 an inclusion complex of nicardipine or of its salt with β-cyclodextrin is disclosed. There are stated better characteristics of the rate and extent of dissolution and a twice better bioavailability whereas no difference in toxicity between nicardipine hydrochloride bound into a complex and free nicardipine hydrochloride can be noticed.

The inclusion complex of racemic ibuproxam with β-cyclodextrin is disclosed in U.S. Pat. No. 4,952,565, wherein essential physicochemical and pharmacokinetic properties of the complex of ibuproxam with β-cyclodextrin in comparison to non-complexed ibuproxam are stated: by binding ibuproxam into the cyclodextrin molecule the solubility in water is significantly increased, the inclusion complex is less toxic than ibuproxam alone, the complexing significantly increases the dissolution rate, the absorption constant of the complex is greater than the constant of the commercial preparation—tablets IBUDROS®, the relative bioavailability of the complex is 100% greater than that of the standard tablet preparation IBUDROS®, statistically significant differences are demonstrated with regard to the time periods necessary for the achievement of maximum concentrations and to average plasma concentrations, the same activity being achieved by half a dose of ibuproxam.

TECHNICAL SOLUTION

The problem to be solved by the present invention is to convert the racemic ibuproxam and optically active S-(+)-ibuproxam into a form better soluble in water, which would make possible the preparation of galenic forms having improved pharmacological properties. The object of the invention was especially to prepare inclusion complexes of β-cyclodextrin derivatives with optically active S-(+)-ibuproxam of high purity as well as to prepare S-(+)-ibuproxam, all of them having lower toxicity, better antiinflammatory action and better water solubility than the free racemic form of ibuproxam.

This object is achieved by binding racemic ibuproxam and optically active S-(+)-ibuproxam into the structure of derivatives of cyclodextrin molecules. Thus novel inclusion complexes in the form of a white powder are obtained.

The first object of the invention is thus an inclusion complex of racemic 2-(4-isobutylphenyl)-propiohydroxamic acid and of optically active S-(+)-2-(4isobutylphenyl)-propiohydroxamic acid (ibuproxam) of the formula

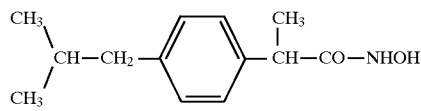

with cyclodextrin derivatives and, in the case of optically active S-(+)-2-(4-isobutylphenyl)-propiohydroxamic acid, also with β-cyclodextrin alone.

For the preparation of the inventive inclusion complexes α-cyclodextrin, β-cylodextrin and γ-cyclodextrin, preferably β-cyclodextrin, and their hydrophilic and hydrophobic derivatives may be used. As hydrophilic cyclodextrin derivatives all such known compounds may be used such as hexakis-(2,3,6tri-O -methyl)α-cyclodextrin dextrin (abbr. TRIMEA), heptakis-(2,6di-O -methyl)-β-cyclodextrin (abbr. DIMEB), monomethyl-β-cyclodextrin, methyl-β-cyclodextrin (abbr. RAMEB), heptakis-(2,3,6-tri-O-methyl) -β-cyclodextrin (abbr. TRIMEB), hydroxyethyl-β-cyclodextrin, hydroxypropyl-β-cyclodextrin, branched β-cyclodextrin derivatives such as glucosyl-β-cyclodextrin, dimaltosyl-β-cyclodextrin, diglucosyl-β-cyclodextrin, succinyl-β-cyclodextrin and others. As hydrophobic β-cyclodextrin derivatives all such known compounds may be used such as heptakis-(2,3,6-tri-O-acetyl)-β-cyclodextrin (abbr. triacetyl-β-CD), heptakis-(2,6-di-O-ethyl)-β-cyclodextrin (abbr. DE-β-CD), heptakis-(2,3-di-O-ethyl)-β-cyclodextrin, heptakis-(2,3,6-tri-O-ethyl)-β-cyclodextrin (abbr. TE-β-CD), O-carboxymethyl-O-ethyl-β-cyclodextrin, heptakis-2,6-di-O-pentyl-β-cyclodextrin, heptakis-2,3,6-tri-O-pentyl-β-cyclodextrin, heptakis-(3-O-acetyl-2,6-di-O-pentyl)-β-cyclodextrin and others.

Further, for the preparation of the inclusion complexes there can be used hydrophilic dihydroxyalkyl polymer derivatives of cyclodextrin, which are cyclodextrin polymers, or ionic cyclodextrin polymers such as aminoalkyl($C_1$–$C_3$)-, or dialkyl($C_1$–$C_3$)-aminoalkyl($C_1$–$C_3$) -substituted polymers.

Inclusion complexes of racemic ibuproxam and of optically active S-(+)-ibuproxam with β-cyclodextrin derivatives and, in the case of optically active S-(+)-ibuproxam, also with β-cyclodextrin alone are novel compounds hitherto not disclosed in the literature.

Optically active S-(+)-ibuproxam of high purity was prepared from commercial S-(+)-ibuprofen of 99.4% purity (Ethyl Corporation) in such a way that at first in methanol at the temperature of about 30° C. S-(+)-ibuprofen methyl ester was prepared, which was then converted with hydroxylamine hydrochloride at the temperature of about 0° C. into S-(+)-ibuproxam. The percentage of optical purity did not change during the reaction so that for preparing inclusion complexes with β-cyclodextrin and with derivatives thereof 99.4% S-(+)-ibuproxam was used.

The above process is also an object of the present invention.

Optically active S-(+)-ibuproxam of high purity could also be prepared from the commercial S-(+)-ibuprofen of 99.4% purity (Ethyl Corporation) in such a way that S-(+) -ibuprofen was converted in an organic solvent into S-(+)-ibuprofen anhydride (bis-[2-(4-isobutylphenyl)-propionic acid]-anhydride) at a temperature of about 30° C. according to the process disclosed in EP-A-0203379, which anhydride was then at the room temperature converted with hydroxylamine in an organic solvent such as e.g. dichloromethane, chloroform and acetonitrile, into S-(+)-ibuproxam. Also in this reaction the percentage of the optical purity did not change.

The above process is also an object of the present invention.

Inclusion complex of optically active S-( +)-ibuproxam with β-cyclodextrin was prepared in such a way that into a boiling β-cyclodextrin aqueous solution S-(+)-ibuproxam was added and after the completed reaction the undissolved ibuproxam was filtered off, the filtrate was cooled and the complex so formed was isolated. The reaction could also take place in an aqueous-methanolic medium instead in an aqueous medium, wherein β-cyclodextrin was dissolved in water at a temperature of about 70° C., methanolic solution of S-(+)-ibuproxam was added and after the completed reaction the solvent was evaporated and then the inclusion complex formed was isolated and dried in vacuo at the temperature of 40° C.

The above process is also an object of the present invention.

Inclusion complexes of racemic ibuproxam and optically active S-(+)-ibuproxam with hydrophilic derivatives of β-cyclodextrin were prepared in such a way that to an alcoholic solution such as e.g. methanolic solution of the hydrophilic derivative of β-cyclodextrin at room temperature, racemic ibuproxam or its S-(+)-enantiomer was added and after the completed reaction the obtained inclusion complex was isolated. The reaction could also take place in an aqueous medium, whereat the hydrophilic derivative of β-cyclodextrin was dissolved in water, the solution was heated to a temperature of about 70° C., racemic ibuproxam or its S-(+)-enantiomer was added and it was vigorously stirred. The obtained solution was frozen in liquid nitrogen and lyophilized.

The above process is also an object of the present invention.

The inclusion complexes of racemic ibuproxam and optically active S-(+)-ibuproxam with hydrophobic derivatives of β-cyclodextrin were prepared in such a way that a hydrophobic derivative of β-cyclodextrin was dissolved in an organic solvent and then racemic or optically active ibuproxam was added while stirring at room temperature. After the completed stirring the obtained clear solution was evaporated in vacuo at the temperature of 40° C. and the residue was isolated and dried in a vacuum drier at room temperature to the desired oily product. As the organic solvent acetone, ethyl acetate, dichloromethane, chloroform and other solvents could be used. Also a mixture of an organic solvent with water (e.g. acetone/water mixture) could be used. In this case a hydrophobic derivative of β-cyclodextrin was dissolved in the organic solvent at a temperature of about 40° C. and then there were added racemic or optically active ibuproxam and more water under vigorous stirring. The obtained solution was cooled to a temperature between 0° and 5° C. The formed precipitate was filtered off and dried in vacuo at the temperature of 40° C.

The above process is also an object of the present invention.

The yield in both cases, for inclusion complexes of β-cyclodextrin derivatives with racemic as well as with optically active ibuproxam, was high i.e. over 94%.

Inclusion complexes of racemic and optically active ibuproxam with β-cyclodextrin derivatives and, in the case of optically active S-(+)-ibuproxam, also with β-cyclodextrin alone could be formed in a ratio of 1:5 to 5:1, preferably in a ratio of 1:2 to 2:1.

The present invention also relates to pharmaceutical preparations containing a therapeutically active amount of inclusion complexes of racemic ibuproxam or optically active S-(+)-ibuproxam with cyclodextrin derivatives, in the case of optically active S-(+)-ibuproxam, also with β-cyclodextrin alone, together with a conventional pharmaceutically acceptable carrier and other adjuvants. To provide a systemic action of ibuproxam the following application routes are possible: peroral, rectal, transnasal, transbuccal, transdermal, and parenteral application, in an adequate pharmaceutical form such as tablets, capsules, drageés, and in forms such as sustained-release forms, effervescent forms, dispersion forms, gastroresistent forms, syrups, suspensions, solutions, suppositories, ointments, gels, emulsions, injections, infusions etc. Tablets may also be lacquered, whereat the usual process for applying a lacquer coating onto the tablet surface by means of the spraying method is used. To provide a topical action of ibuproxam the following application routes are possible: dermal, occular, vaginal application, in an adequate pharmaceutical form such as cremes, ointments, gels, solutions and suspensions, eye ointments, eye drops, vagitories etc. In addition to the active substance, these preparations also contain pharmaceutically acceptable adjuvants in their optimum concentrations such as carriers, stabilizers, preservatives, colourants etc. The preparations are prepared according to known methods specific for a certain pharmaceutical form.

The present invention further relates to pharmaceutical preparations containing a therapeutically active amount of the optically active S-(+)-ibuproxam together with a conventional pharmaceutically acceptable carrier and other adjuvants.

The present invention also relates to the use of optically active S-(+)-ibuproxam and novel inclusion complexes of racemic ibuproxam and of optically active S-(+)-ibuproxam with cyclodextrin derivatives and, in the case of optically active S-(+)-ibuproxam, with β-cyclodextrin alone as a medicine as well as to their use in the treatment of inflammations and febrile conditions and for alleviating pain.

SUMMARY OF THE DRAWINGS

FIG. 2A-1 shows NMR spectrum of racemic ibuproxam.

FIG. 2A-2 shows NMR spectrum of racemic ibuproxam.

FIG. 2B-1 shows NMR spectrum of S-(+)-ibuproxam.

FIG. 2B-2 shows NMR spectrum of S-(+)-ibuproxam.

FIG. 5 shows NMR spectrum of the complex of S-(+)-ibuproxam with β-cyclodextrin.

FIG. 7 shows NMR spectrum of the complex of racemic ibuproxam with methyl-β-cyclodextrin.

FIG. 11 shows NMR spectrum of the complex of racemic ibuproxam with hydroxypropyl-β-cyclodextrin.

FIG. 13 shows NMR spectrum of the complex of S-(+)-ibuproxam with hydroxypropyl-β-cyclodextrin.

FIG. 15 shows NMR spectrum of the complex of racemic ibuproxam with hydroxyethyl-β-cyclodextrin.

FIG. 17 shows NMR spectrum of the complex of S-(+)-ibuproxam with hydroxyethyl-β-cyclodextrin.

FIG. 19 shows NMR spectrum of the complex of racemic ibuproxam with triacetyl-β-cyclodextrin.

FIG. 21 shows NMR spectrum of the complex of S-(+)-ibuproxam with triacetyl-β-cyclodextrin.

FIGS. 22A to 22D show the comparison of recordings of x-ray powder diffraction for β-cyclodextrin (FIG. 22A), S-(+)-ibuproxam (FIG. 22B), physical mixture of S-(+)-ibuproxam and β-cyclodextrin (FIG. 22C) and inclusion complex of S-(+)-ibuproxam with β-cyclodextrin (FIG. 22D).

FIGS. 25A to 25D show the comparison of recordings of x-ray powder diffraction for hydroxypropyl-β-cyclodextrin (FIG. 25A), racemic ibuproxam (FIG. 25B), physical mixture of racemic ibuproxam and hydroxypropyl-β-cyclodextrin (FIG. 25C) and inclusion complex of racemic ibuproxam with hydroxypropyl-β-cyclodextrin (FIG. 25D).

FIGS. 26A to 26D show the comparison of recordings of x-ray powder diffraction for triacetyl-β-cyclodextrin (FIG. 26A), racemic ibuproxam (FIG. 26B), physical mixture of racemic ibuproxam and triacetyl-β-cyclodextrin (FIG. 26C) and inclusion complex of racemic ibuproxam with triacetyl-β-cyclodextrin (FIG. 26D).

Figure 1A:
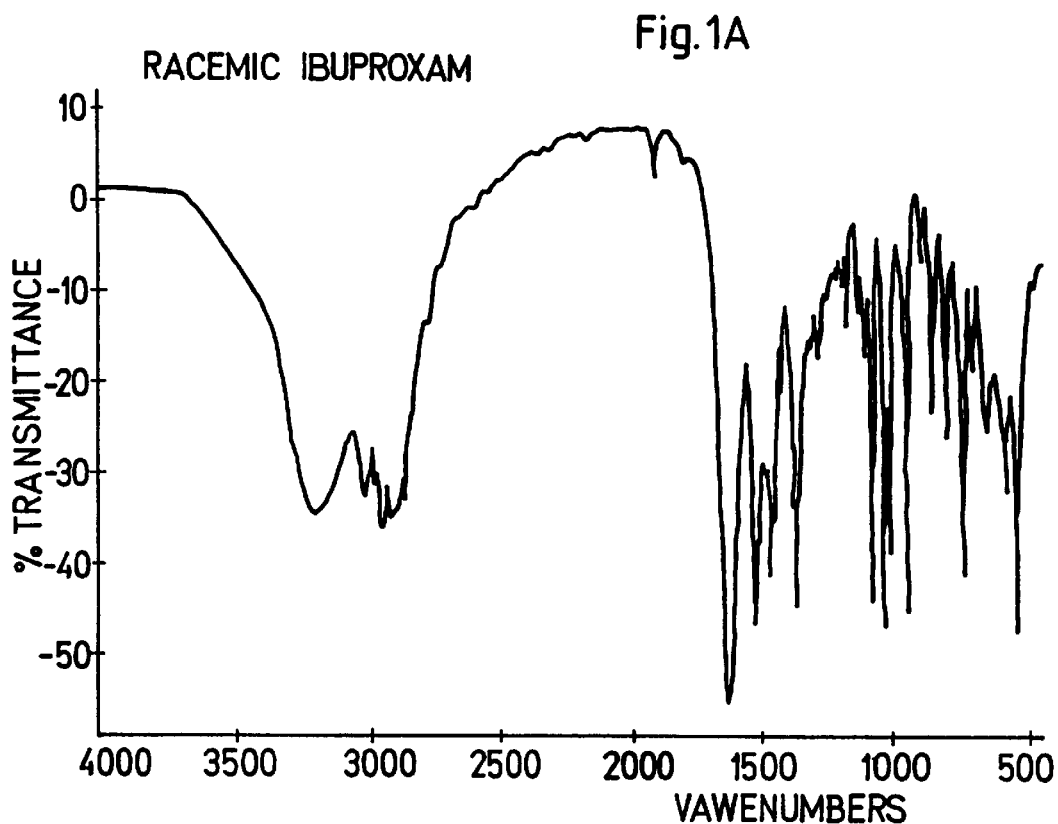
FIG. 1A shows IR spectrum of racemic ibuproxam.
Figure 1B:
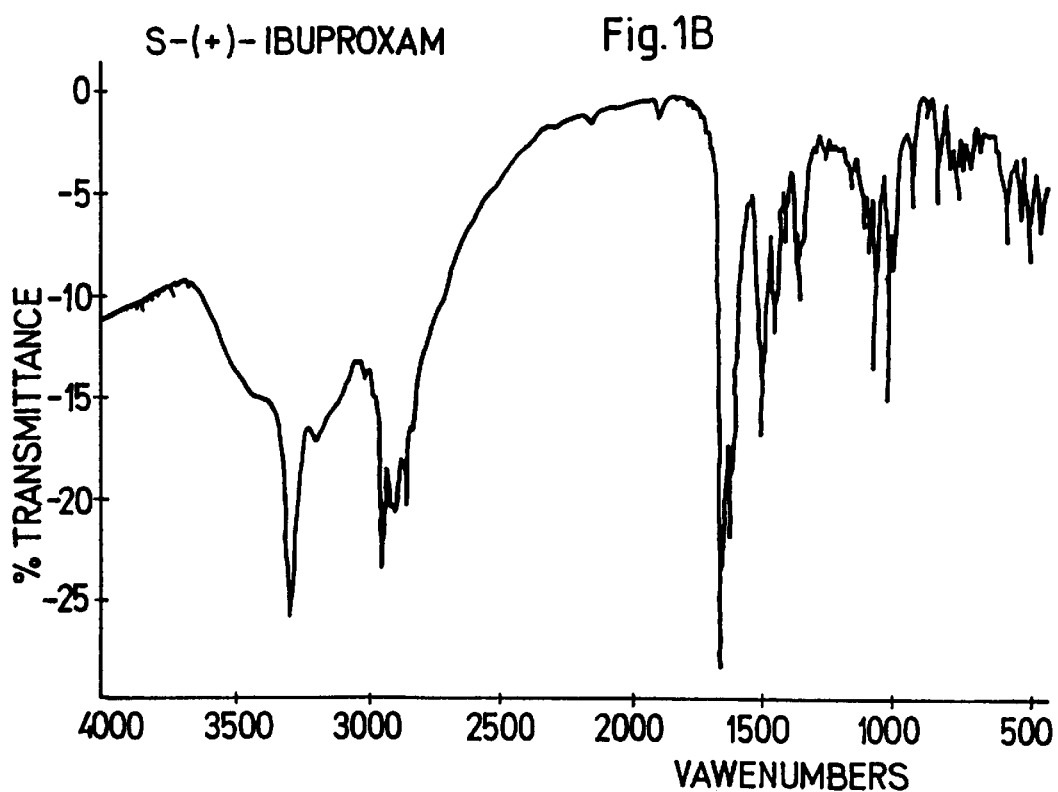
FIG. 1B shows IR spectrum of S-(+)-ibuproxam.

The invention is illustrated by the following Examples which in no way represent a limitation thereof.

EXAMPLE 1

Preparation of S-(+)-ibuproxam

Optically active S-(+)-ibuproxam may be prepared in two ways a) S-(+)-ibuprofen (5.0 g; 0.024 mole) was shed into methanol (35 ml), concentrated sulfuric acid (1 ml) was added and the reaction mixture was heated for 3 hours at the reflux temperature of the reaction mixture. Then it was evaporated in vacuo at the temperature of 30° C. to dryness. S-(+)-ibuprofen methyl ester (5.1 g) was obtained.

Hydroxylamine hydrochloride (1.7 g; 0.024 mole) was poured over with methanol (38 ml) and cooled to the temperature of 0° C. A methanolic solution (13 ml) of sodium hydroxide (4.7 g of NaOH/13 ml of methanol) and S-(+)-ibuprofen methylester (5.1 g) were slowly added and it was stirred for 4 hours at the temperature of 20° C. The reaction mixture was evaporated in vacuo at the temperature of 30° C. to dryness. Then demineralized water (70 ml) was added. The reaction mixture was neutralized with a hydrochloric acid aqueous solution (20%) up to the pH value of 6. The product was filtered off and the filtrate was dried in vacuo at a temperature up to 30° C. The product was crystallized first from a methanol/water mixture and then from a petroleum ether/acetone mixture. There was obtained S-(+)-ibuproxam (4.5 g) in the form of a white powder, m.p. 119° to 121° C.

b) S-(+)-ibuprofen (2.3 g; 0.011 mole) was dissolved in dichlorometane (15 ml) and then N,N'-dicyclohexylcarbodiimide (DCC) (1.15 g) was added. The reaction mixture was stirred for 1 hour at the temperature of 30° C., then filtered and the filtrate was evaporated in vacuo. S-(+)-ibuprofen anhydride (2.19 g; 100%) was obtained in the form of an oily product.

S-(+)-ibuprofen anhydride (2 g; 0.005 mole) was dissolved in dichloromethane (10 ml) and hydroxylamine (0.18 g; 0.0055 mole) was added. The reaction mixture was stirred for 1 hour at room temperature, then the solvent was evaporated in vacuo, the residue was poured over with petroleum ether (15 ml) and stirred for two hours. The obtained product was filtered off and washed with petroleum ether. S-(+)-ibuproxam (1.13 g; 92%) was obtained in the form of a white powder, m.p. 119° to 121° C.

Specific rotation:

$[\alpha]^{23}_{Na}$ (ethanol abs., 0.30)=+44.4°

IR and NMR spectra of S-(+)-ibuproxam corresponded to the spectra of racemic ibuproxam.

Figures 1, 2, 2A:
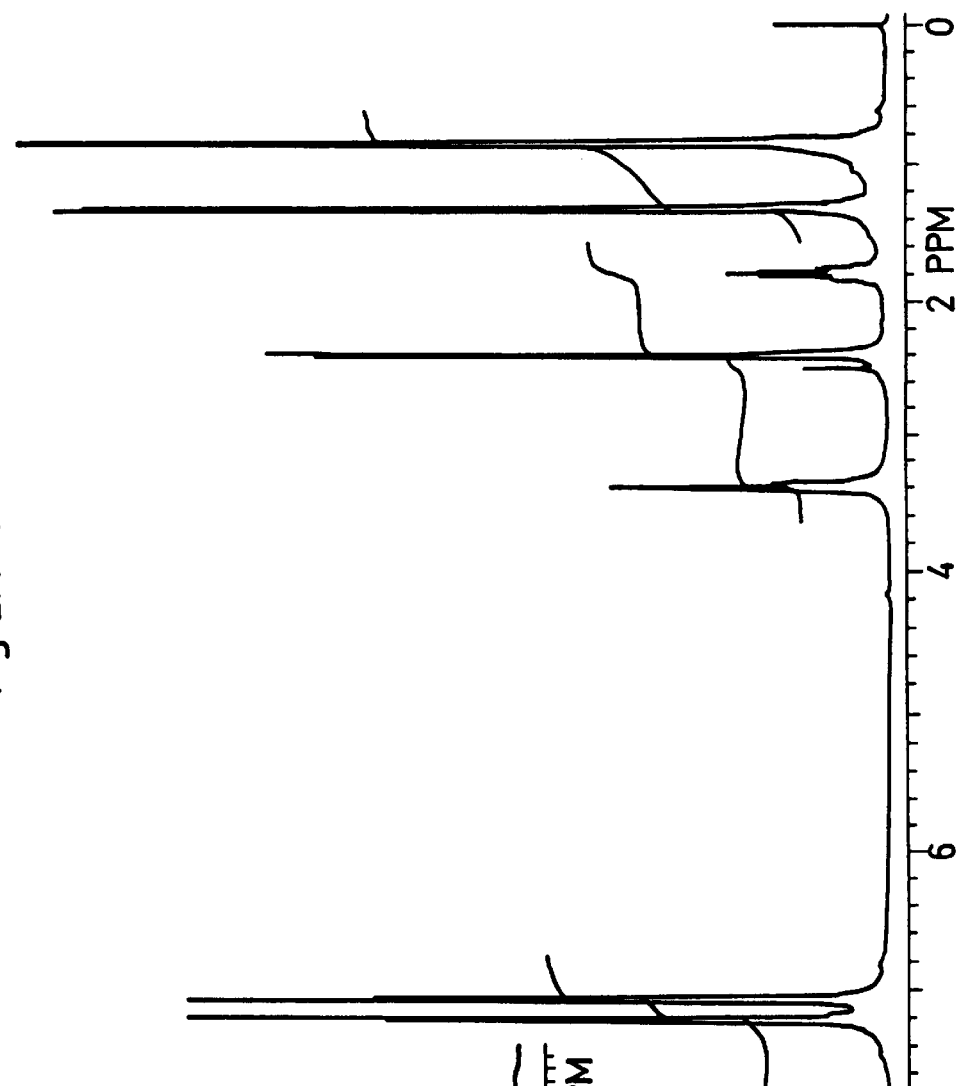

FIG. 1 shows IR spectrum of racemic ibuproxam and S-(+)-ibuproxam.

FIGS. 2A and 2B show NMR spectrum of racemic ibuproxam and S-(+)-ibuproxam.

Figure 3A:
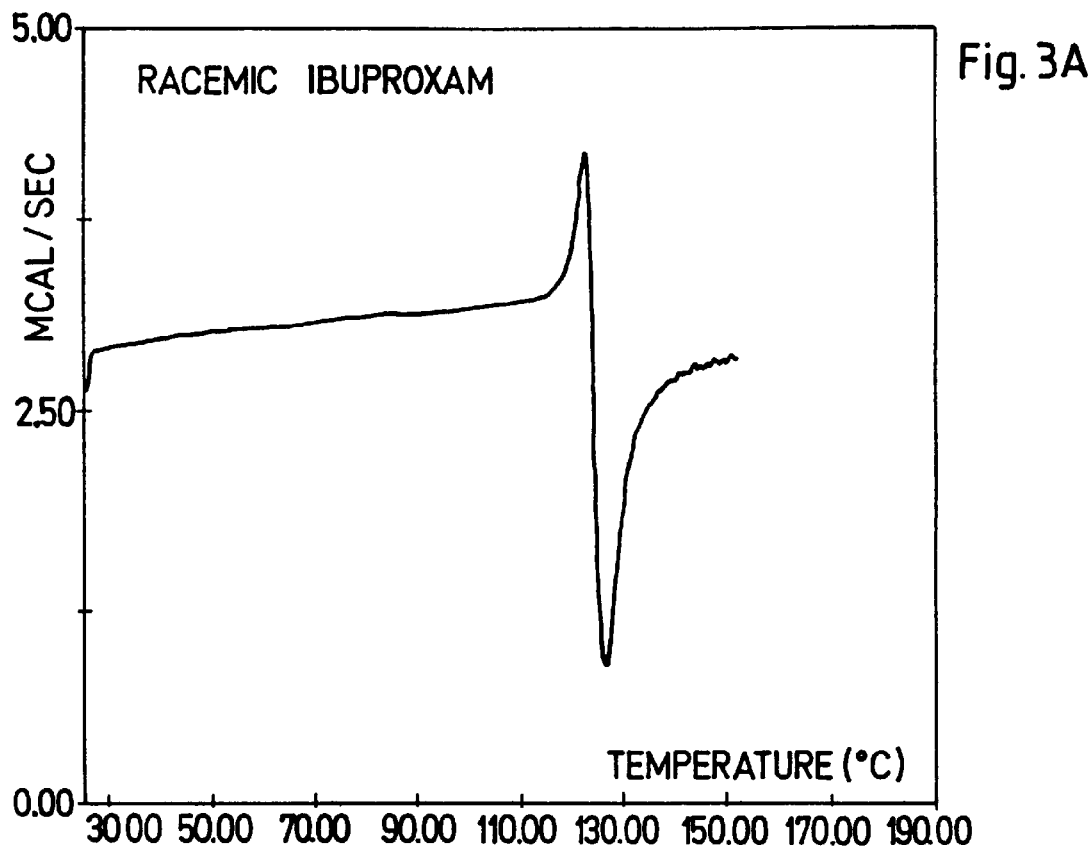
FIG. 3A shows DSC (differential scanning calorimetry) thermogram of racemic ibuproxam.
Figure 3B:
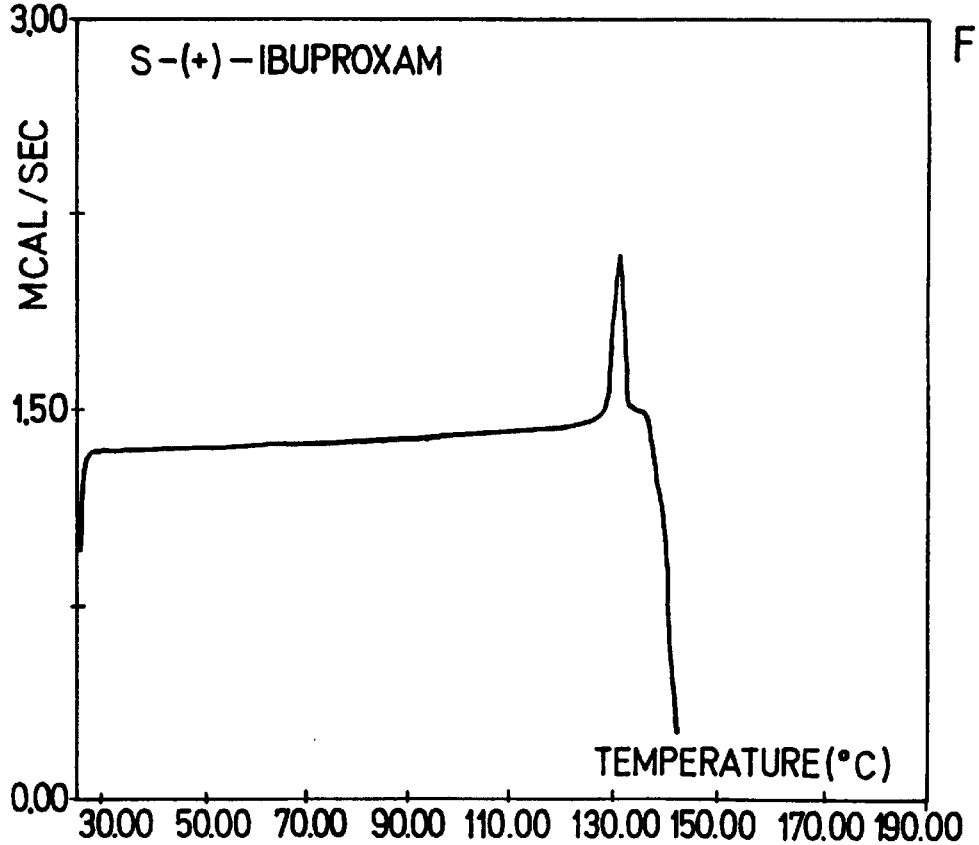
FIG. 3B shows DSC thermogram of S-(+)-ibuproxam.

FIG. 3 shows DSC (differential scanning calorimetry) thermogram of racemic ibuproxam and S-(+)-ibuproxam.

EXAMPLE 2

Preparation of inclusion complex of optically active S-(+)-ibuproxam with β-cyclodextrin a) Procedure in aqueous medium β-cyclodextrin (1.135 g; 1.0 mmole) in water (10 ml) was heated to boiling temperature. Into the boiling solution S-(+)-ibuproxam (0.221 g; 1.0 mmole) was added and it was vigorously stirred for 2 minutes. Undissolved S-(+)-ibuproxam was filtered off and the filtrate was cooled during stirring to a temperature between 0 ° and 5° C. The obtained complex was filtered off by suction and dried in vacuo at the temperature of about 40° C. Inclusion complex (1.28 g; 94.4%) of S-(+)-ibuproxam with β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}{}_{Na}$ of the complex formed are summarized in Table 2.

Differential scanning calorimetry (DSC thermogram)

Figure 4A:
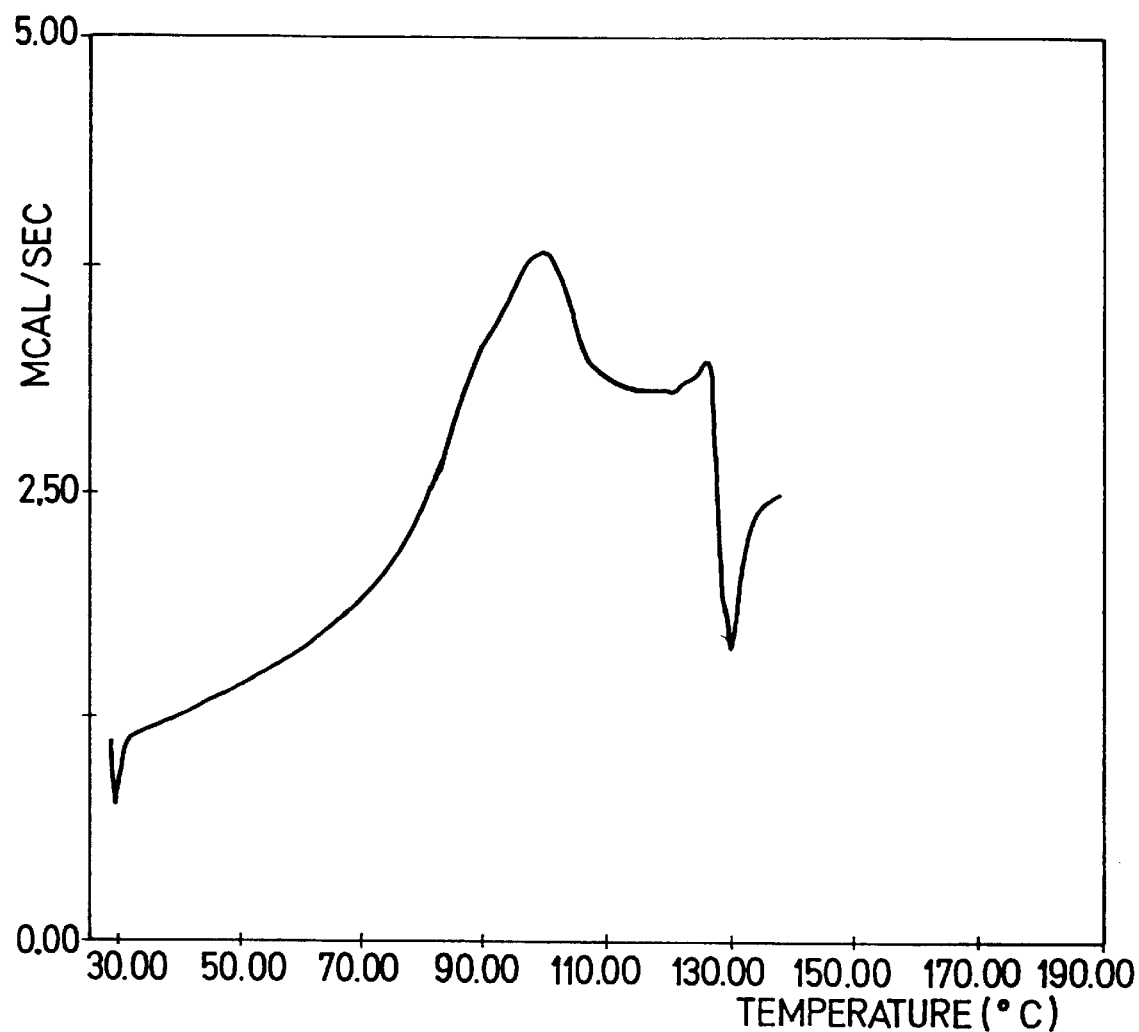
FIG. 4A shows DSC thermogram of mixture of S-(+)-ibuproxam with β-cyclodextrin.
Figure 4B:
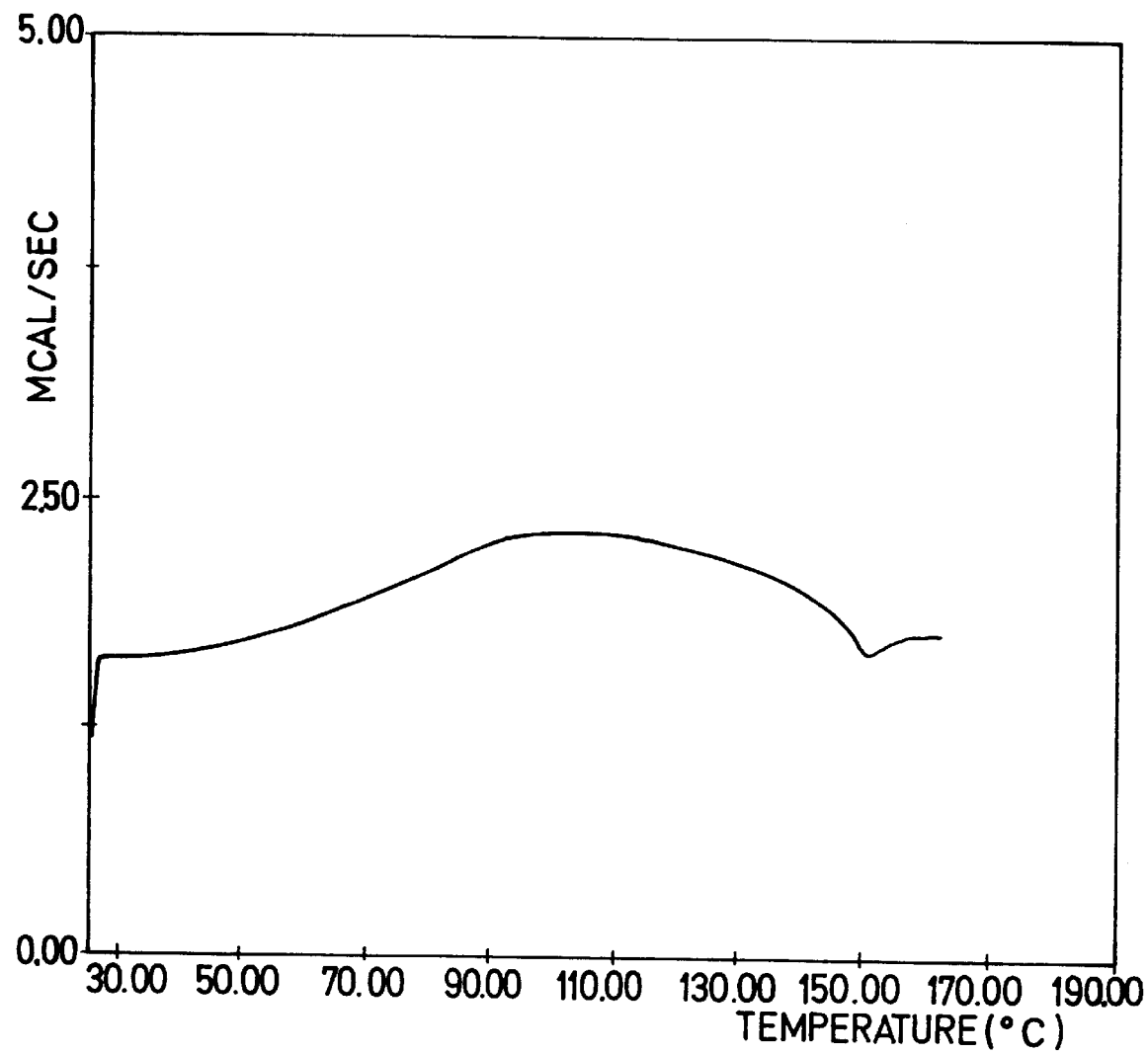
FIG. 4B shows DSC thermogram of inclusion complex of S-(+)-ibuproxam with β-cyclodextrin.

In the curve of the obtained product there was not detected any endothermic transition for a melting point, characteristic of a physical mixture of ibuproxam/β-cyclodextrin at a temperature from 120° to 130° C. (FIGS. 4A and 4B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

FIG. 5 shows NMR spectrum of the complex of S-(+)-ibuproxam with β-cyclodextrin.

b) Procedure in a solvent mixture (methanol/water in the ratio 5:20)

β-cyclodextrin (1.135 g; 1.0 mmole) was dissolved in water (20 ml) at a temperature of about 70° C. During stirring a solution of S-(+)-ibuproxam (0.221 g; 1.0 mmole) in methanol (5 ml) was added. At the temperature of 70° C. it was stirred for another 5 minutes, when the solvents were evaporated. The obtained complex was dried in vacuo at a temperature about 40° C. Inclusion complex (1.26 g; 92.9%) of S-(+)-ibuproxam with β-cyclodextrin was obtained in the form of a white powder in the molar ratio of 1:1.

Differential scanning calorimetry and NMR spectrum showed the same results as in the process for preparing the inclusion complex in an aqueous medium.

EXAMPLE 3

Preparation of inclusion complex of racemic ibuproxam with methyl-β-cyclodextrin a) Procedure in methanolic medium Racemic ibuproxam (0.221 g; 1.0 mmole) was added to a solution of methyl-β-cyclodextrin (1.31 g; 1.0 mmole) in methanol (10 ml). The obtained solution was stirred for another 5 minutes at room temperature. Methanol was then evaporated and the obtained complex was dried in vacuo at the temperature of 40° C. Inclusion complex (1.51 g; 98.6%) of racemic ibuproxam with methyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}{}_{Na}$ of the complex formed are summarized in Table 1.

Differential scanning calorimetry (DSC thermogram)

Figure 6A:
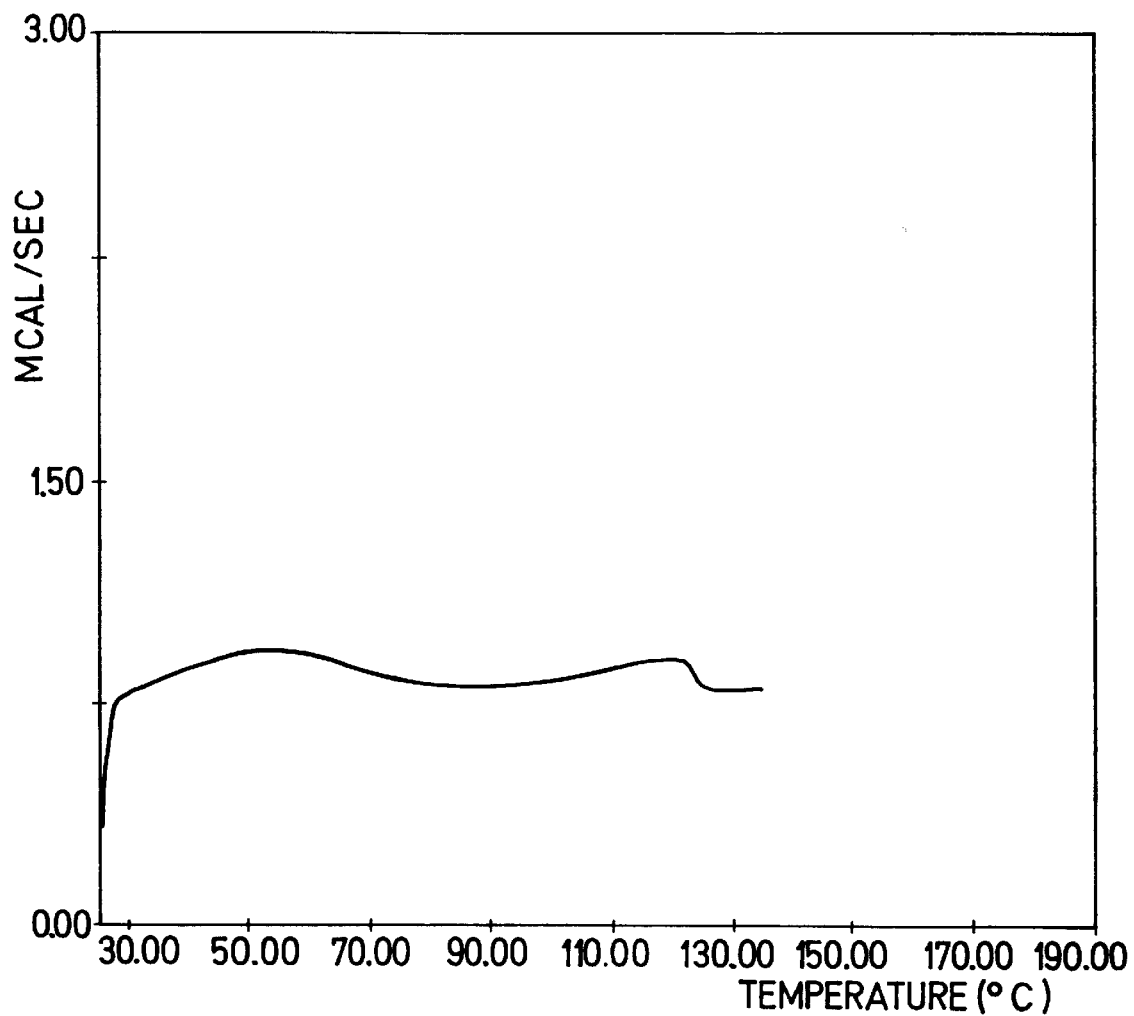
FIG. 6A shows DSC thermogram of mixture of racemic ibuproxam and methyl-β-cyclodextrin.
Figure 6B:
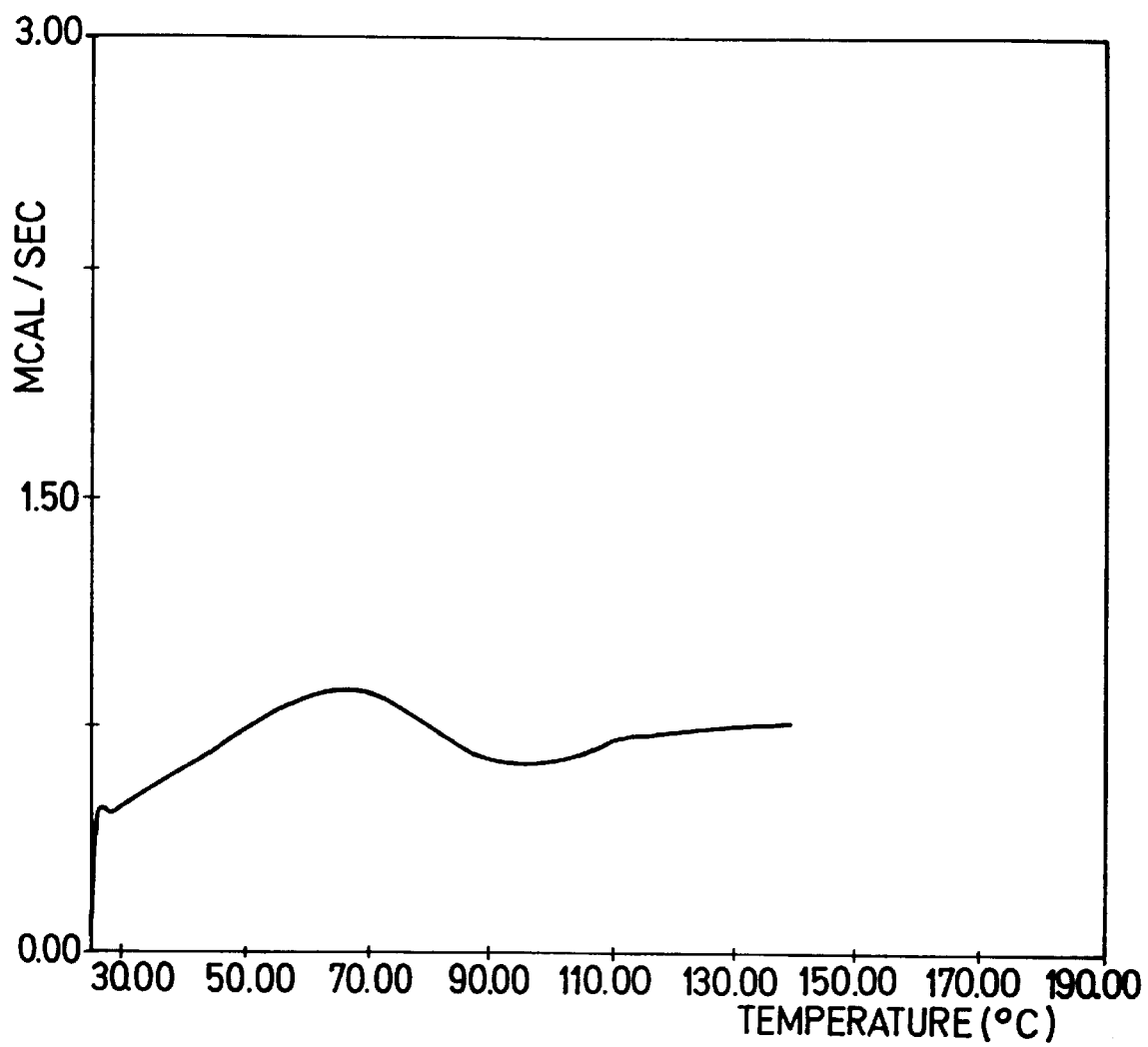
FIG. 6B shows DSC thermogram of inclusion complex of racemic buproxam with methyl-β-cyclodextrin.

In the curve of the obtained product there was not detected any endothermic transition for a melting point, characteristic of a physical mixture of ibuproxam/methyl-β-cyclodextrin at a temperature from 120° to 130° C. (FIGS. 6A and 6B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

FIG. 7 shows NMR spectrum of the complex of racemic ibuproxam with methyl-β-cyclodextrin.

b) Procedure in aqueous medium

Methyl-β-cyclodextrin (1.31 g; 1.0 mmole) was dissolved in water (10 ml). The obtained solution was heated to the temperature of 70° C. and racemic ibuproxam (0.221 g; 1.0 mmole) was added. It was vigorously stirred for another 5 minutes. The solution was frozen in liquid nitrogen and lyophilized. Inclusion complex (1.48 g; 96.7%) of racemic ibuproxam with methyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 4

Preparation of inclusion complex of S-(+)-ibuproxam with methyl-β-cyclodextrin a) Procedure in methanolic medium S-(+)-ibuproxam (0.221 g; 1.0 mmole) was added to a solution of methyl-β-cyclodextrin (1.31 g; 1.0 mmole) in methanol (10 ml). The obtained solution was stirred for another 5 minutes at room temperature. Methanol was then evaporated and the obtained complex was dried in vacuo at the temperature of 40° C. Inclusion complex (1.51 g; 98.6%) of S-(+)-ibuproxam with methyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}{}_{Na}$ of the complex formed are summarized in Table 2.

Differential scanning calorimetry (DSC thermogram)

Figure 8A:
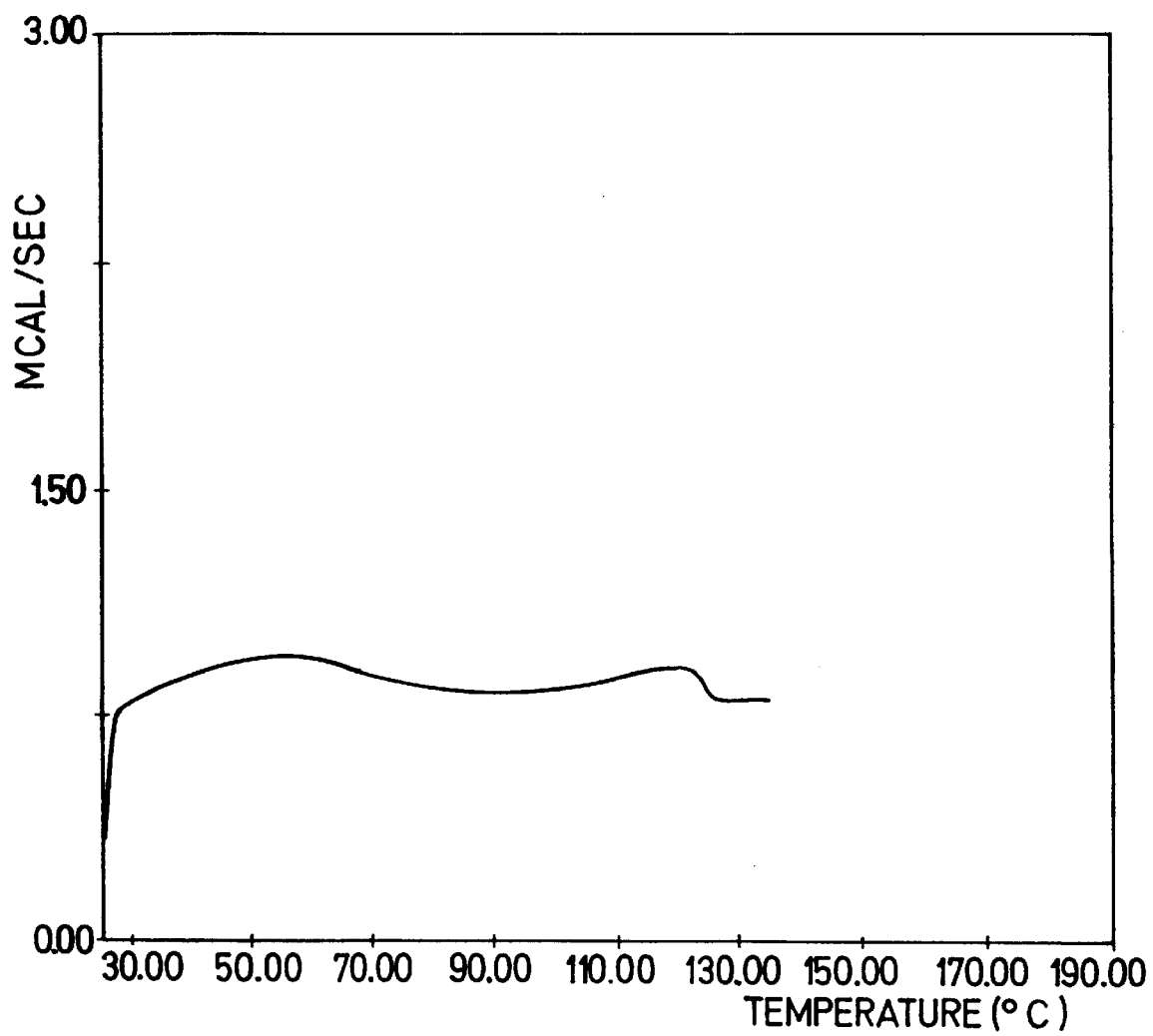
FIG. 8A shows DSC thermogram of mixture of S-(+)-ibuproxam.
Figure 8B:
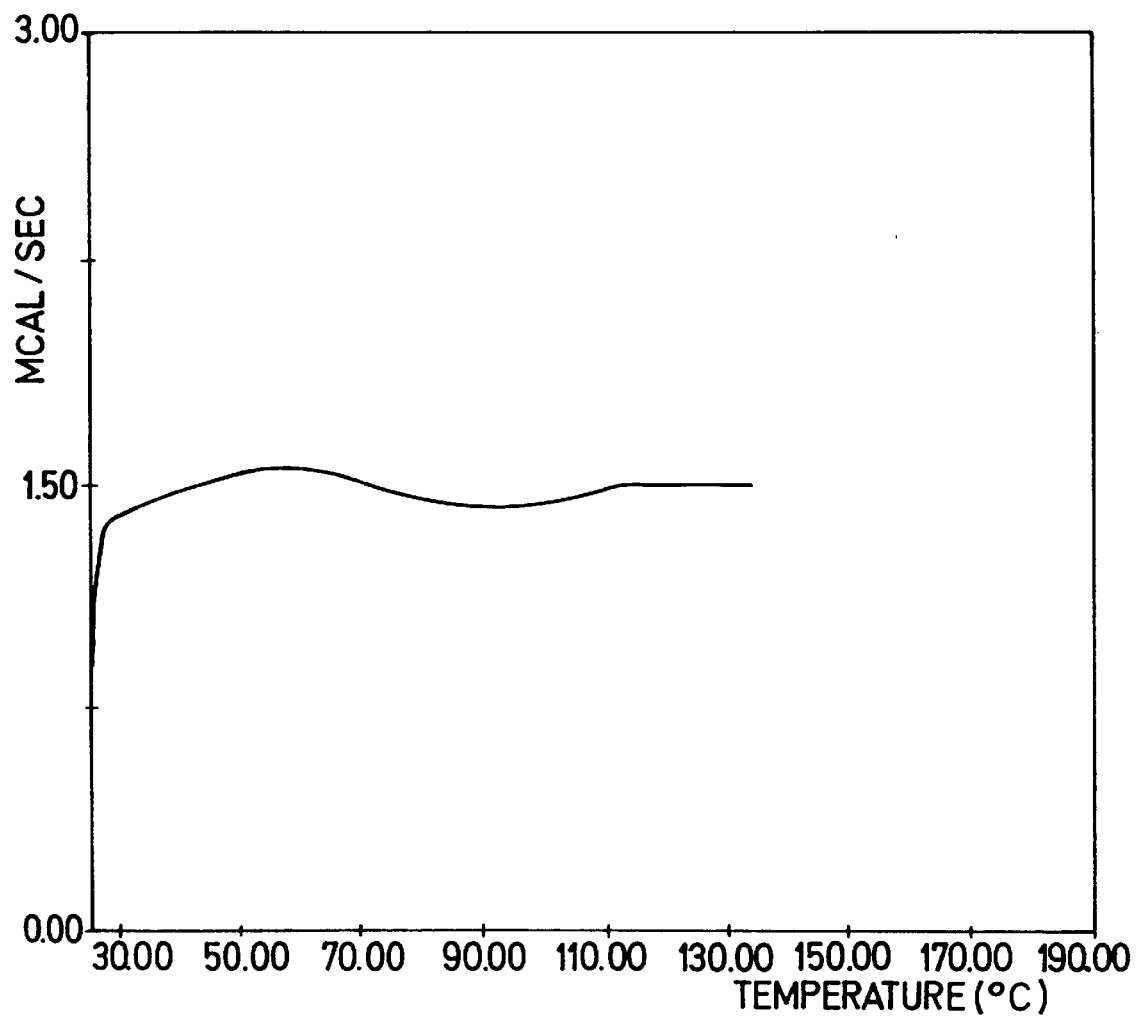
FIG. 8B shows DSC thermogram of inclusion complex of S-(+)-ibuproxam with methyl-β-cyclodextrin.

In the curve of the obtained product there was not detected any endothermic transition for a melting point, characteristic of a physical mixture of ibuproxam/methyl-β-cyclodextrin at a temperature from 120° to 130° C. (FIGS. 8A and 8B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

Figures 9A, 9B:
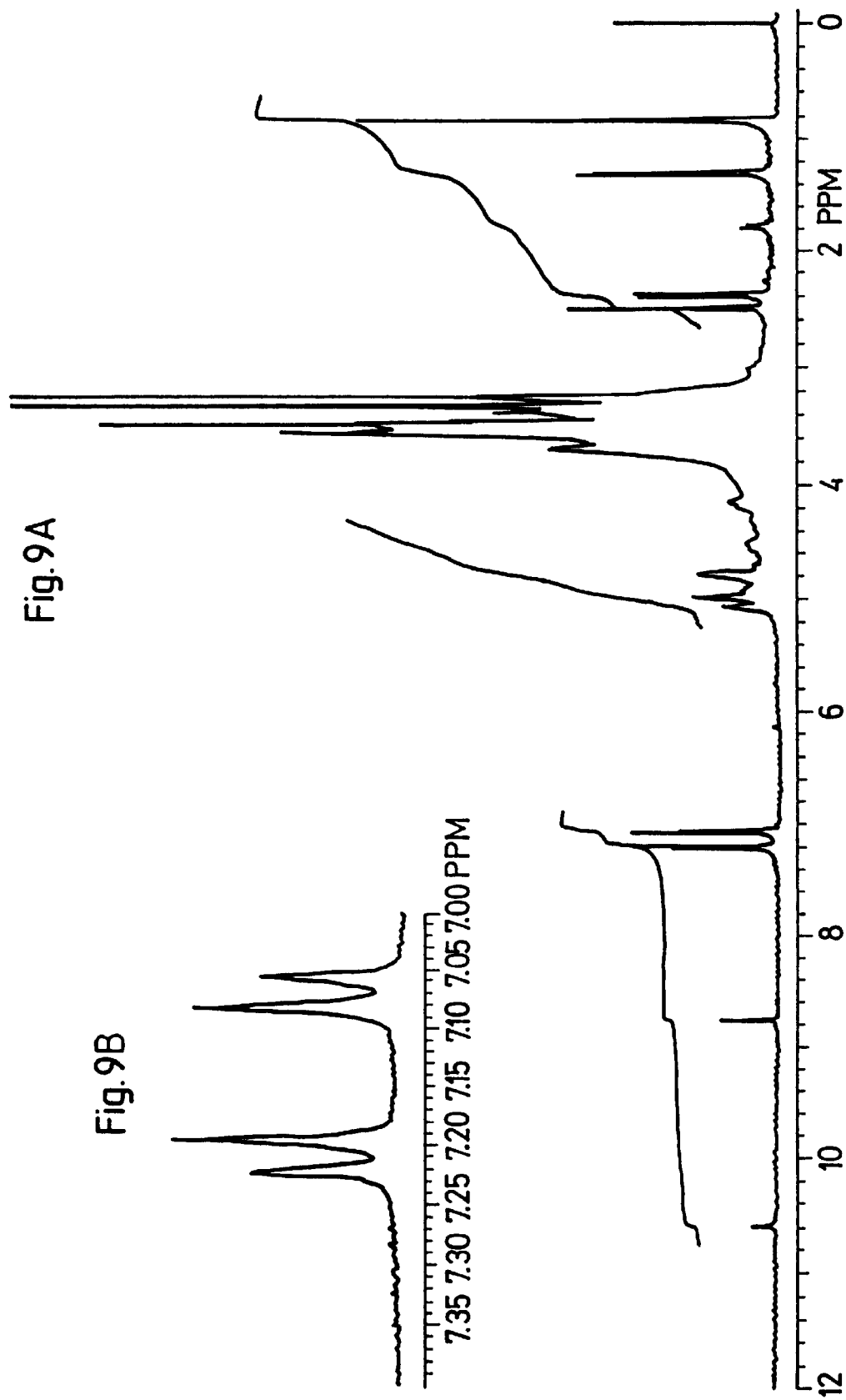
FIG. 9 shows NMR spectrum of the complex of S-(+)-ibuproxam with methyl-β-cyclodextrin.

FIG. 9 shows NMR spectrum of the complex of S-(+)-ibuproxam with methyl-β-cyclodextrin.

b) Procedure in aqueous medium

Methyl-β-cyclodextrin (1.31 g; 1.0 mmole) was dissolved in water (30 ml). The obtained solution was heated to the temperature of 70° C. and S-(+)-ibuproxam (0.221 g; 1.0 mmole) was added and it was vigorously stirred for another 15 minutes. The solution was frozen in liquid nitrogen and lyophilized. Inclusion complex (1.33 g; 86.9%) of S-(+)-ibuproxam with methyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 5

Preparation of inclusion complex of racemic ibuproxam with hydroxypropyl-β-cyclodextrin a) Procedure in methanolic medium Racemic ibuproxam (0.221 g; 1.0 mmole) was added to a solution of hydroxypropyl-β-cyclodextrin (1.38 g; 1.0 mmole) in methanol (10 ml) and the obtained solution was stirred for another 5 minutes at room temperature. Methanol was then evaporated and the obtained complex was dried in vacuo at the temperature of 40° C. Inclusion complex (1.57 g; 98.1%) of racemic ibuproxam with hydroxypropyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]_{23Na}$ of the complex formed are summarized in Table 1.

Differential scanning calorimetry (DSC thermogram)

Figure 10A:
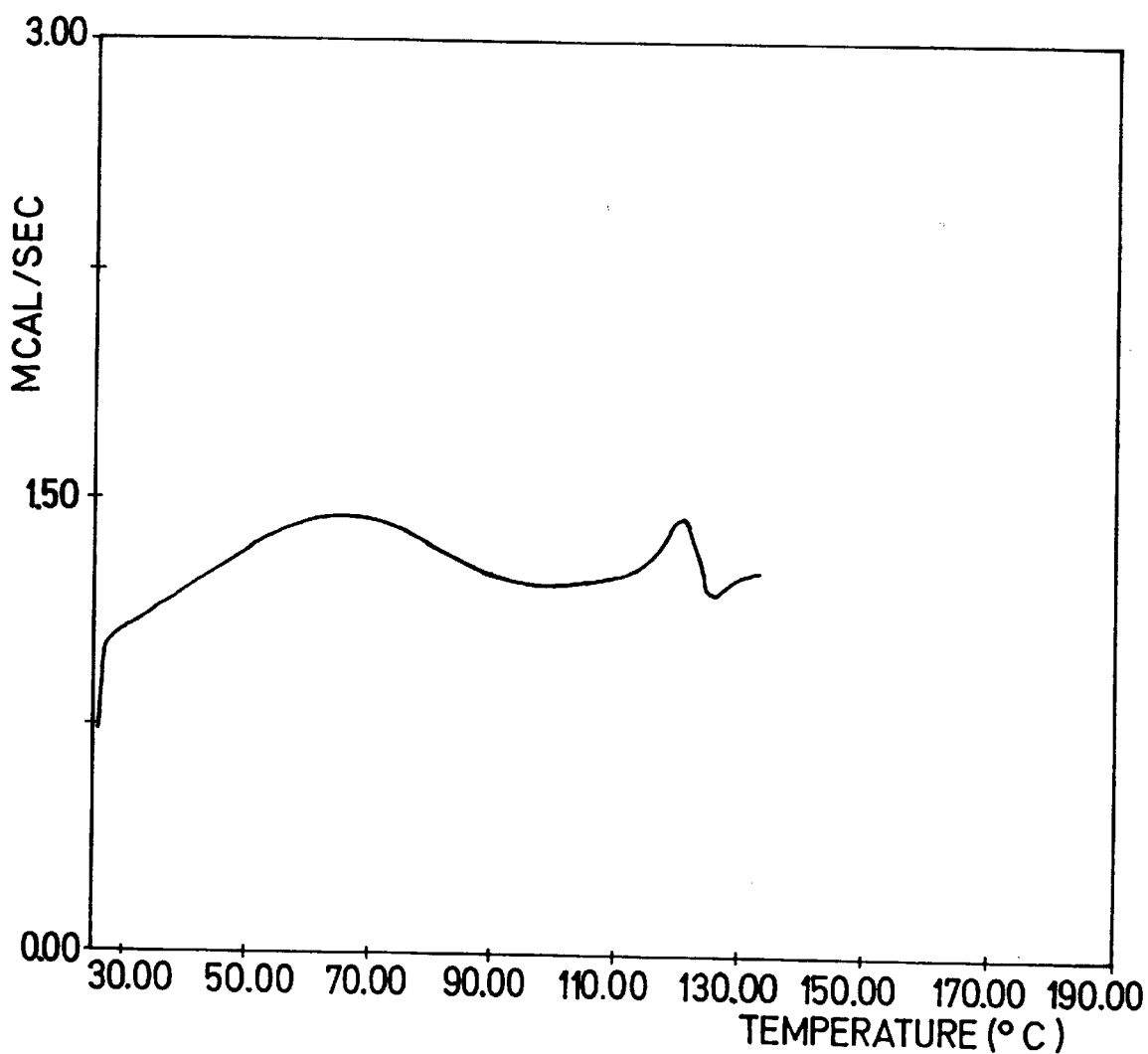
FIG. 10A shows DSC thermogram of mixture of racemic ibuproxam and hydroxypropyl β-cyclodextrin.
Figure 10B:
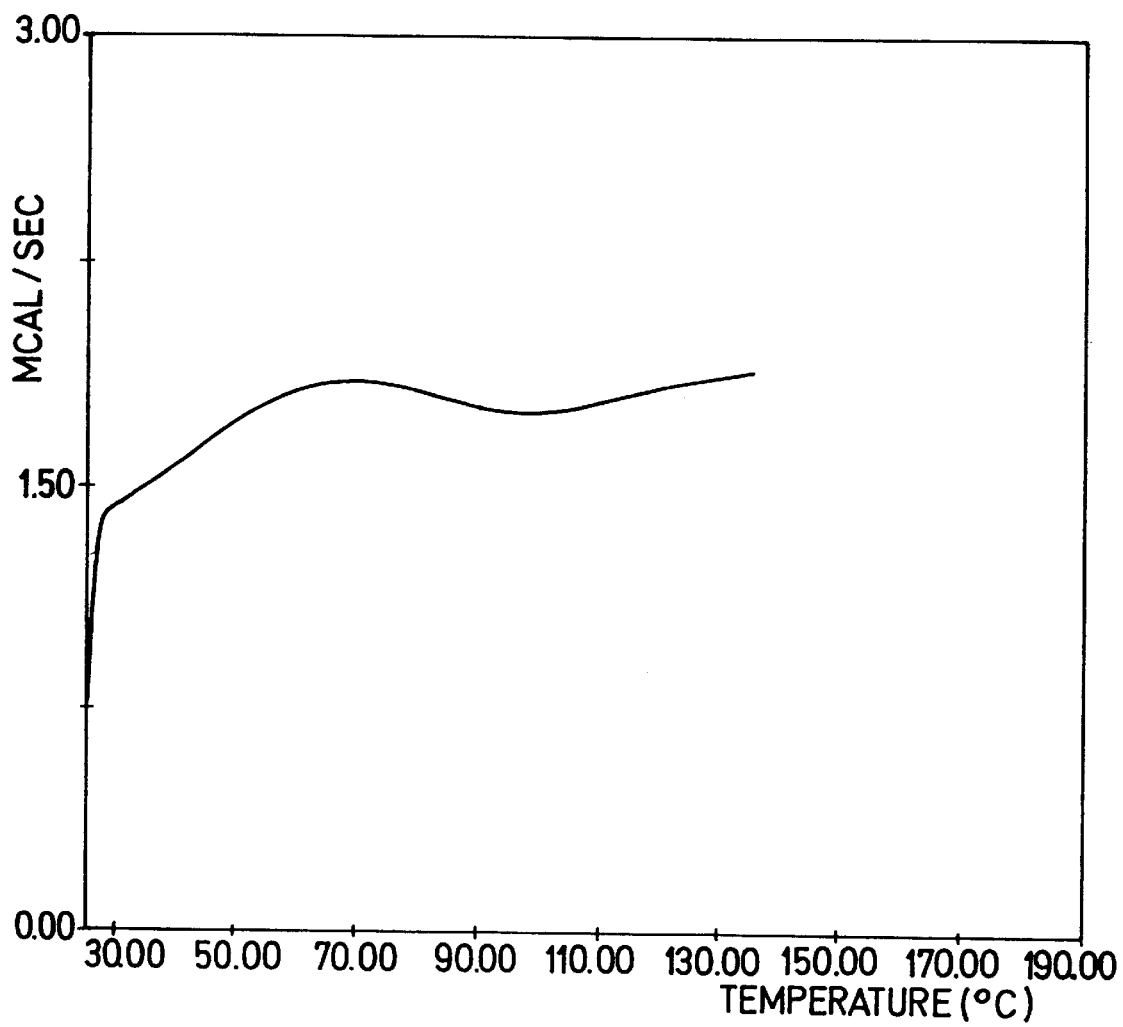
FIG. 10B shows DSC thermogram of inclusion complex of racemic ibuproxam with hydroxypropyl-β-cyclodextrin.

In the curve of the obtained product there was not detected any endothermic transition for a melting point, characteristic of a physical mixture of ibuproxam/hydroxypropyl-β-cyclodextrin at a temperature from 120° to 130° C. (FIGS. 10A and 10B).

NMR spectrum

In the $^1$H-NMR spectrum of the title complex in DMSO-D$_6$ solution the following change in the ibuproxam moiety was observed: at 7.19–7.25 ppm the signal for proton resonances in phenyl ring shifted to a higher field.

FIG. 11 shows NMR spectrum of the complex of racemic ibuproxam with hydroxypropyl-β-cyclodextrin.

b) Procedure in aqueous medium

Hydroxypropyl-β-cyclodextrin (1.38 g; 1.0 mmole) was dissolved in water (40 ml) and the obtained solution was heated to the temperature of 70° C. and racemic ibuproxam (0.221 g; 1.0 mmole) was added. It was vigorously stirred for another 15 minutes and then the solution was filtered. The filtrate was frozen in liquid nitrogen and lyophilized. Inclusion complex (1.40 g; 87.4%) of racemic ibuproxam with hydroxypropyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 6

Preparation of inclusion complex of S-(+)-ibuproxam with hydroxypropyl-β-cyclodextrin a) Procedure in methanolic medium S-(+)-ibuproxam (0.221 g; 1.0 mmole) was added to a solution of hydroxypropyl-β-cyclodextrin (1.38 g; 1.0 mmole) in methanol (10 ml) and the obtained solution was stirred for another 5 minutes at room temperature. Methanol was then evaporated and the obtained complex was dried in vacuo at the temperature of 40° C. Inclusion complex (1.56 g; 97.4%) of S-(+)-ibuproxam with hydroxypropyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}_{Na}$ of the complex formed are summarized in Table 2.

Differential scanning calorimetry (DSC thermogram)

Figure 12A:
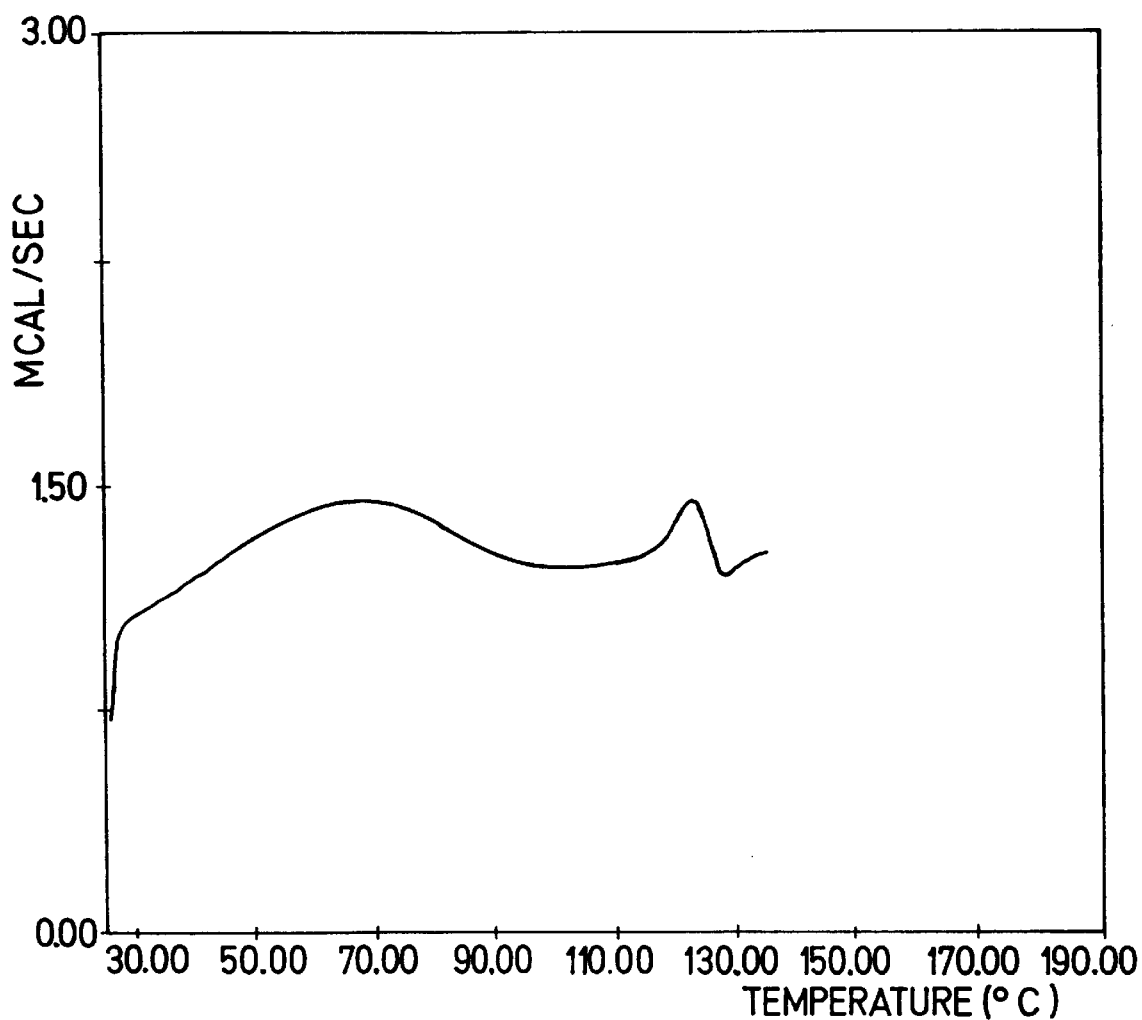
FIG. 12A shows DSC thermogram of S-(+)-ibuproxam and hydroxypropyl-β-cyclodextrin.
Figure 12B:
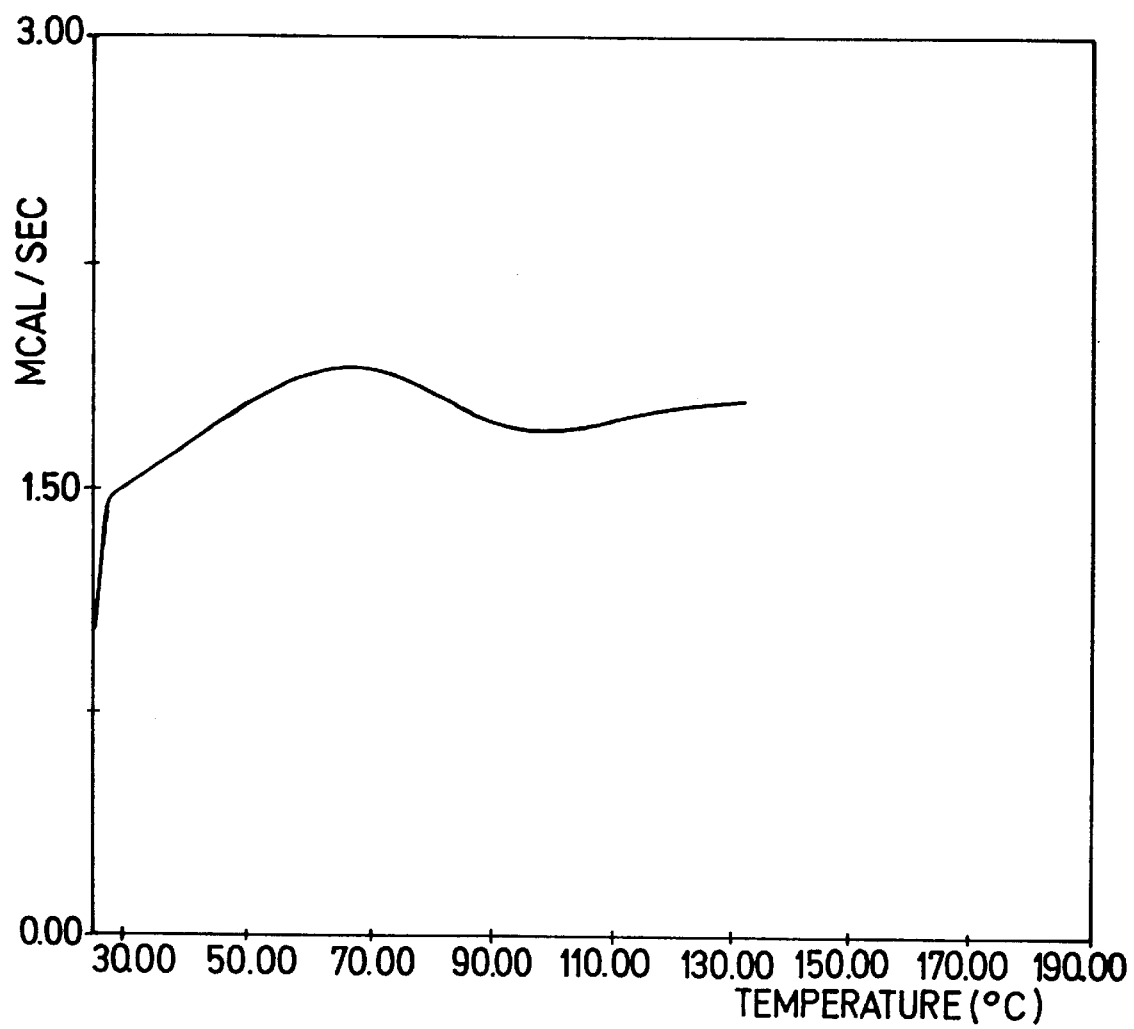
FIG. 12B shows DSC thermogram of inclusion complex of S-(+)-ibuproxam with hydroxypropyl-β-cyclodextrin.

In the curve of the obtained product there was detected no endothermic transition for a melting point, characteristic of a physical mixture of ibuproxam/hydroxypropyl-βcyclodextrin at a temperature from 120° to 130° C. (FIGS. 12A and 12B).

NMR spectrum

In the $^1$H-NMR spectrum of the title complex in DMSO-D$_6$ solution the following change in the ibuproxam moiety was observed: at 7.19–7.25 ppm the signal for proton resonances in phenyl ring shifted to a higher field.

FIG. 13 shows NMR spectrum of the complex of S-(+)-ibuproxam with hydroxypropyl-β-cyclodextrin.

b) Procedure in aqueous medium

Hydroxypropyl-β-cyclodextrin (1.38 g; 1.0 mmole) was dissolved in water (40 ml). The obtained solution was heated to the temperature of 70° C. and S-(+)-ibuproxam (0.221 g; 1.0 mmole) was added. It was vigorously stirred for another 15 minutes and the solution was filtered. The filtrate was frozen in liquid nitrogen and lyophilized. Inclusion complex (1.49 g; 9 3.1%) of S-(+)-ibuproxam with hydroxypropyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 7

Preparation of inclusion complex of racemic ibuproxam with hydroxyethyl-β-cyclodextrin a) Procedure in methanolic medium Racemic ibuproxam (0.221 g; 1.0 mmole) was added to a solution of hydroxyethyl-β-cyclodextrin (1.44 g; 1.0 mmole) in methanol (10 ml) and the obtained solution was stirred for another 5 minutes at room temperature. Methanol was then evaporated and the obtained complex was dried in vacuo at the temperature of 40° C. Inclusion complex (1.58 g; 95.1%) of racemic ibuproxam with hydroxyethyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}_{Na}$ of the complex formed are summarized in Table 1.

Differential scanning calorimetry (DSC thermogram)

Figure 14A:
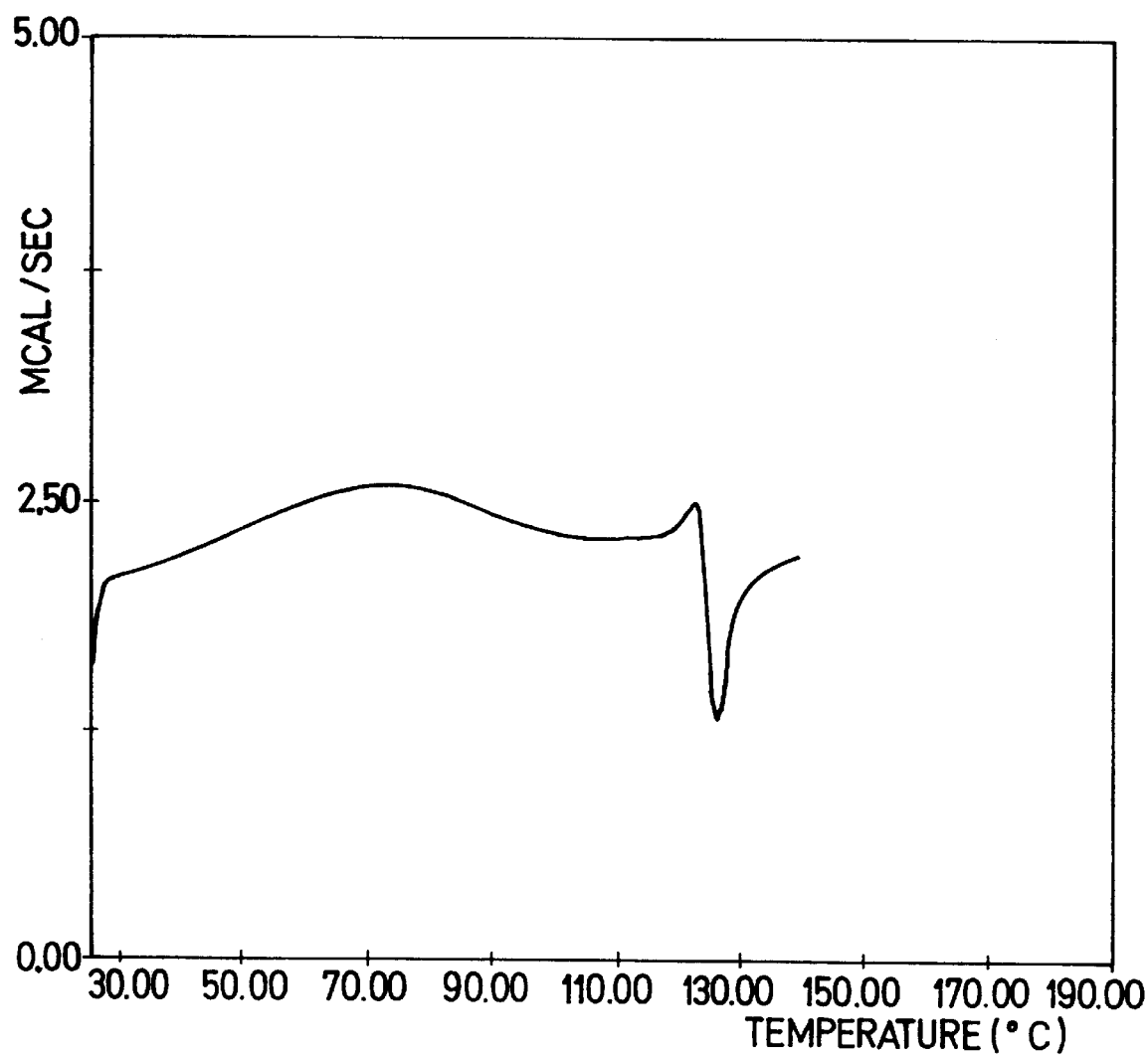
FIG. 14A shows DSC thermogram of mixture of racemic ibuproxam with hydroxyethyl-β-cyclodextrin.
Figure 14B:
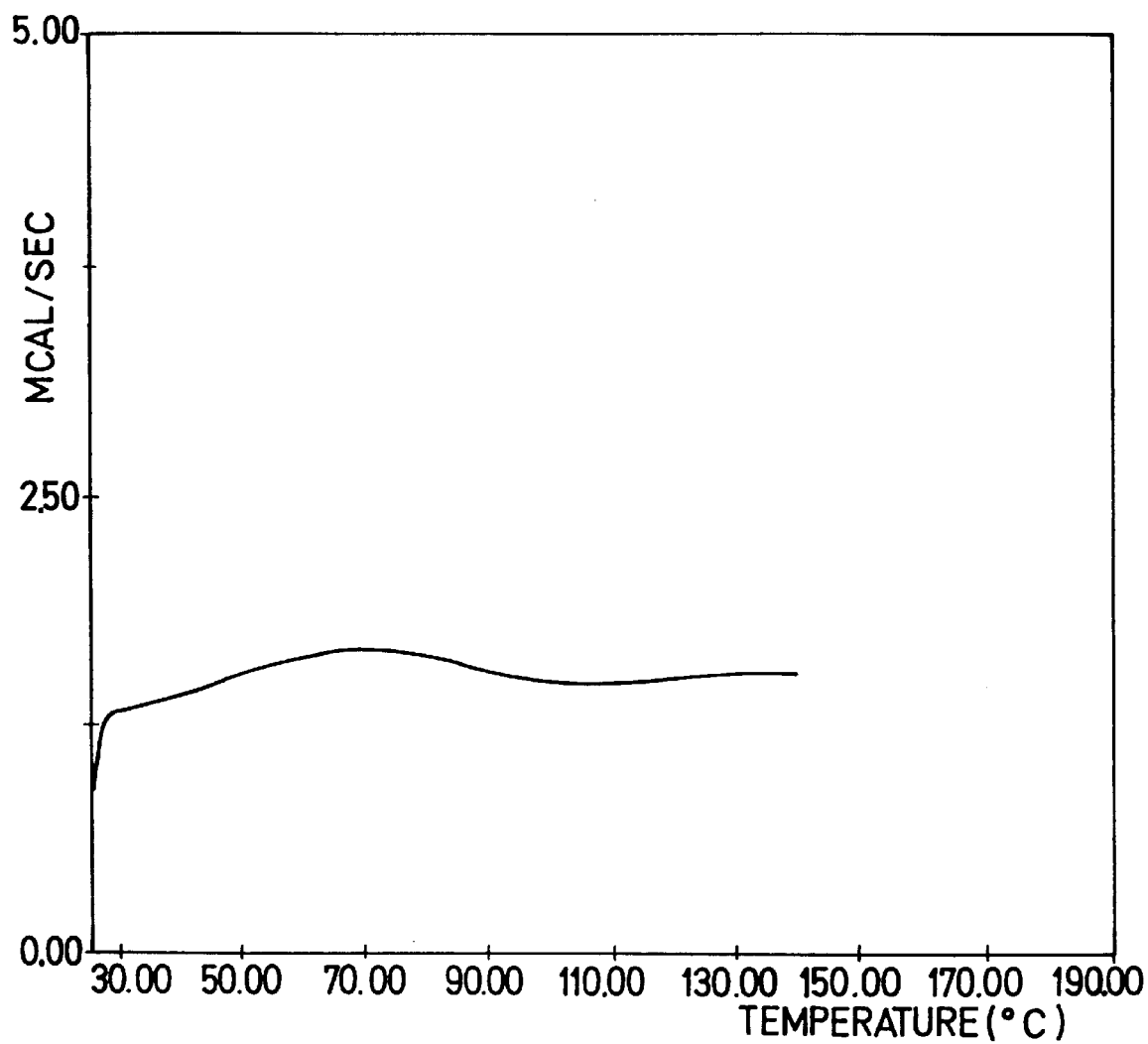
FIG. 14B shows DSC thermogram of inclusion complex of racemic ibuproxam with hydroxyethyl-β-cyclodextrin.

In the curve of the obtained product there was not detected any endothermic transition for a melting point, characteristic of a physical mixture of ibuproxam/hydroxyethyl-β-cyclodextrin at a temperature from 120° to 130° C. (FIGS. 14A and 14B).

NMR spectrum

In the $^1$H-NMR spectrum of the title complex in DMSO-D$_6$ solution the following change in the ibuproxam moiety was observed: at 7.19–7.25 ppm the signal for proton resonances in phenyl ring shifted to a higher field.

FIG. 15 shows NMR spectrum of the complex of racemic ibuproxam with hydroxyethyl-β-cyclodextrin.

b) Procedure in aqueous medium

Hydroxyethyl-β-cyclodextrin (1.44 g; 1.0 mmole) was dissolved in water (40 ml). The obtained solution was heated to the temperature of 70° C. and racemic ibuproxam (0.221 g; 1.0 mmole) was added. It was vigorously stirred for another 15 minutes and then the solution was filtered. The filtrate was frozen in liquid nitrogen and lyophilized. Inclusion complex (1.53 g; 92.1%) of racemic ibuproxam with hydroxyethyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 8

Preparation of inclusion complex of S-(+)-ibuproxam with hydroxyethyl-β-cyclodextrin a) Procedure in methanolic medium S-(+)-ibuproxam (0.221 g; 1.0 mmole) was added to a solution of hydroxyethyl-β-cyclodextrin (1.44 g; 1.0 mmole) in methanol (10 ml) and the obtained solution was stirred for another 5 minutes at room temperature. Methanol was then evaporated and the obtained complex was dried in vacuo at the temperature of 40° C. Inclusion complex (1.57 g; 94.5%) of S-(+)-ibuproxam with hydroxyethyl-β-cyclodextrin was obtained in the form of a white powder in the molar ratio of 1:1.

Data on reaction yields, ibuproxam content in the complex (determined theoretically and experimentally-spectrophotometric determination at the wavelength of 220 nm) and specific rotation $[\alpha]^{23}_{Na}$ of the complex formed are summarized in Table 2.

Differential scanning calorimetry (DSC thermogram)

Figure 16A:
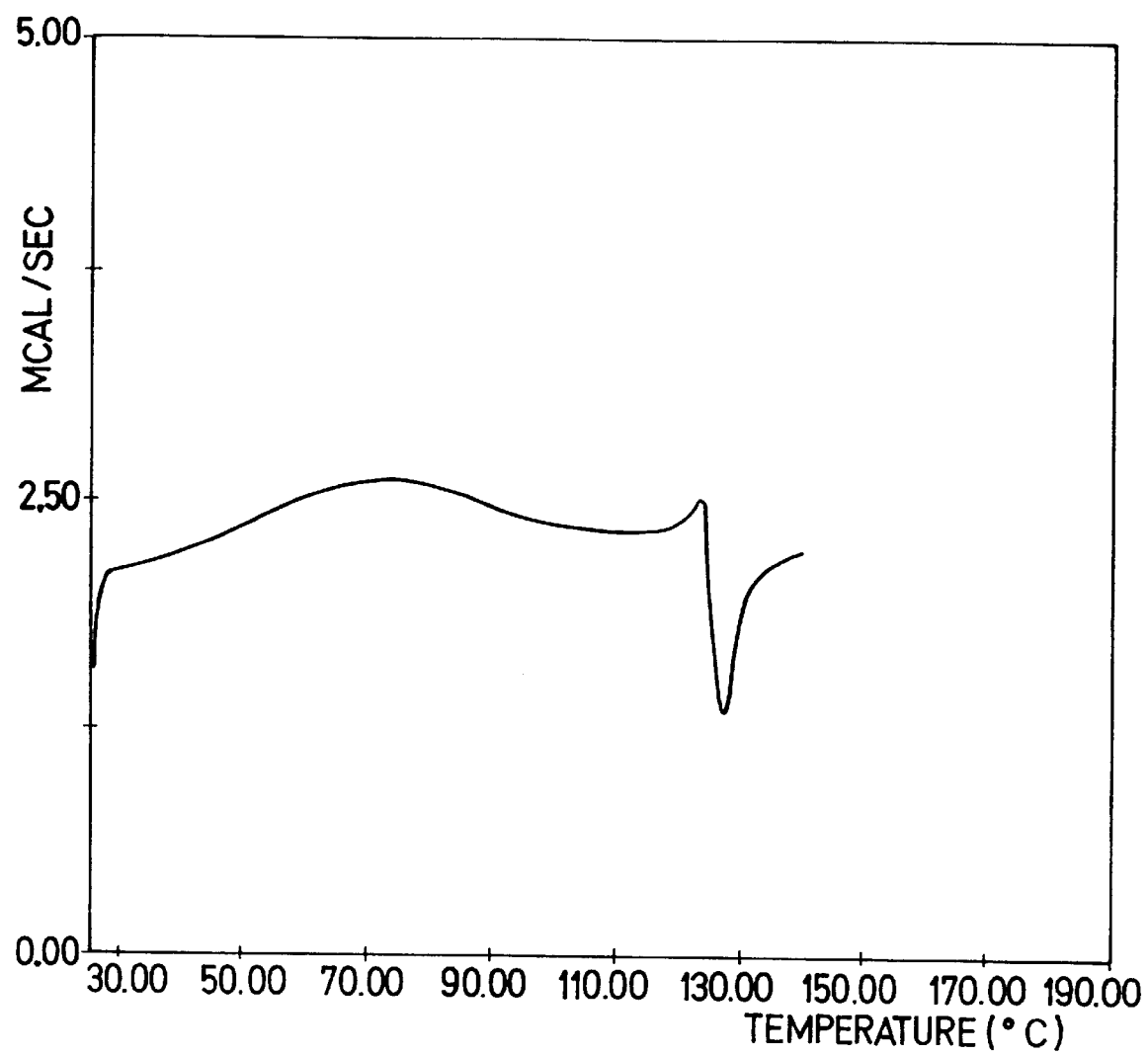
FIG. 16A shows DSC thermogram of mixture of S-(+)-ibuproxam hydroxyethyl-β-cyclodextrin.
Figure 16B:
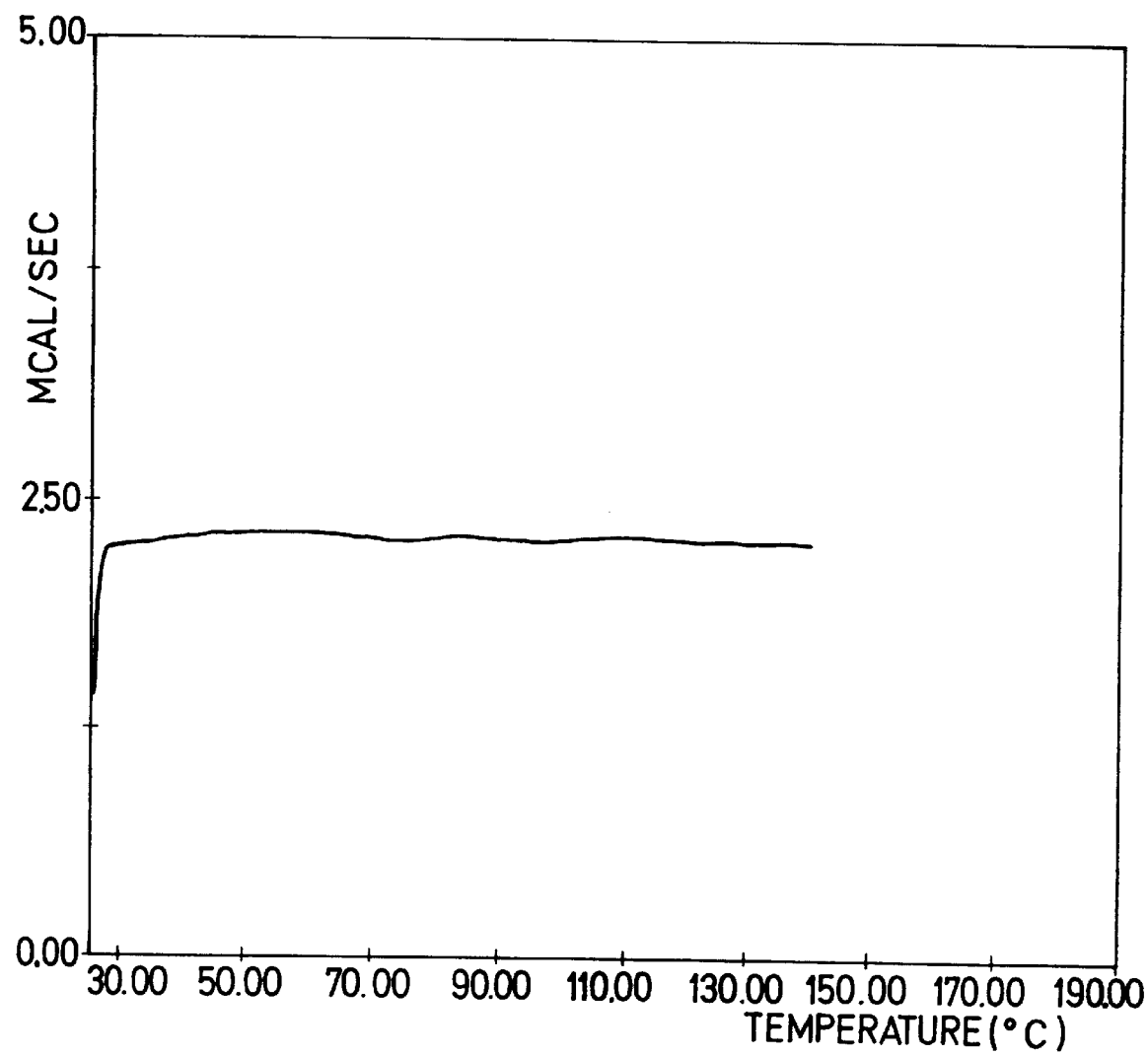
FIG. 16B shows DSC thermogram of inclusion complex of S-(+)-ibuproxam with hydroxyethyl-β-cyclodextrin.

In the curve of the obtained product there was not detected any endothermic transition for a melting point, characteristic of a physical mixture of ibuproxam/hydroxyethyl-β-cyclodextrin at a temperature from 120° to 130° C. (FIGS. 16A and 16B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

FIG. 17 shows NMR spectrum of the complex of S-(+)-ibuproxam with hydroxyethyl-β-cyclodextrin.

b) Procedure in aqueous medium

Hydroxyethyl-β-cyclodextrin (1.44 g; 1.0 mmole) was dissolved in water (40 ml). The obtained solution was heated to the temperature of 70° C. and S-(+)-ibuproxam (0.221 g; 1.0 mmole) was added. It was vigorously stirred for another 15 minutes and the solution was filtered. The filtrate was frozen in liquid nitrogen and lyophilized. Inclusion complex (1.52 g; 91.5%) of S-(+)-ibuproxam with hydroxyethyl-β-cyclodextrin was obtained in the form of a white powder in the molar ratio of 1:1.

Differential scanning calorimetry and NMR spectrum showed the same results as in the process for preparing inclusion complex in the methanolic medium.

EXAMPLE 9

Preparation of inclusion complex of racemic ibuproxam with triacetyl-β-cyclodextrin a) Procedure in organic solvent Triacetyl-β-cyclodextrin (2.018 g; 1.0 mmole) was dissolved in acetone (10 ml) and to the solution racemic ibuproxam (0.221 g; 1.0 mmole) was added during stirring at room temperature. It was stirred for another 5 minutes, then the clear solution was evaporated in vacuo at the temperature of 40° C. and the residue was dried in a vacuum drier at room temperature to the dry product. The title complex (2.23 g; 99.6%) was obtained in the form of a white powder in the molar ratio of 1:1, containing ibuproxam (9.6%).

Data on reaction yields, ibuproxam content in the complex (determined theoretically and experimentally-spectrophotometric determination at the wavelength of 220 nm) and specific rotation $[\alpha]^{23}_{Na}$ of the complex formed are summarized in Table 1.

Differential scanning calorimetry (DSC thermogram)

Figure 18A:
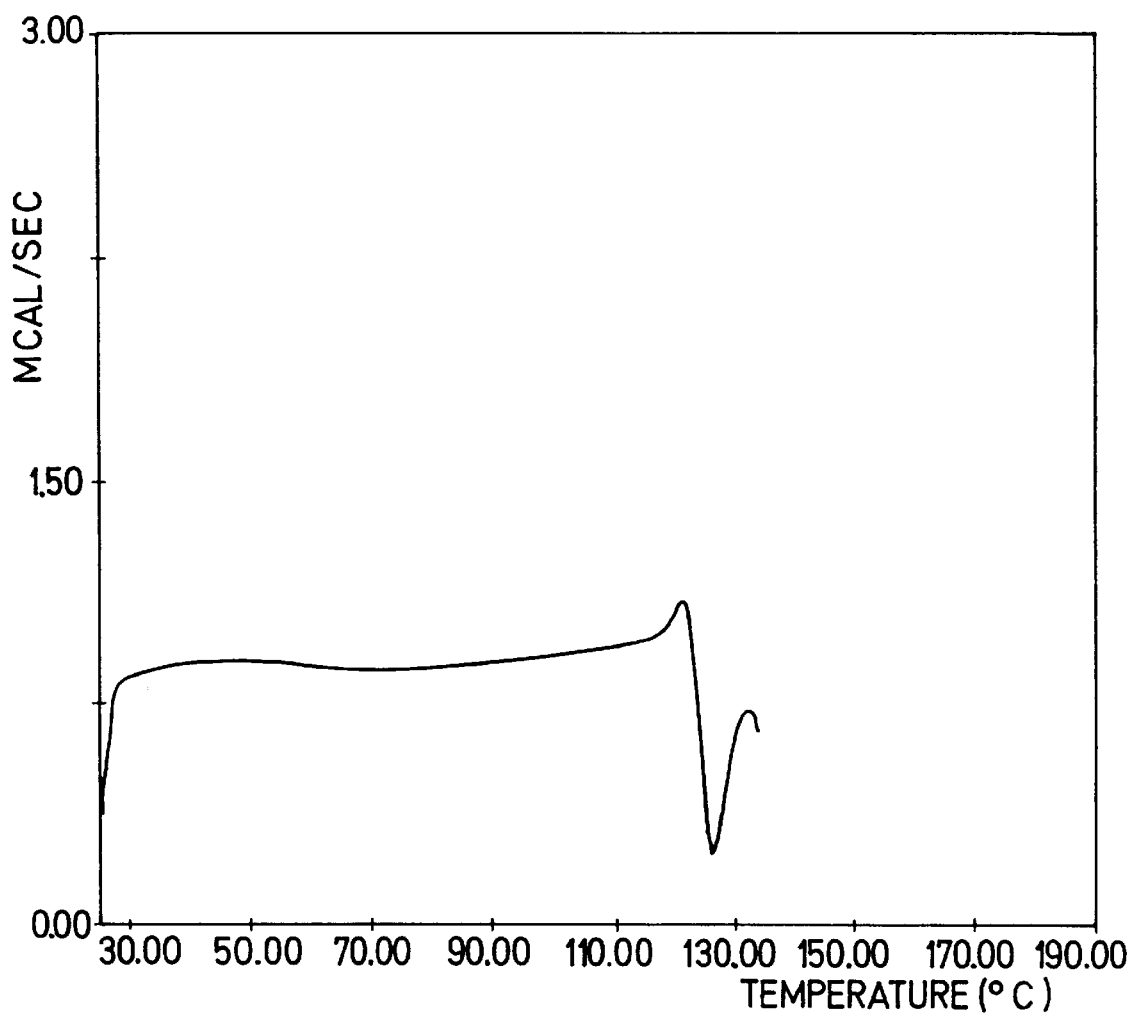
FIG. 18A shows DSC thermogram of mixture of racemic ibuproxam with triacetyl-β-cyclodextrin.
Figure 18B:
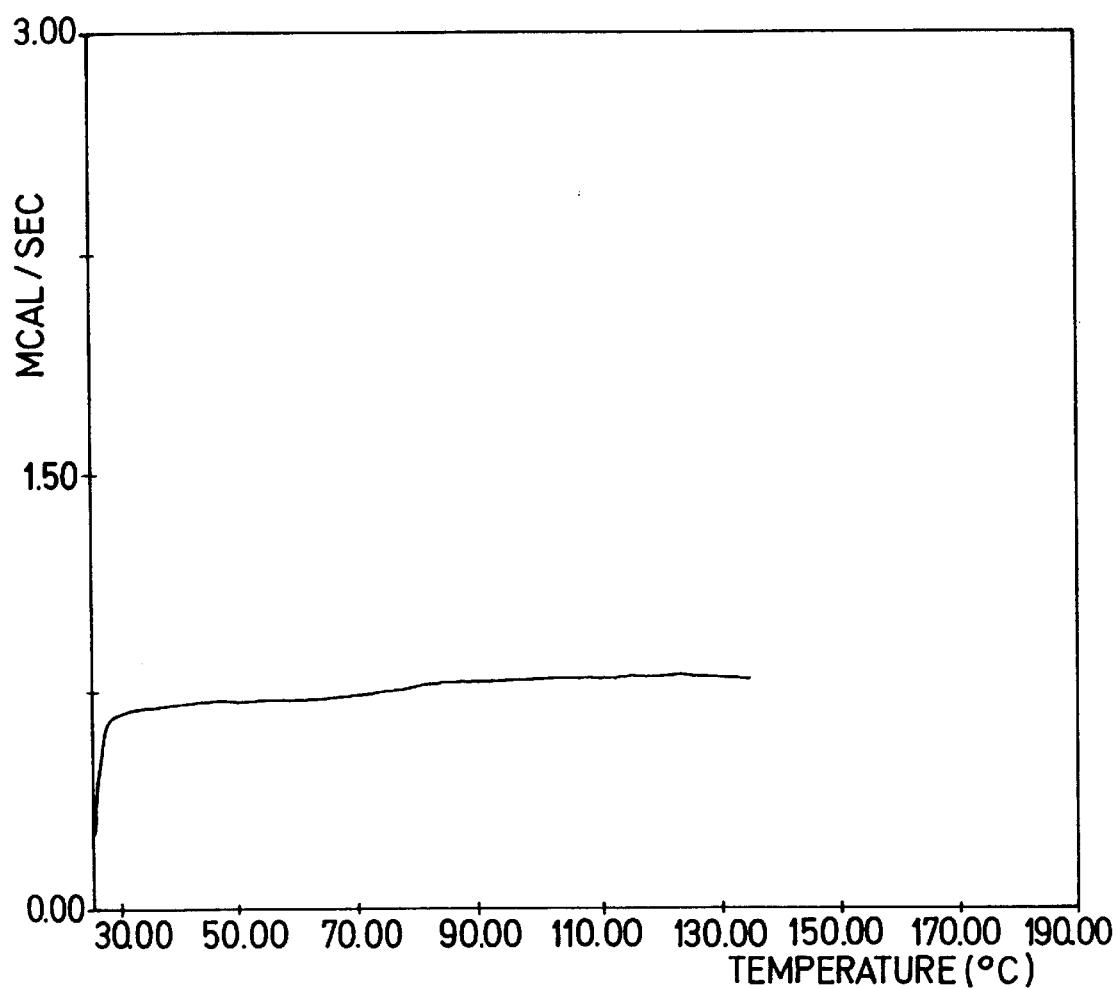
FIG. 18B shows DSC thermogram of inclusion complex of racemic ibuproxam with triacetyl-β-cyclodextrin.

In the curve of the obtained product there was not detected any endothermic transition for a melting point, characteristic of a physical mixture of ibuproxam/triacetyl-β-cyclodextrin at a temperature from 120° to 130° C. (FIGS. 18A and 18B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

FIG. 19 shows NMR spectrum of the complex of racemic ibuproxam with triacetyl-β-cyclodextrin.

b) Procedure in solvent mixture (acetone/water in the ratio 1:1)

Triacetyl-β-cyclodextrin (2.018 g; 1.0 mmole) was dissolved in acetone (3 ml) at the temperature of 40° C. and then to the obtained solution racemic ibuproxam (0.221 g; 1.0 mmole) was added under stirring. To the obtained clear solution water (5 ml) was added under vigorous stirring, it was cooled to a temperature from 0° to 5° C. and the formed precipitate was filtered off, dried in vacuo at the temperature of 40° C. and the title complex was obtained.

Differential scanning calorimetry and NMR spectrum showed the same results as in the process for preparing inclusion complex in organic solvent.

EXAMPLE 10

Preparation of inclusion complex of S-(+)-ibuproxam with triacetyl-β-cyclodextrin a) Procedure in organic solvent Triacetyl-β-cyclodextrin (2.018 g; 1.0 mmole) was dissolved in acetone (10 ml) and to the solution S-(+)-ibuproxam (0.221 g; 1.0 mmole) was added during stirring at room temperature. It was stirred for another 5 minutes, then the clear solution was evaporated in vacuo at the temperature of 40° C. and the residue was dried in a vacuum drier at room temperature to the dry product. The title complex (2.22 g; 99.2%) was obtained in the form of a white powder in the molar ratio of 1:1, containing S-(+)-ibuproxam (9.8%).

Data on reaction yields, ibuproxam content in the complex (determined theoretically and experimentally-spectrophotometric determination at the wavelength of 220 nm) and specific rotation $[\alpha]^{23}_{Na}$ of the complex formed are summarized in Table 2.

Differential scanning calorimetry (DSC thermogram)

Figure 20A:
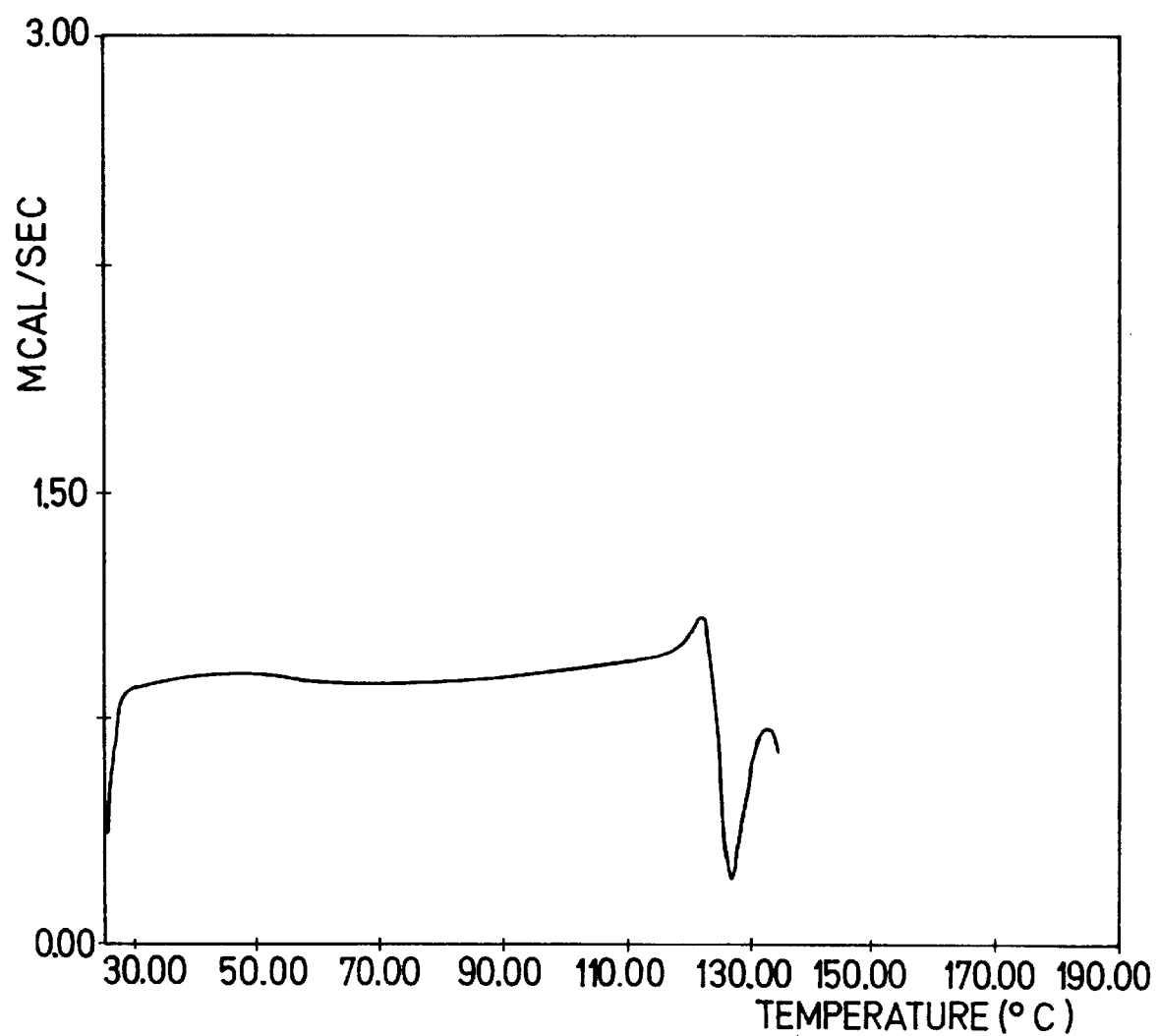
FIG. 20A shows DSC thermogram of mixture of S-(+)-ibuproxam and triacetyl-β-cyclodextrin.
Figure 20B:
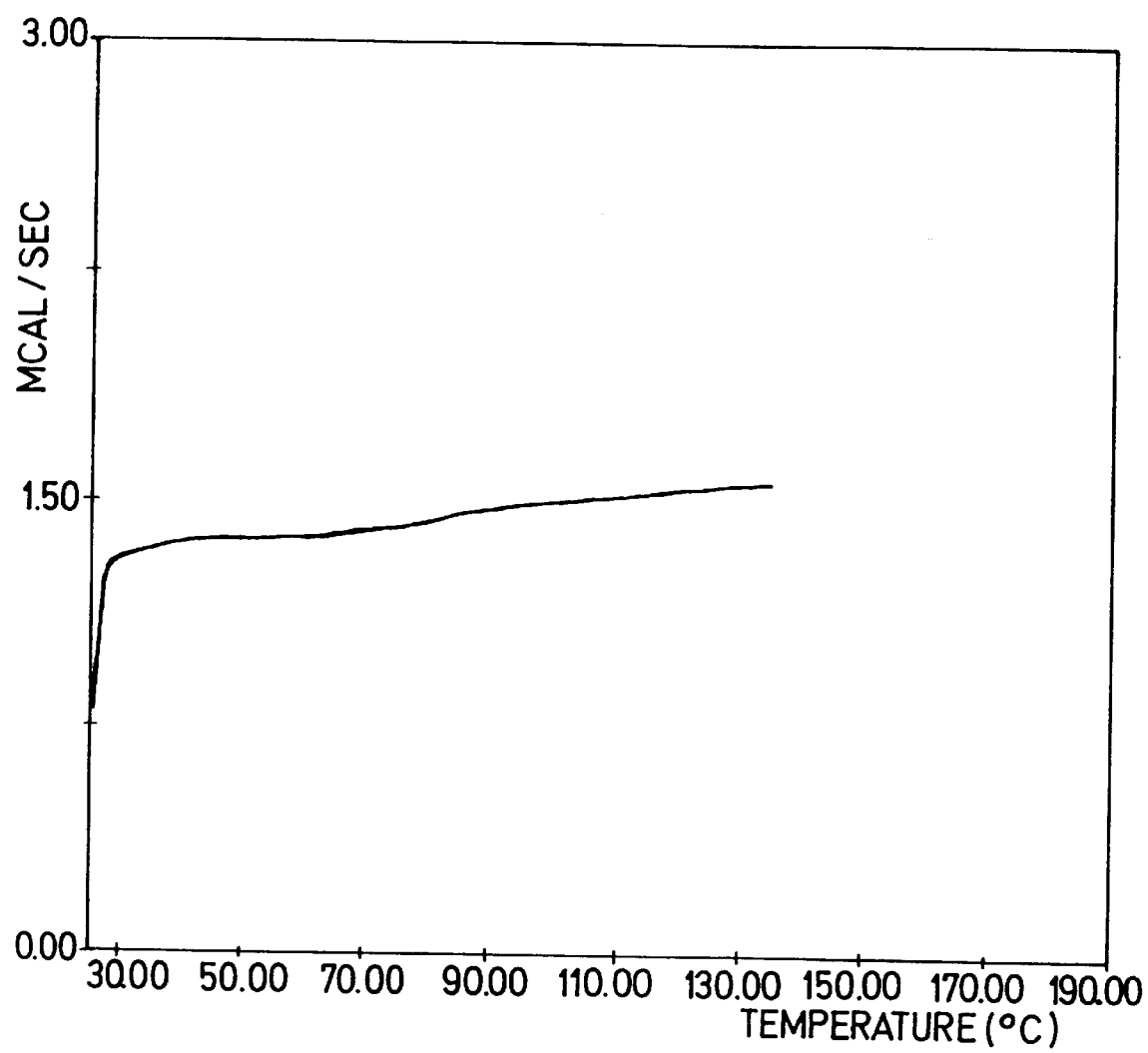
FIG. 20B shows DSC thermogram of inclusion complex of S-(+)-ibuproxam with triacetyl-β-cyclodextrin.

In the curve of the obtained product there was detected no endothermic transition for a melting point, characteristic of a physical mixture of ibuproxam/triacetyl-β-cyclodextrin at a temperature from 120° to 130° C. (FIGS. 20A and 20B).

NMR spectrum

In the $^1$H-NMR spectrum of the title complex in DMSO-$D_6$ solution the following change in the ibuproxam moiety was observed: at 7.19–7.25 ppm the signal for proton resonances in phenyl ring shifted to a higher field.

FIG. 21 shows NMR spectrum of the complex of S-(+)-ibuproxam with triacetyl-β-cyclodextrin.

b) Procedure in solvent mixture (acetone/water in the ratio 1:1)

Triacetyl-β-cyclodextrin (2.018 g; 1.0 mmole) was dissolved in acetone (3 ml) at the temperature of 40° C. and then to the solution S-(+)-ibuproxam (0.221 g; 1.0 mmole) was added under stirring. To the clear solution water (5 ml) was added under vigorous stirring, it was cooled to a temperature from 0° to 5° C. The formed precipitate was filtered off and dried in vacuo at the temperature of 40° C. to obtain the title complex.

Differential scanning calorimetry and NMR spectrum showed the same results as in the process for preparing inclusion complex in organic solvent.

TABLE 1

Reaction yield, ibuproxam content in the complex and specific rotation for inclusion complex of racemic ibuproxam with different derivatives of β-cyclodextrins in the ratio 1:1. Procedure in methanolic medium except for triacetyl-β-cyclodextrin where the results are summarized from the procedure in acetone.

| Inclusion complex of racemic ibuproxam with | reaction yield (%) | theor. cont. (%)* | exper. cont. (%)** | spec. rotation |
|---|---|---|---|---|
| methyl-β-cyclodextrin | 98.6 | 14.5 | 14.4 | +127.8° (ethanol abs., 0.30) |
| hydroxyethyl-β-cyclodextrin | 95.1 | 13.3 | 13.2 | +108.7° (ethanol abs., 0.30) |
| hydroxypropyl-β-cyclodextrin | 98.1 | 13.8 | 13.6 | +103.1° (ethanol abs., 0.30) |
| triacetyl-β-cyclodextrin | 99.6 | 9.9 | 9.6 | +109.5° (ethanol abs., 0.30) |

*theoretical content of ibuproxam in the complex
**experimentally determined content of ibuproxam in the complex

TABLE 2

Reaction yield, ibuproxam content in the complex and specific rotation for inclusion complex of S-(+)-ibuproxam with different derivatives of β-cyclodextrins in the ratio 1:1. Procedure in methanolic medium except for β-cyclodextrin where the medium is water, and for triacetyl-β-cyclodextrin where the the medium is acetone

| Inclusion complex of S-(+)-ibuproxam with | reaction yield (%) | theor. cont. (%)* | exper. cont. (%)** | spec. rotation |
|---|---|---|---|---|
| β-cyclodextrin | 94.4 | 16.3 | 16.2 | +133.1° (H₂O, 0.29) |
| methyl-β-cyclodextrin | 98.6 | 14.5 | 13.5 | +133.9° (ethanol abs. 0.30) |
| hydroxyethyl-β-cyclodextrin | 94.5 | 13.3 | 13.2 | +113.8° (ethanol abs., 0.30) |
| hydroxypropyl-β-cyclodextrin | 97.4 | 13.8 | 13.6 | +109.2° (ethanol abs., 0.30) |
| triacetyl-β-cyclodextrin | 99.2 | 9.9 | 9.8 | +113.9° (ethanol abs., 0.30) |

*theoretical content of ibuproxam in the complex
**experimentally determined content of ibuproxam in the complex

EXAMPLE 11

Water solubility

A suspension having the concentration of 200 mg inclusion complex of racemic or optically active S-(+)-ibuproxam in 10 ml water and having pH 5.8 was stirred for 1 hour (500 rpm) at room temperature. Then a sample was filtered through filter paper (blue ribbon) and diluted with absolute ethanol. The concentration of ibuproxam was determined spectrophotometrically at the wavelength of 220 nm and at room temperature.

TABLE 3

Solubility of ibuproxam in water

| Solubility of racemic ibuproxam | 0.11 mg/ml |
|---|---|
| inclusion complex of racemic ibuproxam with | solubility (mg/ml) |
| methyl-β-cyclodextrin | 2.8 |
| hydroxyethyl-β-cyclodextrin | 2.8 |
| hydroxypropyl-β-cyclodextrin | 2.5 |
| triacetyl-β-cyclodextrin | 0.4 |
| Solubility of S-(+)-ibuproxam | 0.2 (mg/ml) |
| inclusion complex of S-(+)-ibuproxam with | solubility (mg/ml) |
| β-cyclodextrin | 2.6 |
| methyl-β-cyclodextrin | 2.5 |
| hydroxyethyl-β-cyclodextrin | 2.5 |
| hydroxypropyl-β-cyclodextrin | 2.0 |
| triacetyl-β-cyclodextrin | 0.4 |

As evident from the above data the solubility of ibuproxam is significantly increased by binding its molecule into a cyclodextrin complex. There is no noticeable difference in solubilities of individual hydrophilic derivatives, but the solubility of ibuproxam is greater in the case of hydrophilic derivatives than in the case of hydrophobic derivatives of β-cyclodextrins.

EXAMPLE 12

Acute toxicity

In toxicological evaluation acute toxicity of S-(+)-ibuprofen, S-(+)-ibuproxam and inclusion complex of S-(+)-ibuproxam with β-cyclodextrin was established. The S-(+)-ibuproxam content in complex was 14.4%. In the test mice of Han-NMRI strain of both sexes, weight 19 to 24 g, and female rats of Han-WISTAR strain, weight 220 to 250 g, were used. The active substance was suspended in arachis oil and applied perorally. The volume of the applied suspension was 0.2 ml/20 g body weight in mice and 0.2 ml/200 g body weight in rats. Before the test the animals were fasted for 24 hours and after application, water and food were available ad libitum. The results of testing are summarized in Table 4.

TABLE 4

Acute toxicity of selected substances after peroral application

| Substance | No. of animals in the group | Dosis mg/kg | % of deaths in 24 h | % of deaths after 15 days | LD₅₀ mg/kg |
|---|---|---|---|---|---|
| 1. Male mice | | | | | |
| S-(+)-ibuprofen | 10 | 2000 | 0 | 30 | >2000 |
| S-(+)-ibuproxam | 10 | 2000 | 0 | 0 | >2000 |
| S-(+)-ibuproxam in inclusion complex with β-cyclodextrin | 10 | 2000 | 0 | 0 | >2000 |
| 2. Female mice | | | | | |
| S-(+)-ibuprofen | 10 | 1000 | 10 | 10 | >2000 |
| S-(+)-ibuprofen | 10 | 2000 | 10 | 10 | >2000 |
| S-(+)-ibuproxam | 10 | 2000 | 0 | 0 | >2000 |
| S-(+)-ibuproxam | 10 | 1000 | 0 | 0 | >2000 |
| S-(+)-ibuproxam in inclusion complex with β-cyclodextrin | 10 | 2000 | 0 | 0 | >2000 |
| 3. Female rats | | | | | |
| S-(+)-ibuprofen | 6 | 1000 | 0 | 83.3 | <1000 |
| S-(+)-ibuproxam | 6 | 1000 | 0 | 50 | ≈1000 |
| S-(+)-ibuproxam in inclusion complex with β-cyclodextrin | 6 | 2000 | 0 | 0 | >2000 |

It is evident from the above table that acute toxicity of S-(+)-ibuprofen in all test animals is greater than acute toxicity of S-(+)-ibuproxam, irrespective of its being free or bound in the complex with β-cyclodextrin. At the dosis of 2000 mg/kg of S-(+)-ibuprofen 30% of male mice died in 15 days and no animal died at the dosis of 2000 mg/kg of S-(+)-ibuproxam or inclusion complex of S-(+)-ibuproxam with β-cyclodextrin. At the dosis of 2000 mg/kg of S-(+)-ibuprofen 10% of female mice died in 15 days and again no animal died at the dosis of 1000 mg/kg or 2000 mg/kg of S-(+)-ibuproxam or inclusion complex of S-(+)-ibuproxam with β-cyclodextrin.

The difference in acute toxicity between free S-(+)-ibuproxam and S-(+)-ibuproxam bound into inclusion complex with β-cyclodextrin showed in rats which were more susceptible to test substances. At the dosis of 1000 mg/kg of S-(+)-ibuprofen 83.3% of the animals died in 15 days, at the dosis of 1000 mg/kg of S-(+)-ibuproxam 50% of the animals died after 15 days, whereas also at the increased dosis of 2000 mg/kg of S-(+)-ibuproxam bound into inclusion complex with β-cyclodextrin no animal died.

A comparative analysis of the toxicological results for different test animals shows that rats are much more susceptible to ibuprofen than mice, but equally susceptible to ibuproxam as mice. The mean lethal dosis ($LD_{50}$) for S-(+)-ibuprofen for mice of both sexes is greater than 2000 mg/kg at peroral application, but for female rats it is under 1000 mg/kg. The mean lethal dosis for S-(+)-ibuproxam for mice of both sexes is greater than 2000 mg/kg at peroral application, yet for femal rats it is approximately 1000 mg/kg. The mean lethal dose for inclusion complex of S-(+)-ibuproxam with β-cyclodextrin is for mice of both sexes and for female rats greater than 2000 mg/kg.

After peroral application of S-(+)-ibuprofen to male mice in the dosis of 2000 mg/kg, 30% of animals died in 48 hours, whereas in female mice at 1000 mg/kg and at the dosis of 2000 mg/kg 10% of animals died already in the first 24 hours. In female rats after peroral application of ibuprofen in the dosis of 1000 mg/kg, even 83.3% of the animals died in 6 days.

After peroral application of S-(+)-ibuproxam in mice of both sexes at the dosis of 2000 mg/kg, no animal died in 15 days, whereas in female rats at the same dosis 50% of the tested animals died in 15 days.

After peroral application of inclusion complex of S-(+)-ibuproxam no test animal died irrespective of the dosis, which was 1000 mg/kg or 2000 mg/kg.

It is evident from the above data that the inclusion complex of optically active S-(+)-ibuproxam is less toxic than S-(+)-ibuproxam alone, which is in turn less toxic than S-(+)-ibuprofen, which is also the priority aim of the present invention.

EXAMPLE 13

Antiinflammatory action

Antiinflammatory action was measured in vivo by the inhibition of oedema caused by carrageenin.

Rats, which were fasted overnight, were given 100 mg/kg of the test substance 1 hour before the injection of 0.1 ml 1% carrageenin suspension. The inhibition of the formed oedema was measured 3 hours after injecting carrageenin.

TABLE 5

Measurement of antiinflammatory action in vivo at the dosis of 100 mg/kg of the active substance applied perorally

| Substance | antiinflammatory action |
|---|---|
| S-(+)-ibuproxam | 37 |
| complex of S-(+)-ibuproxam with β-cyclodextrin | 75 |

The measurement in vivo of the antiinflammatory action showed that the inclusion complex of S-(+)-ibuproxam with β-cyclodextrin exhibited a twice greater antiinflammatory action than free optically active S-(+)-enatiomer.

It is evident from the above data that the inclusion complex of optically active S-(+)ibuproxam with β-cyclodextrin showed greater antiinflammatory action than free optically active S-(+)-ibuproxam, which, however, showed greater antiinflammatory action than free racemic ibuproxam, which is also the priority aim of the present invention.

EXAMPLE 14

Effect on gastric mucous membrane

Effect of S-(+)-ibuprofen, S-(+)-ibuproxam and inclusion complex of S-(+)-ibuproxam with β-cyclodextrin on gastric mucous membrane was measured.

Rats, which were fasted overnight, were given perorally 100 mg/kg of the active substance. After 4 hours its effect on irritation of gastric mucous membrane was measured in a way that the rate of bleeding in stomach and frequency of ulcers was determined.

TABLE 6

Measurement of the effect on gastric mucous membrane

| Substance | dose (mg/kg) | irritation |
|---|---|---|
| S-(+)-ibuprofen | 30 | 12 |
| S-(+)-ibuproxam | 30 | 0 |
| inclusion complex of S-(+)-ibuproxam with β-cyclodextrin | 15 | 0 |

The above data show that free S-(+)-ibuproxam and S-(+)-ibuproxam bound into an inclusion complex with β-cyclodextrin did not exhibit an irritating effect on gastric mucous membrane of the animals.

EXAMPLE 15

Antiinflammatory action and effect on gastric mucous membrane

Testing antiinflammatory action was carried out according to the method of Winter C. A. et al., Proc. Soc. Exp. Biol. Med., 111 (1962). The effect on gastric mucous membrane was measured in such a way that changes on gastric mucous membrane were observed under magnifying glass. In the test 120 male rats (Wistar), weight 140 to 170 g, were used.

Animals were fasted 24 hours before the beginning of the test with water at libitum. Active substances to be tested were applied in the dosis of 25 mg/kg, 50 mg/kg and 100 mg/kg perorally in the form of a suspension in a 10% gum arabic solution. Control group of rats was given only the vehicle (i.e. the 10% gum arabic solution). After 60 minutes the rats were administered a subcutaneous injection of 0.1 ml of 1.5% carrageenin suspension in 0.9% NaCl solution into a subplantar part of the right hind paw. 0.1 ml of 0.9% NaCl solution only was injected into a subplantar part of the left hind paw as a control. Volumes of both paws were measured by means of plethysmometer meter (Model 7150, Ugo Basile) immediately and then in intervals of 1 to 5 hours after carrageenin application. The percentage of the swelling of the hind paw was calculated according to the following equation:

% swelling of hind paw =

$$\left( \frac{\text{right paw volume} - \text{starting right paw volume}}{\text{starting right paw volume}} - \frac{\text{left paw volume} - \text{starting left paw volume}}{\text{starting left paw volume}} \right) \cdot 100$$

The testing of the antiinflammatory action was concluded 6 hours after peroral application of the active substance or 5 hours after injecting carrageenin. Then the rats were decapitated and the stomachs were removed and washed with 0.9% NaCl solution. By incision along the lesser bend the stomach was opened and gastric mucous membrane was observed under magnifying glass and possible changes were evaluated according to the following scale (Cashin C. H. et al., J. Pharm. Pharmac. 29 (1977):

| | |
|---|---|
| 0 | no lesions |
| 0.5 | hyperaemia |
| 1 | one or two indistinct lesions |
| 1.5 | more than two indistinct lesions |
| 2 | frequent lesions |
| 3 | very frequent lesions |
| 4 | lesions are noticeable over the whole gastric mucous membrane |

TABLE 7

Therapeutic index: ratio of $UD_{50}/ED_{30}$

| Substance | $UD_{50}/ED_{30}$ (95% confidence limit) |
|---|---|
| S-(+)-ibuprofen | 0.54 |
| racemic ibuproxam | 1.37 |
| S-(+)-ibuproxam | 1.63 |
| inclusion complex of S-(+)-ibuproxam with β-cyclodextrin | 2.21 |

$UD_{50}$ - calculated dosis of the active substance in mg per 1 kg of the animal, which dosis caused a change of the gastric mucous membrane at least with the note 1 at 50% animals
$ED_{30}$ - calculated dosis of the active substance in mg per 1 kg of the animal, which dosis caused a 30% inhibition of carrageenin-induced oedema It is evident from the above table that the therapeutic index was the most advantageous (the greatest) at the inclusion complex of S-(+)-ibuproxam with β-cyclodextrin since it was four times greater than for S-(+)-ibuprofen, 1.6 times greater than for racemic ibuproxam and 1.4-times greater than for S-(+)-ibuproxam. This means that at the dosis of the active substance which caused a 30% inhibition of carrageenin-induced oedema, in the case of the inclusion complex of S-(+)-ibuproxam with β-cyclodextrin a lesser irritation of the gastric mucous membrane occurred in comparison with S-(+)-ibuproxam, which caused a 1.2 times lesser irritation of the gastric mucous membrane in comparison with racemic ibuproxam, which in turn caused a 2.5 times lesser irritation than S-(+)-ibuprofen.

EXAMPLE 16
Alleviation of pain

The effect of alleviating pain was tested with the number of convulsions caused by phenylbenzoquinone. Female mice, weight 15 to 22 g, were fasted before the test for 24 hours and after the application water and food were ad libitum. 30 minutes after peroral introduction of the suspension of active substance in 10% gum arabic solution, individual mice were intraperitoneally administered 0.25 ml of 0.02% phenylbenzoquinone solution. Only the vehicle was applied to a control group of animals. The number of phenylbenzoquinone-induced convulsions was pursued 5 to 20 minutes after the application thereof.

TABLE 8

Measurement of the effect of alleviating pain

| Substance | $ED_{50}$ (mg/kg) (95% confidence limit) |
|---|---|
| S-(+)-ibuproxam | 73.0 |
| S-(+)-ibuproxam in inclusion complex with β-cyclodextrin | 25.0 |

$ED_{50}$ - calculated dosis of the active substance in mg per 1 kg of the animal, which dosis caused a 50% pain protection It is evident from the above table that $ED_{50}$ value in the case of S-(+)-ibuproxam bound into the inclusion complex with β-cyclodextrin was even three times lesser than the value for S-(+)-ibuproxam alone, which means that in the case of S-(+)-ibuproxam bound into the inclusion complex with β-cyclodextrin the same effect as with S-(+)-ibuproxam alone could be achieved by a three times lesser dosis.

EXAMPLE 17
X-ray powder diffraction

In Table 9 there are demonstrated lattice spacings d (nm) and intensities (I) of X-ray diffraction for S-(+)-ibuproxam, racemic ibuproxam, β-cyclodextrin, hydroxypropyl-β-cyclodextrin, triacetyl-β-cyclodextrin, for physical mixtures of S-(+)-ibuproxam with β-cyclodextrin, hydroxypropyl-β-cyclodextrin and triacetyl-β-cyclodextrin, for physical mixtures of racemic ibuproxam with hydroxypropyl-β-cyclodextrin and triacetyl-β-cyclodextrin, for inclusion complexes of S-(+)-ibuproxam with β-cyclodextrin, hydroxypropyl-β-cyclodextrin and triacetyl-β-cyclodextrin, and for inclusion complexes of racemic ibuproxam with hydroxypropyl-β-cyclodextrin and triacetyl-β-cyclodextrin. The analysis was made on Philips PW 1710 diffractometer on Al-substrate at the wavelength of λ=0.15418 nm (CuKα).

TABLE 9

Characteristic diffraction maximums

| β-cyclodextrin | | S-(+)-ibuproxam | | physical mixture of S-(+)-ibuproxam + β-cyclodextrin | | inclusion complex of S-(+)-ibuproxam + β-cyclodextrin | |
|---|---|---|---|---|---|---|---|
| d(nm) | I | d(nm) | I | d(nm) | I | d(nm) | I |
| 0.701 | 75 | 0.383 | 52 | 0.699 | 72 | 0.508 | 68 |
| 0.687 | 100 | 0.380 | 53 | 0.493 | 74 | 0.502 | 91 |
| 0.657 | 53 | 0.369 | 100 | 0.471 | 65 | 0.497 | 100 |
| 0.495 | 51 | 0.354 | 45 | 0.467 | 88 | 0.489 | 78 |
| 0.487 | 68 | 0.264 | 46 | 0.418 | 79 | 0.477 | 72 |
| 0.472 | 55 | 0.237 | 51 | 0.392 | 95 | 0.472 | 81 |
| | | 0.205 | 50 | 0.387 | 99 | 0.468 | 83 |
| | | | | 0.327 | 73 | 0.368 | 59 |
| | | | | 0.257 | 100 | 0.236 | 67 |
| | | | | 0.204 | 92 | 0.204 | 84 |

| hydroxypropyl-β-cyclodextrin | | S-(+)β-ibuproxam | | physical mixture of S-(+)-ibuproxam + hydroxypropyl-β-cyclodextrin | | inclusion complex of S-(+)-ibuproxam + hydroxypropyl-β-cyclodextrin | |
|---|---|---|---|---|---|---|---|
| d(nm) | I | d(nm) | I | d(nm) | I | d(nm) | I |
| 0.500 | 86 | 0.383 | 52 | 0.493 | 80 | 0.488 | 92 |
| 0.490 | 89 | 0.380 | 53 | 0.478 | 81 | 0.469 | 91 |
| 0.486 | 89 | 0.369 | 100 | 0.467 | 89 | 0.458 | 87 |

TABLE 9-continued

| 0.470 | 100 | 0.354 | 45 | 0.456 | 86 | 0.458 | 92 |
| --- | --- | --- | --- | --- | --- | --- | --- |
| 0.454 | 88 | 0.264 | 46 | 0.442 | 84 | 0.448 | 81 |
|  |  | 0.237 | 51 | 0.205 | 100 | 0.204 | 100 |
|  |  | 0.205 | 50 |  |  |  |  |

| triacetyl-β-cyclodextrin | | S-(+)-ibuproxam | | physical mixture of S-(+)-ibuproxam + triacetyl-β-cyclodextrin | | inclusion complex of S-(+)-ibuproxam + triacetyl-β-cyclodextrin | |
| --- | --- | --- | --- | --- | --- | --- | --- |
| d(nm) | I | d(nm) | I | d(nm) | I | d(nm) | I |
| 0.470 | 68 | 0.383 | 52 | 0.474 | 92 | 0.416 | 78 |
| 0.441 | 72 | 0.380 | 53 | 0.468 | 98 | 0.408 | 78 |
| 0.438 | 61 | 0.369 | 100 | 0.445 | 99 | 0.399 | 84 |
| 0.401 | 68 | 0.354 | 45 | 0.403 | 90 | 0.385 | 80 |
| 0.204 | 100 | 0.264 | 46 | 0.387 | 100 | 0.390 | 78 |
|  |  | 0.237 | 51 | 0.385 | 85 | 0.204 | 100 |
|  |  | 0.205 | 50 |  |  |  |  |

| hydroxypropyl-β-cyclodextrin | | racemic ibuproxam | | physical mixture of racemic ibuproxam + hydroxypropyl-β-cyclodextrin | | inclusion complex of racemic ibuproxam + hydroxypropyl-β-cyclodextrin | |
| --- | --- | --- | --- | --- | --- | --- | --- |
| d(nm) | I | d(nm) | I | d(nm) | I | d(nm) | I |
| 0.500 | 86 | 1.225 | 95 | 0.480 | 82 | 0.480 | 80 |
| 0.490 | 89 | 1.133 | 74 | 0.473 | 92 | 0.464 | 80 |
| 0.486 | 89 | 0.634 | 43 | 0.468 | 100 | 0.457 | 79 |
| 0.470 | 100 | 0.471 | 83 | 0.462 | 89 | 0.448 | 79 |
| 0.454 | 88 | 0.382 | 100 | 0.382 | 87 | 0.204 | 100 |

| triacetyl-β-cyclodextrin | | racemic ibuproxam | | physical mixture of racemic ibuproxam + triacetyl-β-cyclodextrin | | inclusion complex of racemic ibuproxam + triacetyl-β-cyclodextrin | |
| --- | --- | --- | --- | --- | --- | --- | --- |
| d(nm) | I | d(nm) | I | d(nm) | I | d(nm) | I |
| 0.470 | 68 | 1.225 | 95 | 0.473 | 94 | 0.424 | 80 |
| 0.441 | 72 | 1.133 | 74 | 0.464 | 89 | 0.407 | 79 |
| 0.438 | 61 | 0.634 | 43 | 0.438 | 100 | 0.404 | 79 |
| 0.401 | 68 | 0.471 | 83 | 0.402 | 94 | 0.394 | 80 |
| 0.204 | 100 | 0.382 | 100 | 0.388 | 88 | 0.204 | 100 |

Figure 22B:
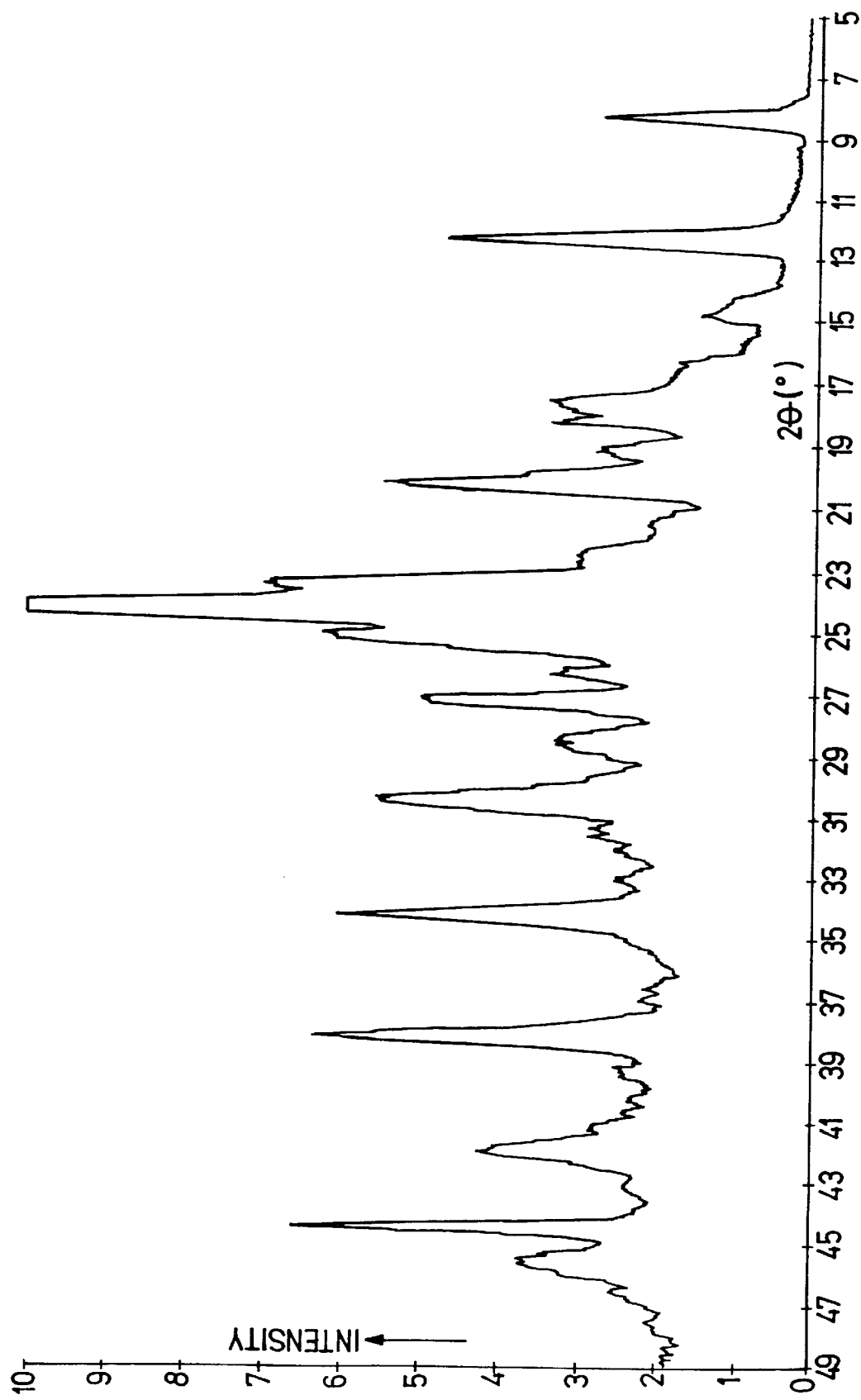
Figure 22C:
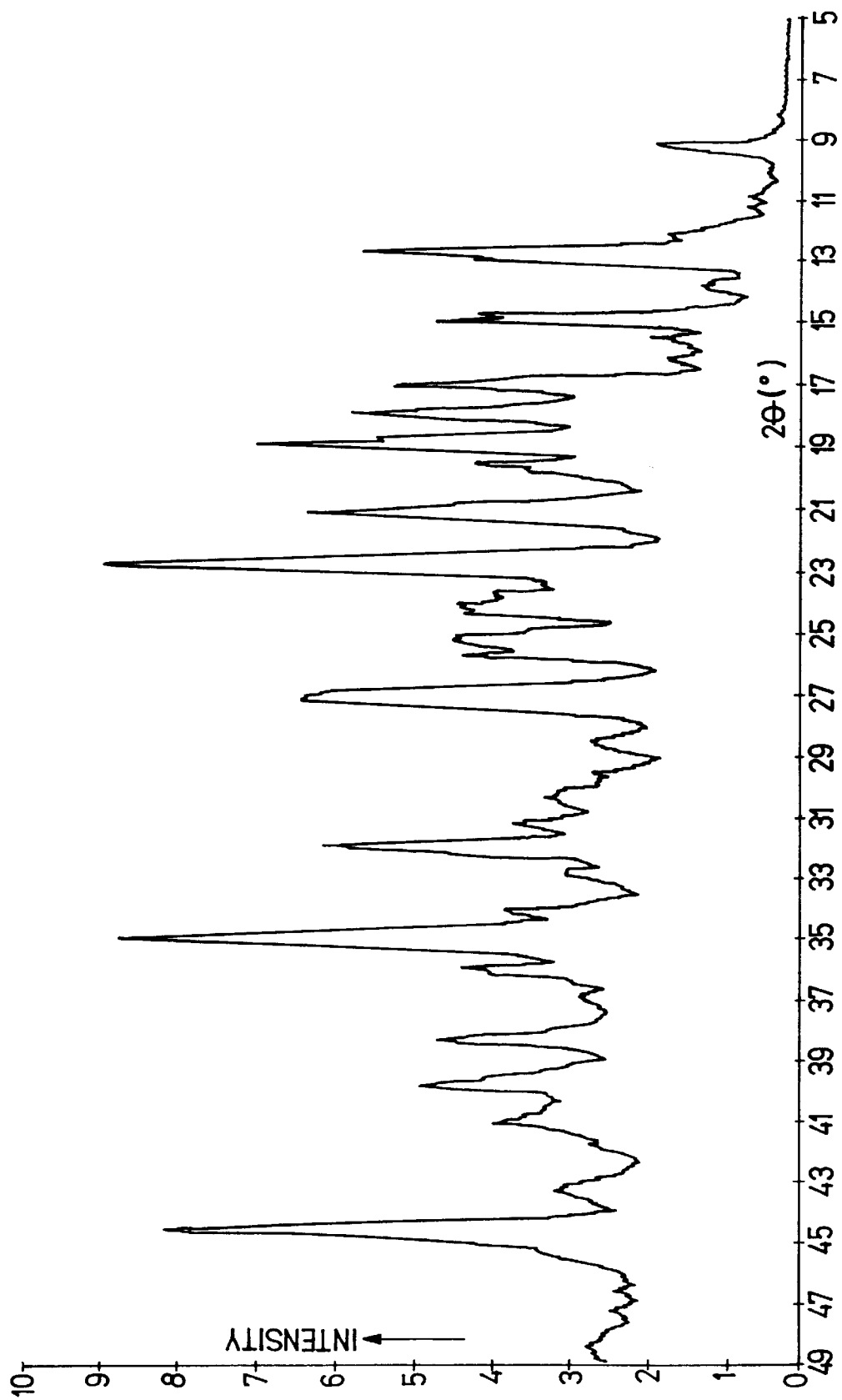
Figure 22D:
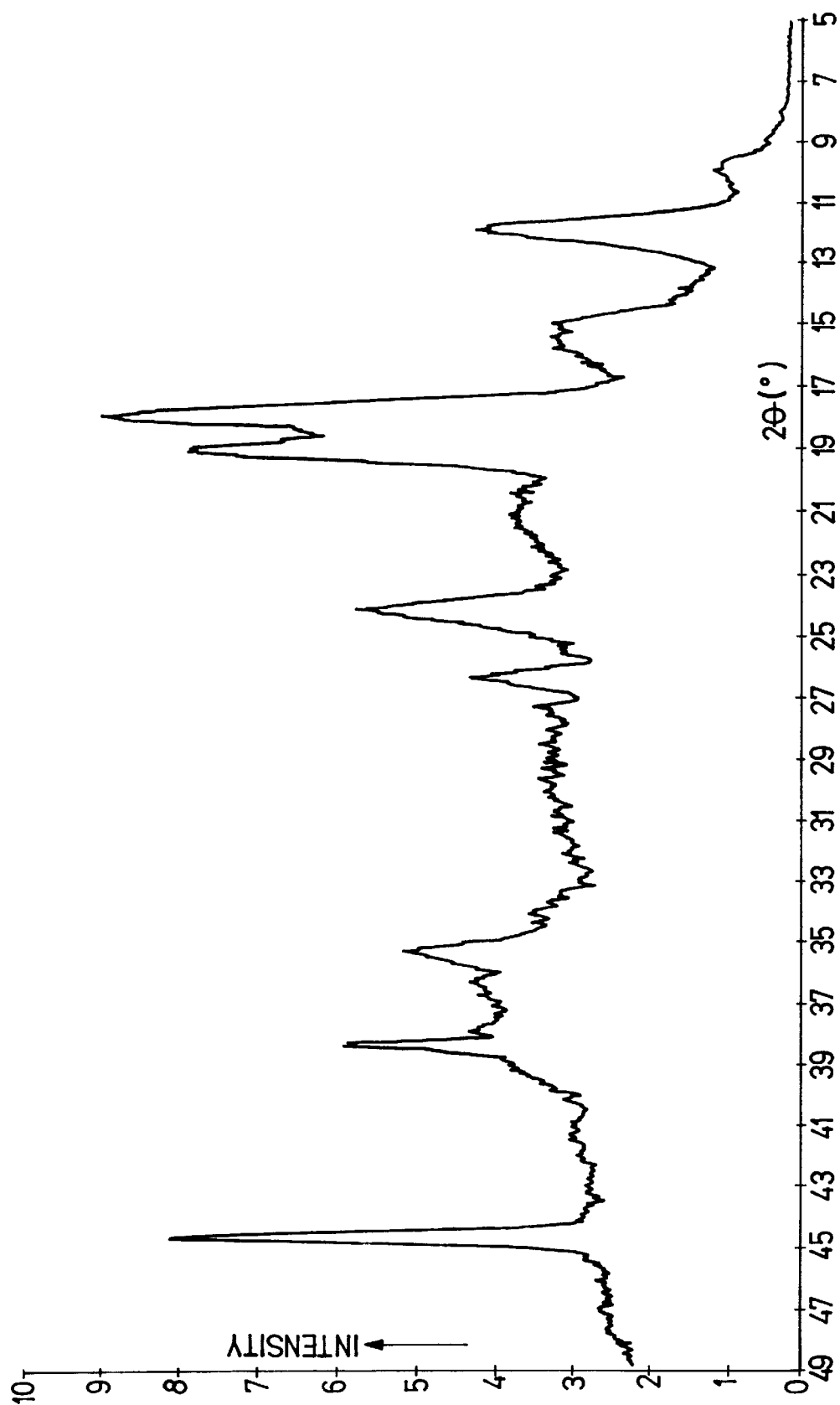

FIGS. 22A to 22D show the comparison of recordings of X-ray powder diffraction for β-cyclodextrin (FIG. 22A), S-(+)-ibuproxam (FIG. 22B), physical mixture of S-(+)-ibuproxam and β-cyclodextrin (FIG. 22C) and inclusion complex of S-(+)-ibuproxam with β-cyclodextrin (FIG. 22D).

Figure 23A:
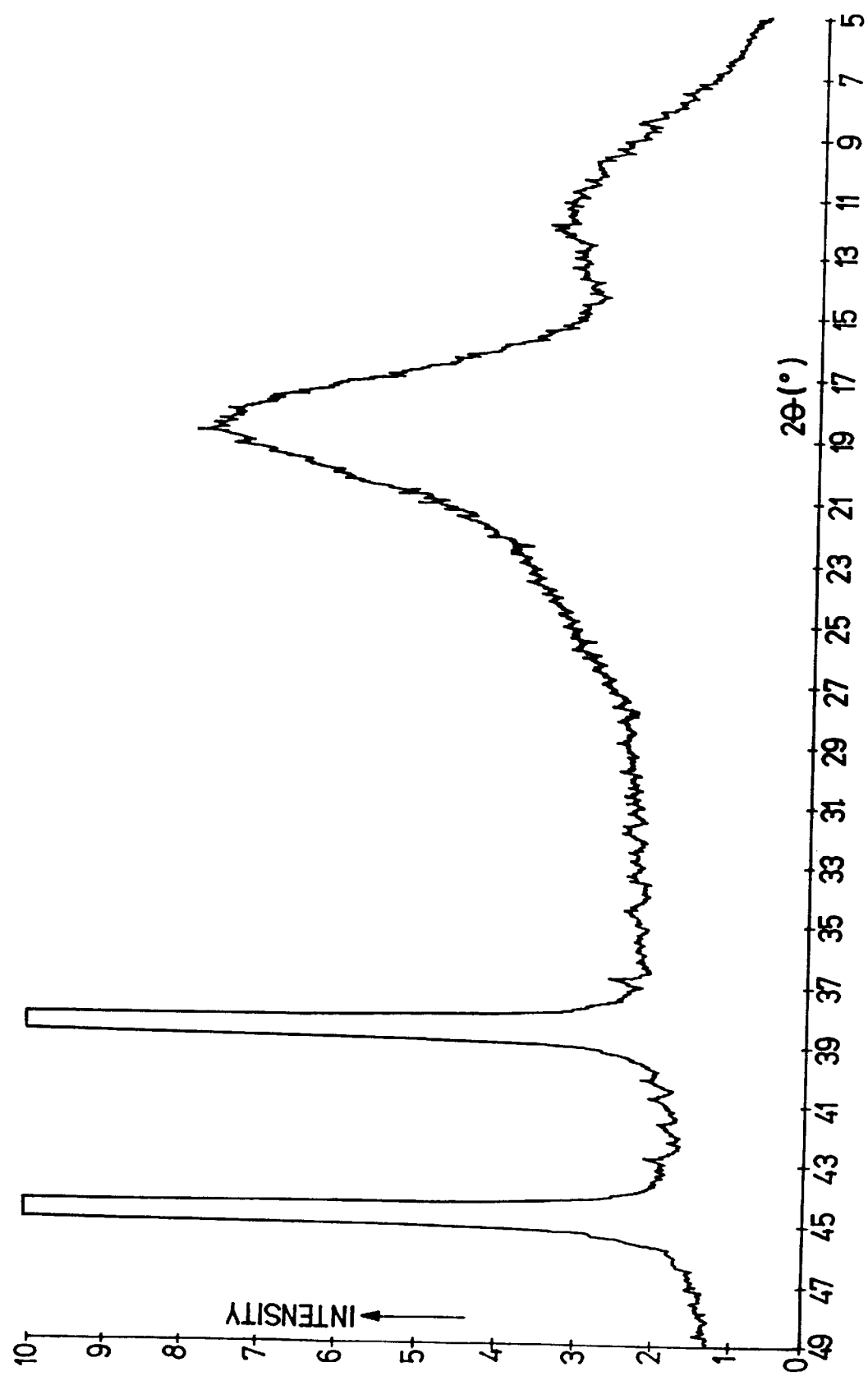
FIGS. 23A to 23D show the comparison of recordings of x-ray powder diffraction for hydroxypropyl-β-cyclodextrin (FIG. 23A), S-(+)-ibuproxam (FIG. 23B), physical mixture of S-(+)-ibuproxam and hydroxypropyl-β-cyclodextrin (FIG. 23C) and inclusion complex of S-(+)-ibuproxam with hydroxypropyl-β-cyclodextrin (FIG. 23D).
Figure 23B:
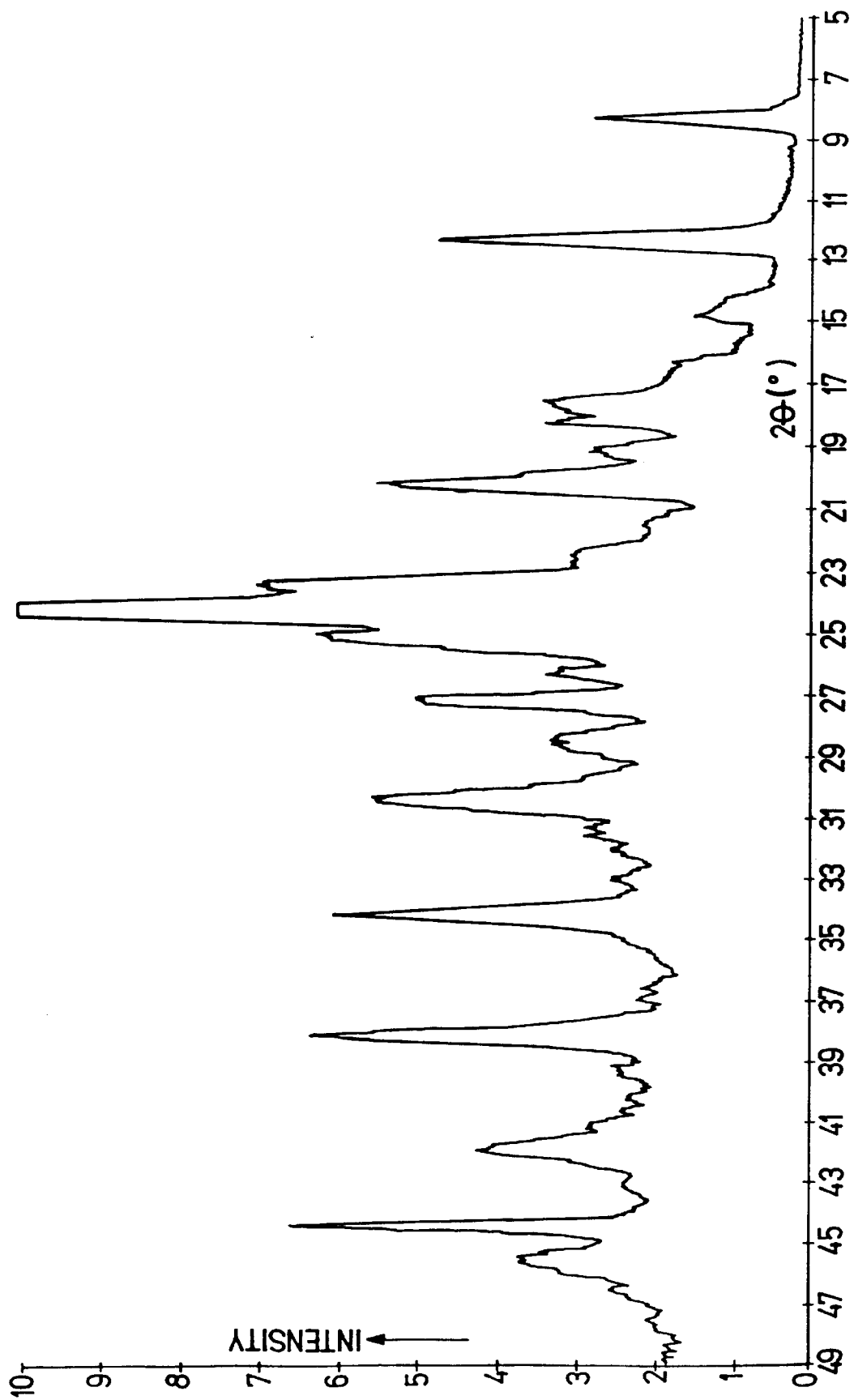
Figure 23C:
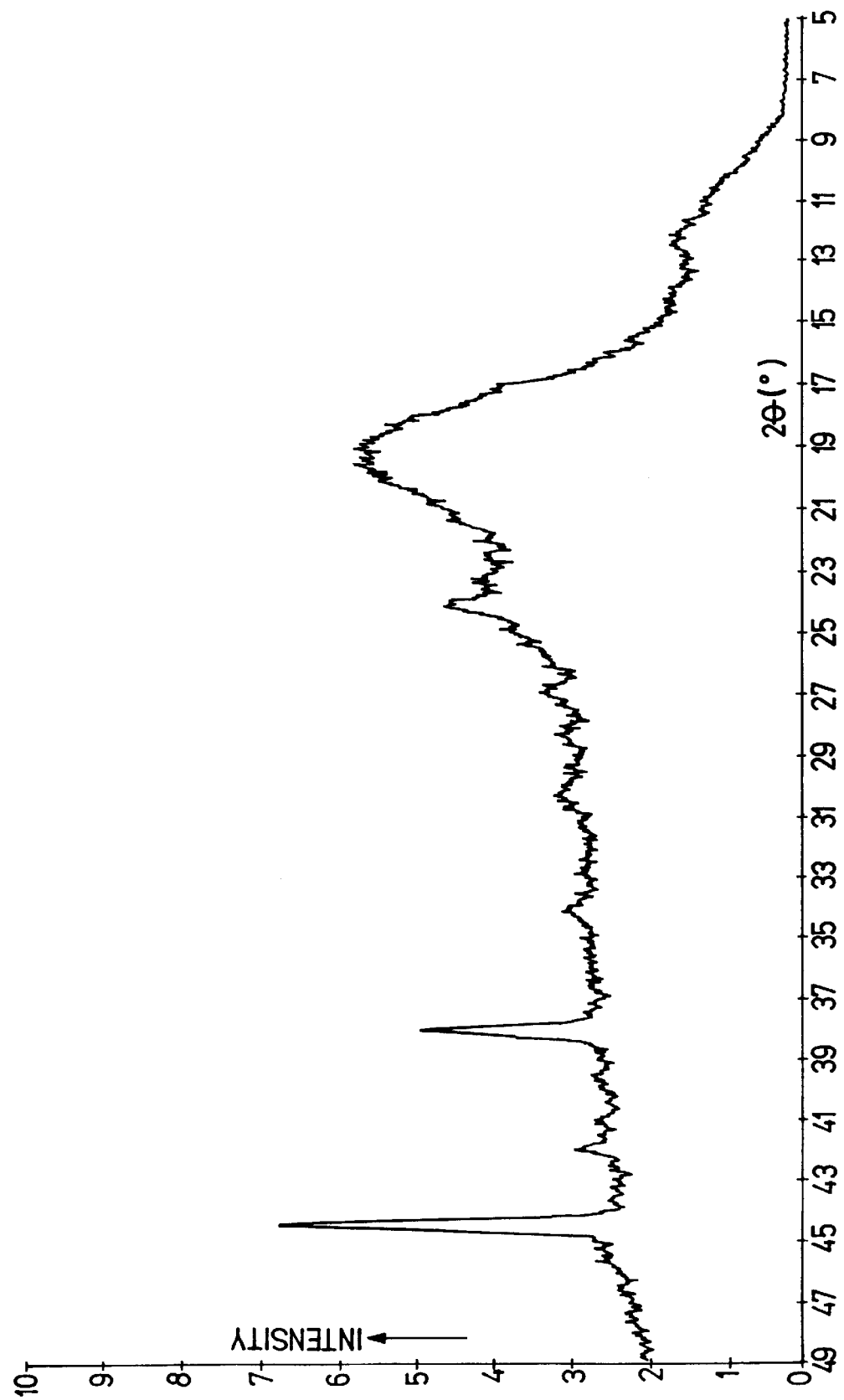
Figure 23D:
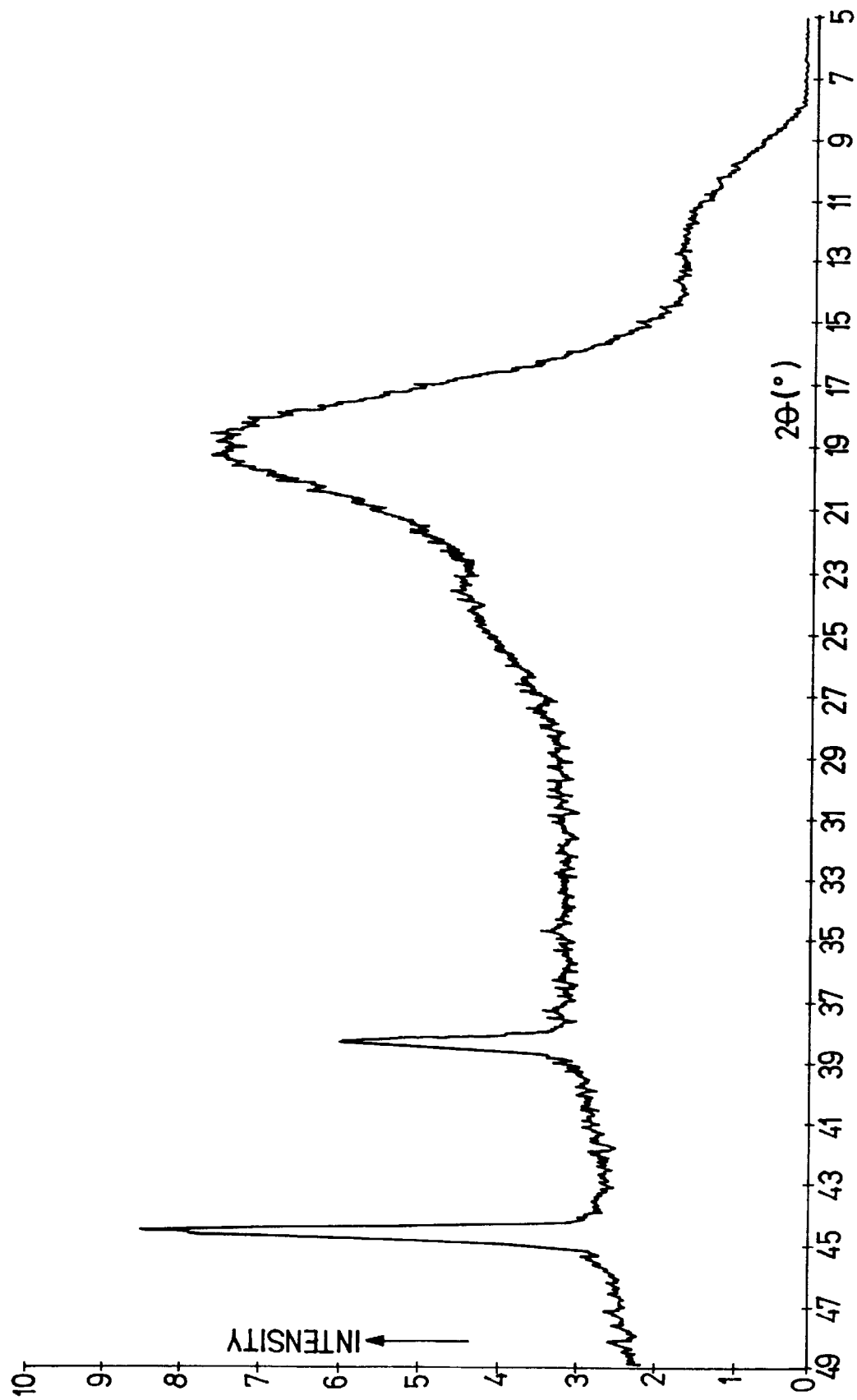

FIGS. 23A to 23D show the comparison of recordings of X-ray powder diffraction for hydroxypropyl-β-cyclodextrin (FIG. 23A), S-(+)-ibuproxam (FIG. 23B), physical mixture of S-(+)-ibuproxam and hydroxypropyl-β-cyclodextrin (FIG. 23C) and inclusion complex of S-(+)-ibuproxam with hydroxypropyl-β-cyclodextrin (FIG. 23D).

Figure 24A:
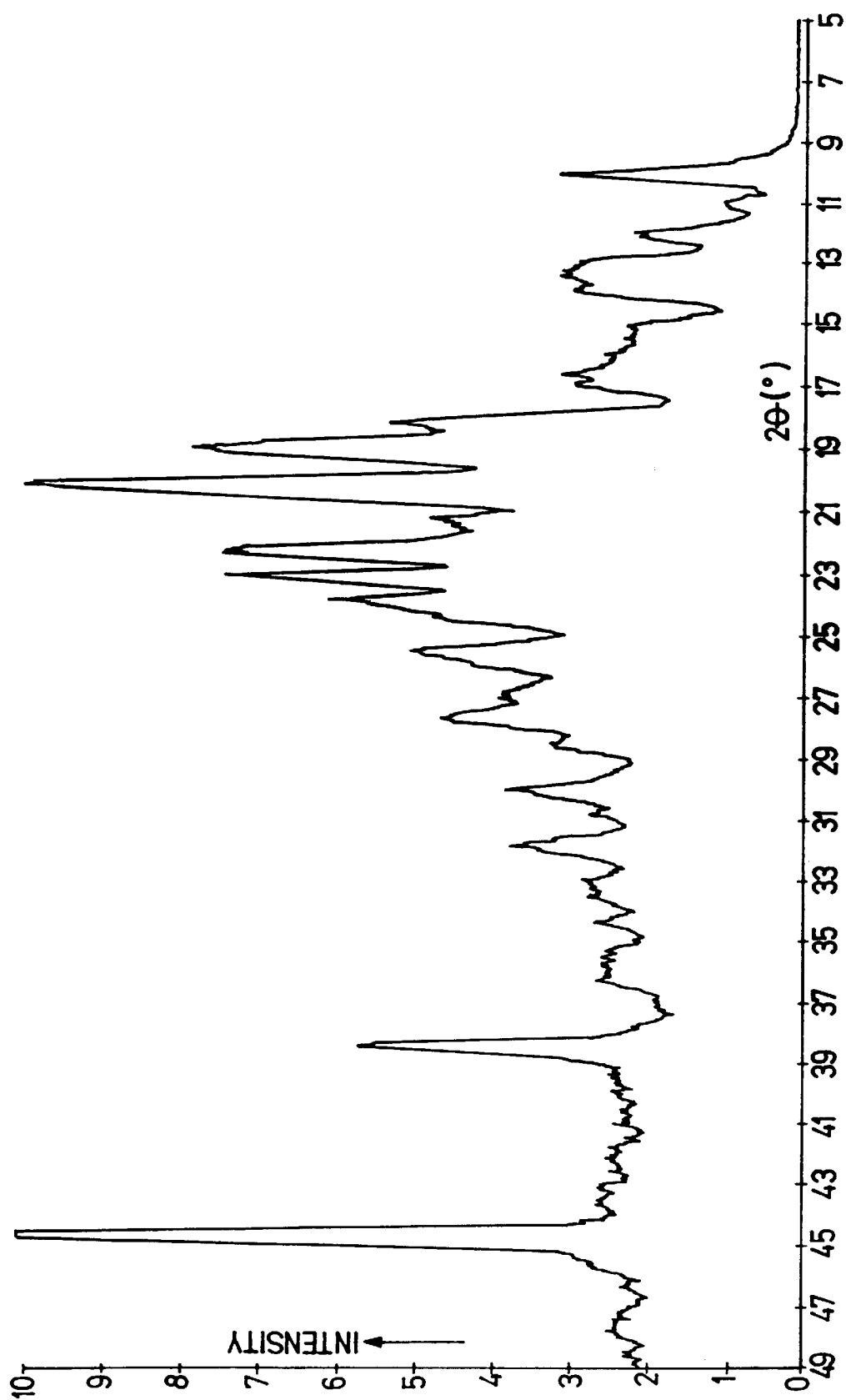
FIGS. 24A to 24D show the comparison of recordings of x-ray powder diffraction for triacetyl-β-cyclodextrin (FIG. 24A), S-(+)-ibuproxam (FIG. 24B), physical mixture of S-(+)-ibuproxam and triacetyl-β-cyclodextrin (FIG. 24C) and inclusion complex of S-(+)-ibuproxam with triacetyl-β-cyclodextrin (FIG. 24D).
Figure 24B:
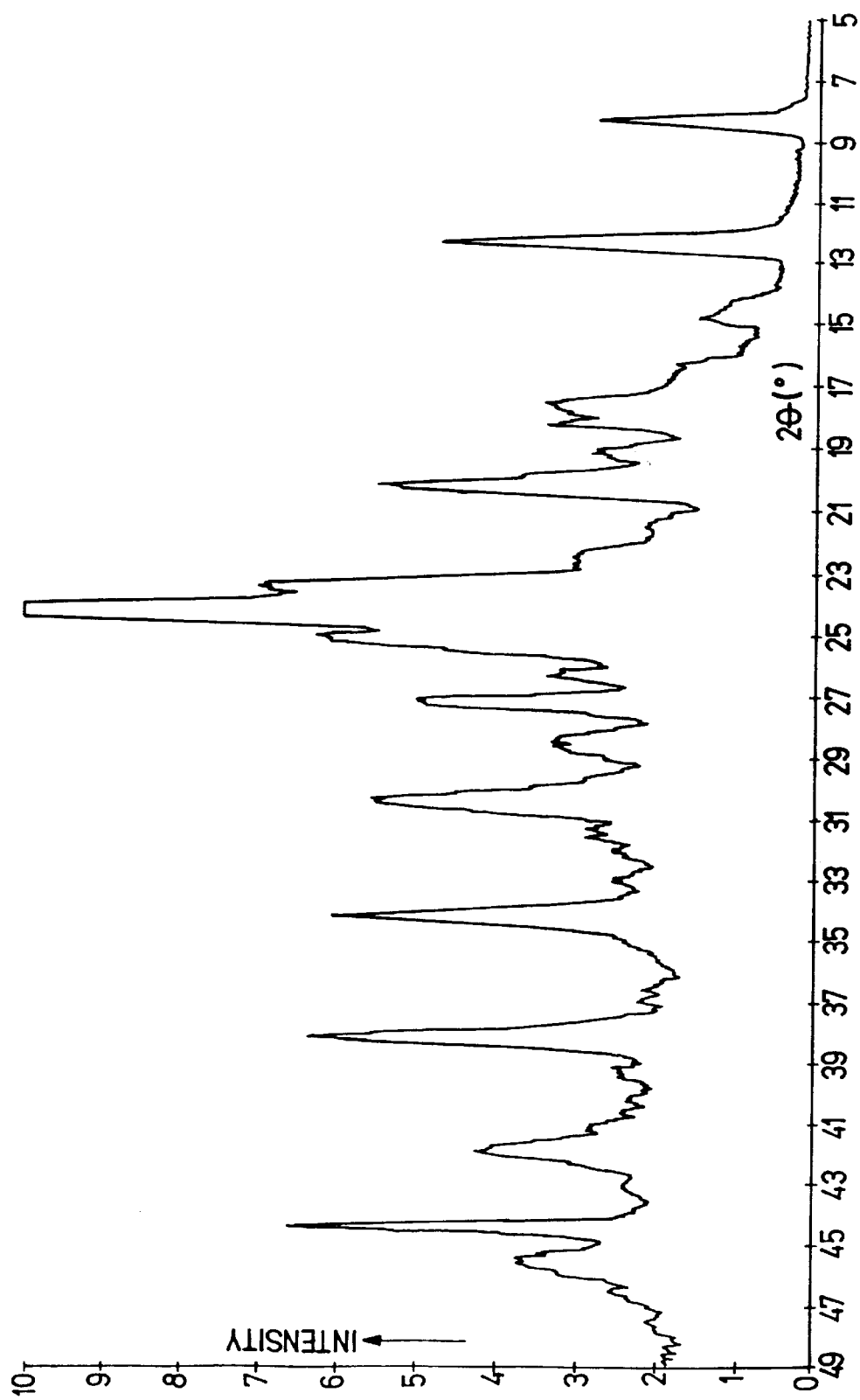
Figure 24C:
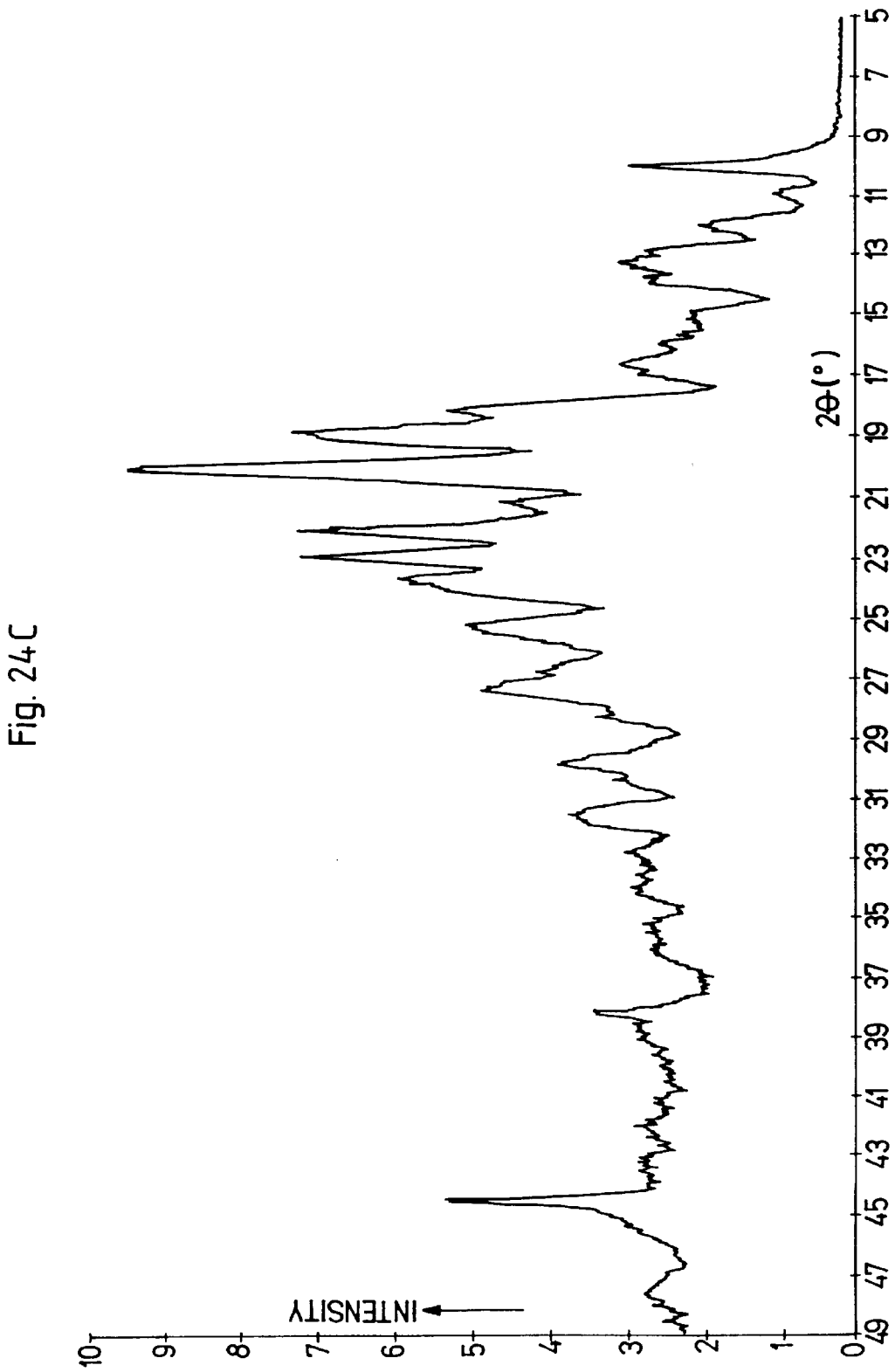
Figure 24D:
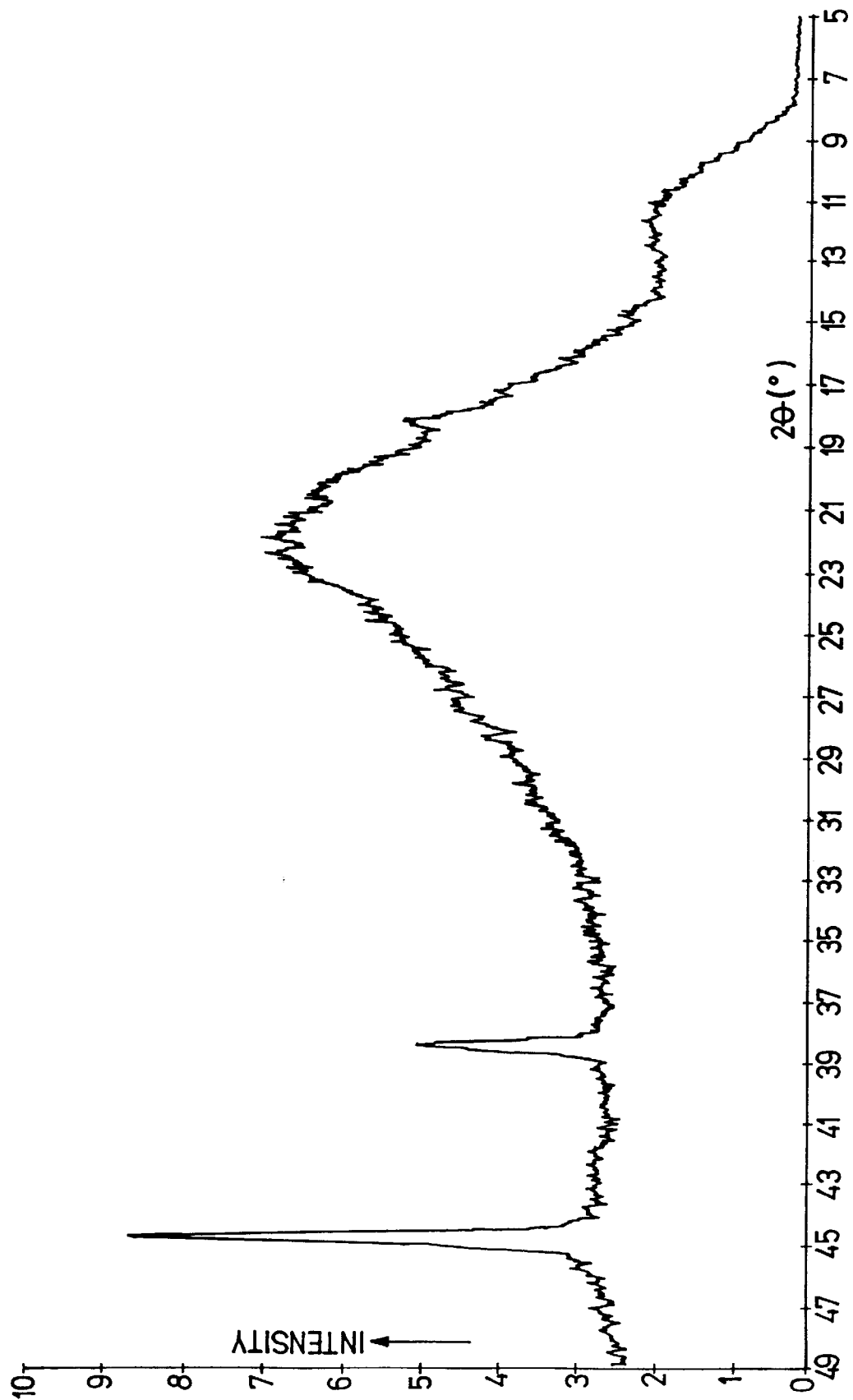

FIGS. 24A to 24D show the comparison of recordings of X-ray powder diffraction for triacetyl-β-cyclodextrin (FIG. 24A), S-(+)-ibuproxam (FIG. 24B), physical mixture of S-(+)-ibuproxam and triacetyl-β-cyclodextrin (FIG. 24C) and inclusion complex of S-(+)-ibuproxam with triacetyl-β-cyclodextrin (FIG. 24D).

Figure 25A:
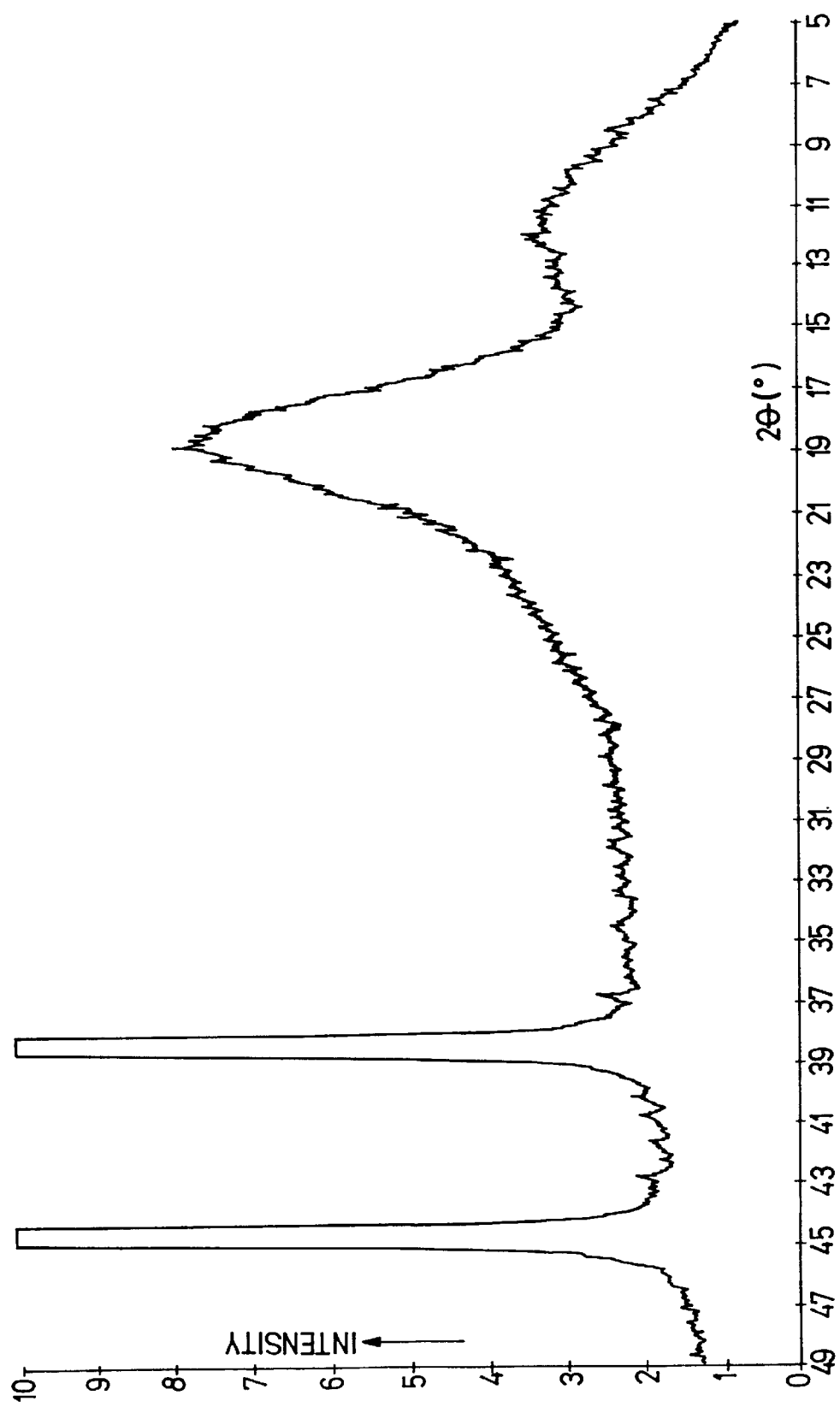
Figure 25B:
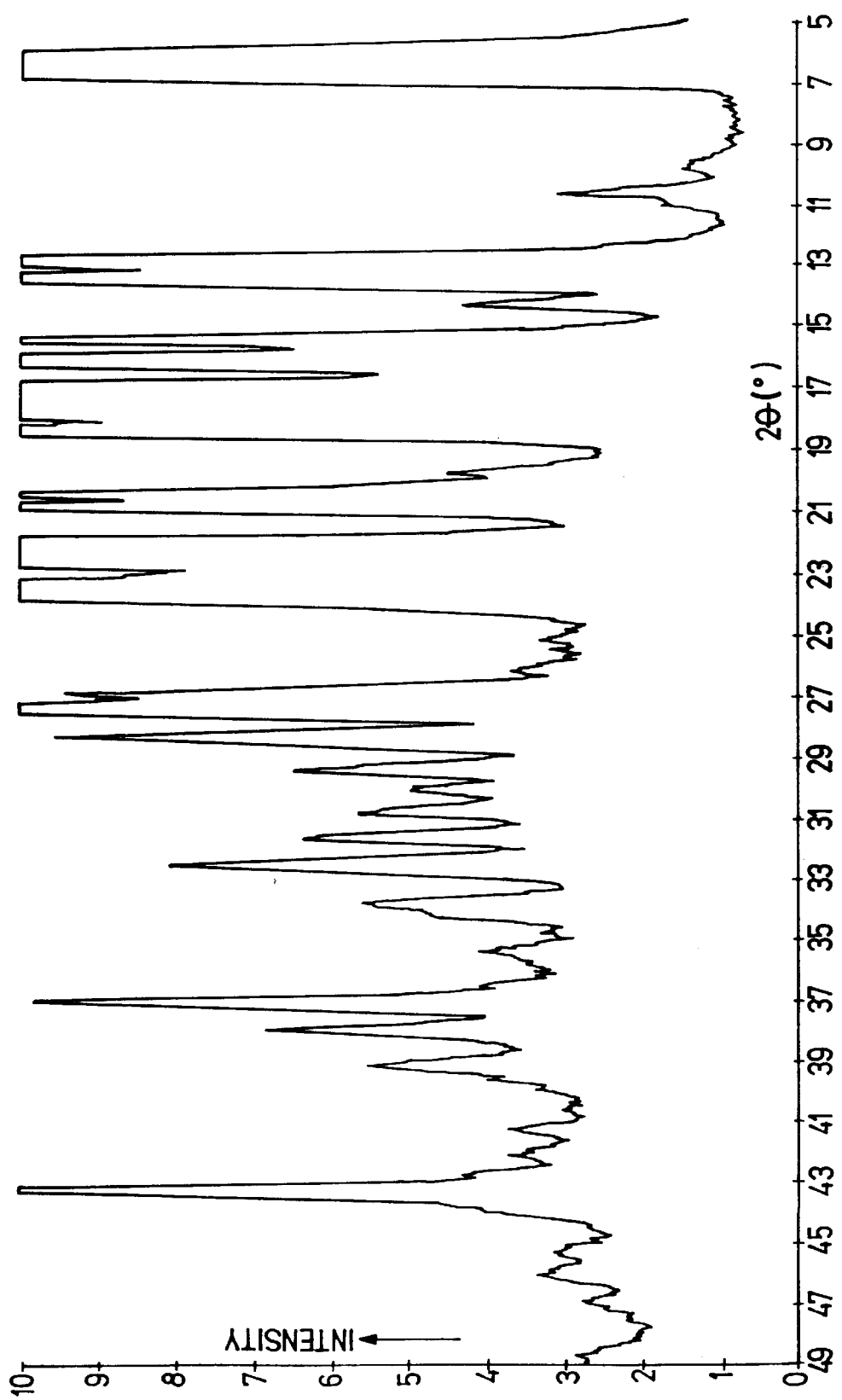
Figure 25C:
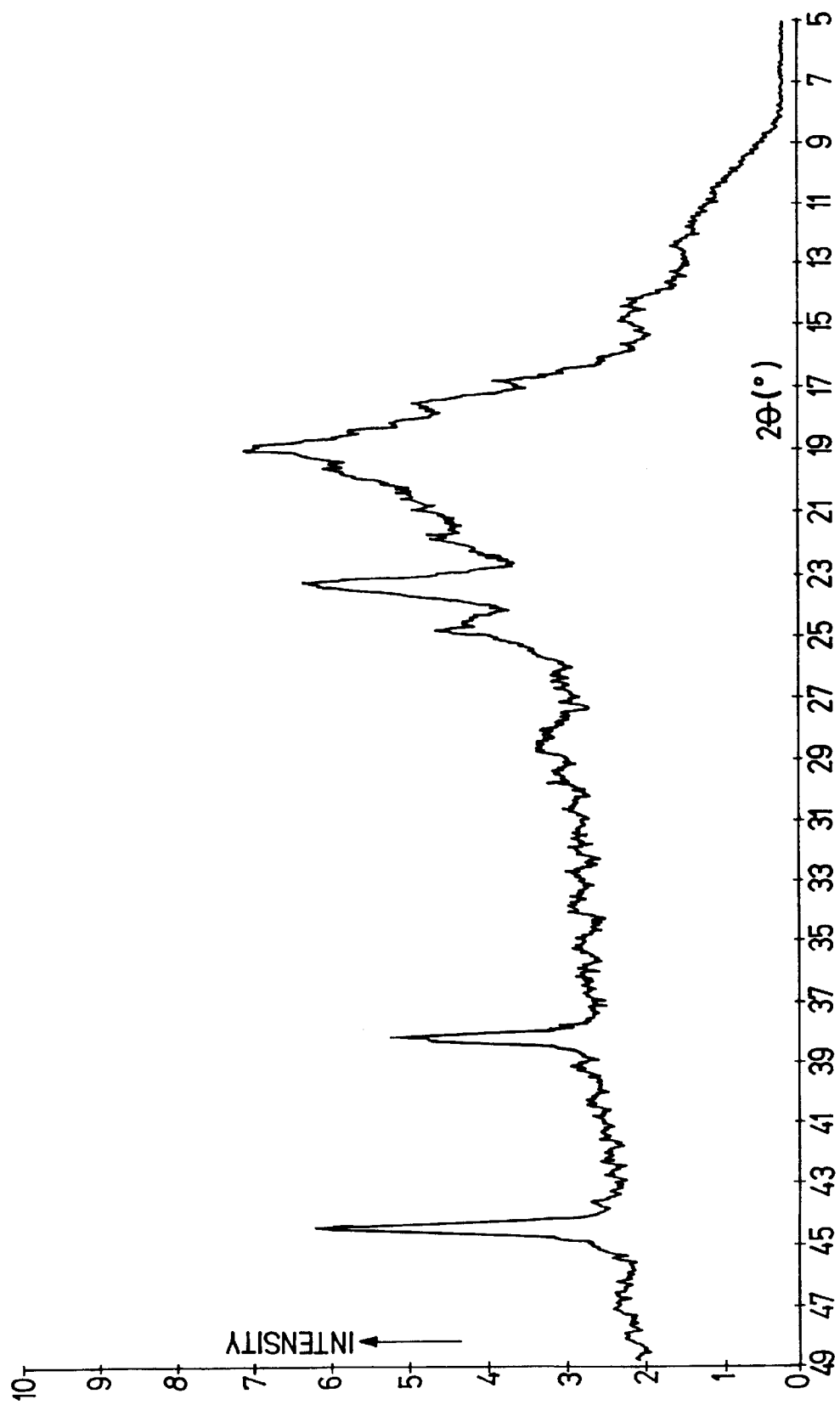

FIGS. 25A to 25D show the comparison of recordings of X-ray powder diffraction for hydroxypropyl-β-cyclodextrin (FIG. 25A), racemic ibuproxam (FIG. 25B), physical mixture of racemic ibuproxam and hydroxypropyl-β-cyclodextrin (FIG. 25C) and inclusion complex of racemic ibuproxam with hydroxypropyl-β-cyclodextrin (FIG. 25D).

Figure 26A:
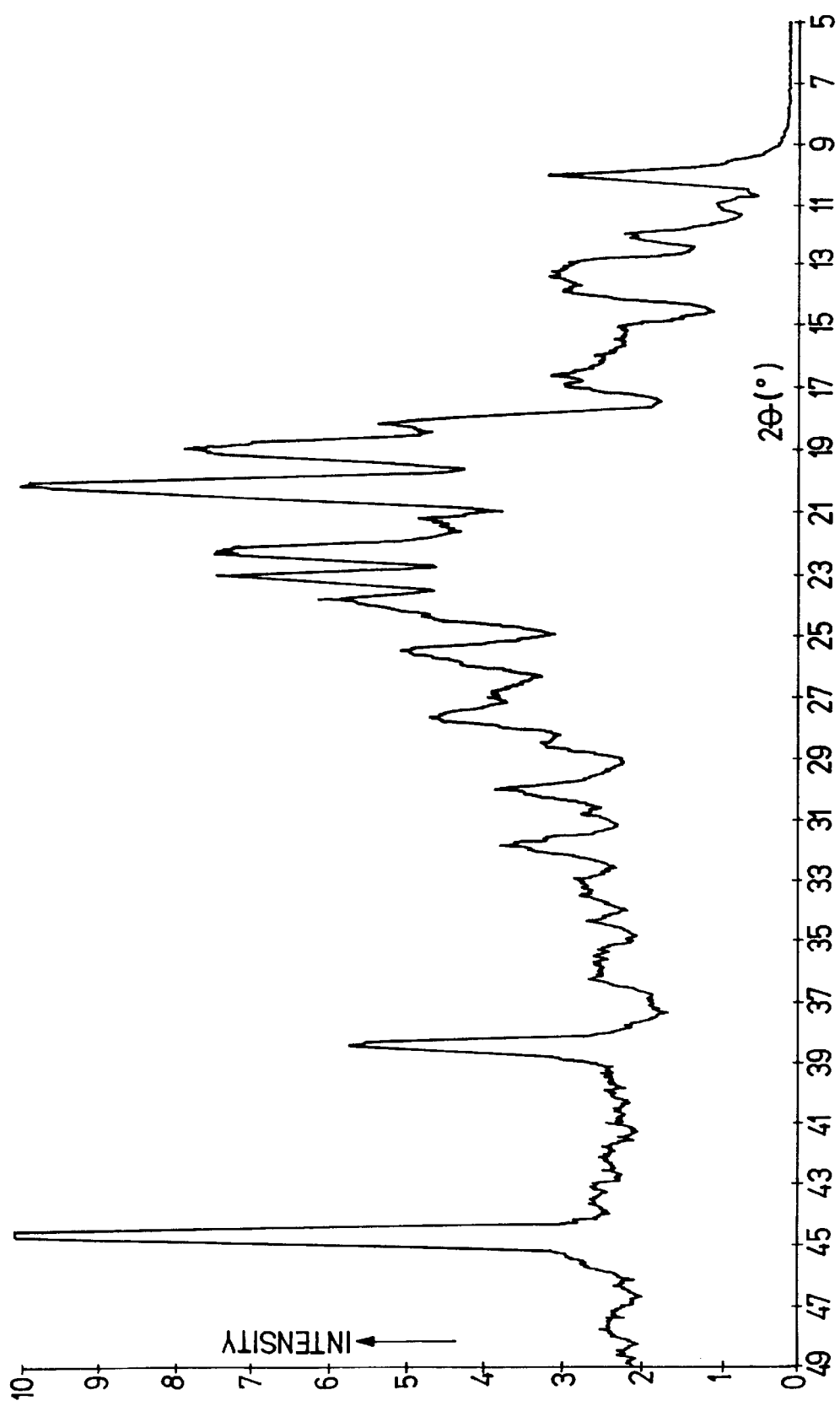
Figure 26B:
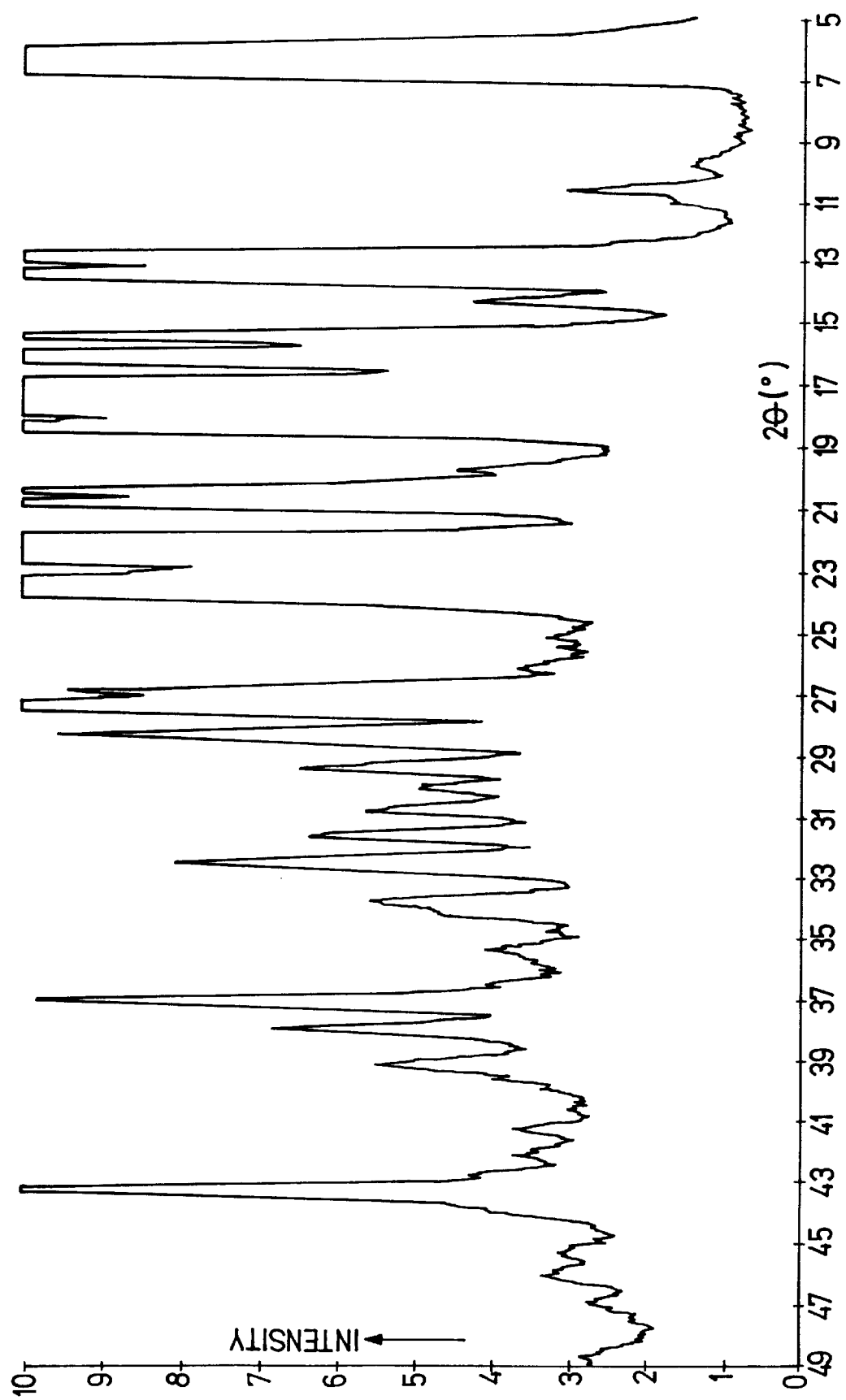
Figure 26C:
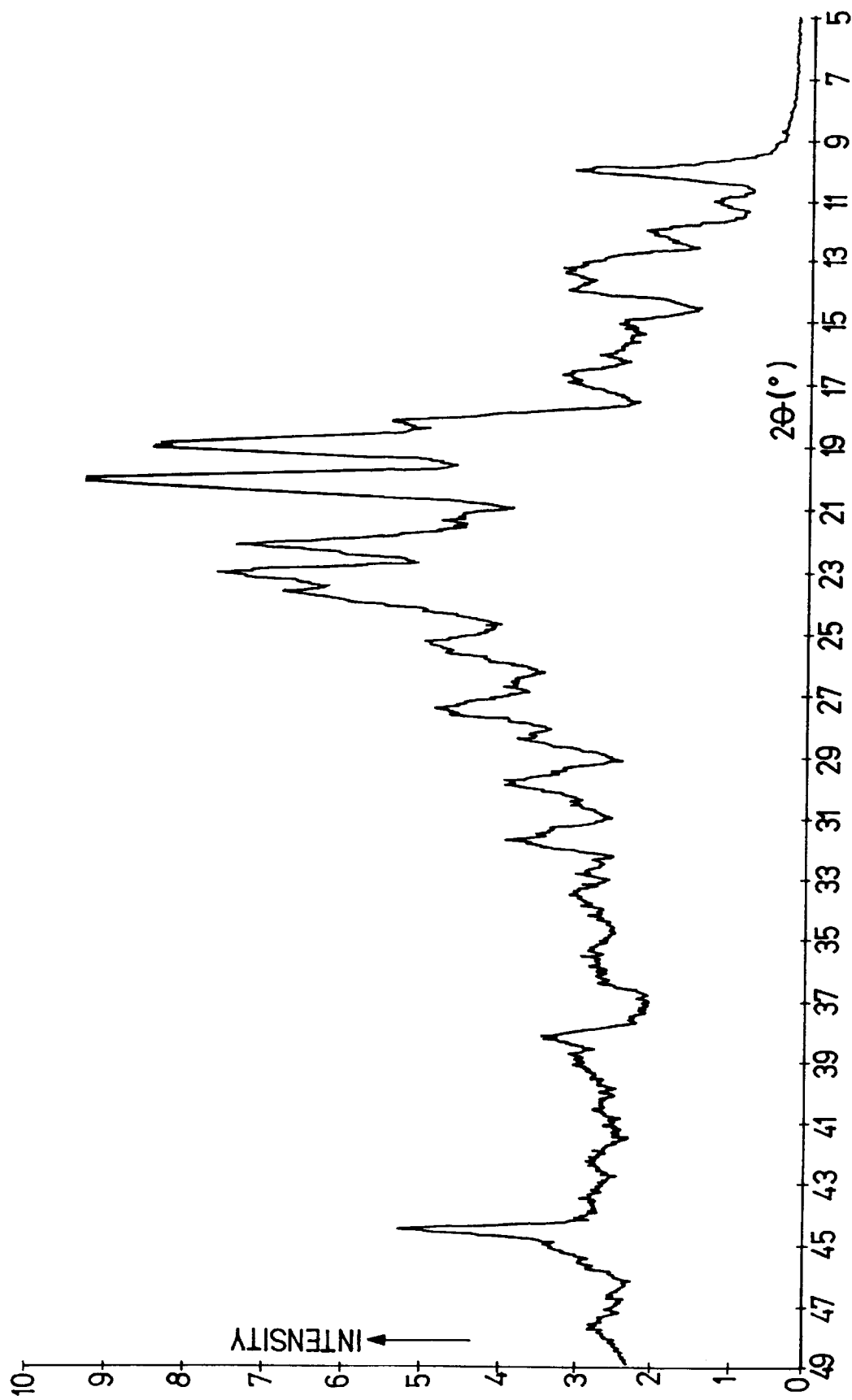

FIGS. 26A to 26D show the comparison of recordings of X-ray powder diffraction for triacetyl-β-cyclodextrin (FIG. 26A), racemic ibuproxam (FIG. 26B), physical mixture of racemic ibuproxam and triacetyl-β-cyclodextrin (FIG. 26C) and inclusion complex of racemic ibuproxam with triacetyl-β-cyclodextrin (FIG. 26D).

EXAMPLE 18

Preparation of tablets with 200 mg of active substance (inclusion complex of S-(+)-ibuproxam with β-cyclodextrin)

Tablets of the following composition were prepared

| | |
| --- | --- |
| inclusion complex of S-(+)-ibuproxam with β-cyclodextrin | 1300.0 mg |
| poliviniylpyrrolidone | 5.0 mg |
| crospovidone (cross-linked polyvinylpyrrolidone) | 96.0 mg |
| colloidal silicon dioxide | 3.2 mg |
| stearic acid | 16.0 mg |
| microcrystalline cellulose | ad 1600.0 mg |

Preparation of tablets

The active substance was homogeneously stirred with additives. The mixture was sieved through a sieve and pressed into tablets on a rotating tableting machine.

EXAMPLE 19

Preparation of dispersion tablets with 200 mg of active substance (inclusion complex of S-(+)-ibuproxam with β-cyclodextrin)

Dispersion tablets of the following composition were prepared

| | |
| --- | --- |
| inclusion complex of S-(+)-ibuproxam with β-cyclodextrin | 1300.0 mg |
| low substituted hydroxypropyl cellulose | 100.0 mg |
| saccharin | 2.0 mg |
| flavours | 10.0 mg |
| coloidal silicon dioxide | 1.6 mg |
| stearic acid | 16.5 mg |
| microcrystalline cellulose | ad 1650.0 mg |

The preparation of dispersion tablets

The active component was homogeneously blended with additives. The mixture was sieved through a sieve and pressed into tablets on a rotating tableting machine. The tablets rapidly disintegrated in water, the obtained suspension had a pleasant taste and was appropriate for consumption.

EXAMPLE 20

Preparation of tablets with 200 mg of active substance (S-(+)-ibuproxam)

Tablets of the following composition were prepared

| | |
| --- | --- |
| S-(+)-ibuproxam | 200.0 mg |
| maize starch | 22.0 mg |
| crospovidone (POLYPLASDONE ® XL | 16.2 mg |
| povidone | 16.2 mg |
| colloidal silicon dioxide (Aerosil 200) | 1.4 mg |
| talcum | 9.7 mg |
| stearic acid | 6.5 mg |
| microcrystalline cellulose | ad 325.0 mg |

Preparation of tablets

The active component was homogeneously stirred with a part of the ingredients (maize starch, crospovidone, microcrystalline cellulose) and granulated with polyvinylpyrrolidone aqueous solution. The obtained granulate was dried, sieved, blended with the remaining amount of the additives (colloidal silicon dioxide, talcum, stearic acid) and pressed into tablets on a rotating tableting machine.

We claim:

1. Inclusion complex selected from the group consisting of including complexes of recemic 2-(4-isobutylphenyl)-propiohydroxamic acid with a cyclodextrin derivative wherein said derivative is selected from the group consisting of dimethyl-β-cyclodextrin, methyl-β-cyclodextrin, trimethyl-β-cyclodextrin, hydroxyethyl-β-cyclodextrin, hydroxypropyl-β-cyclodextrin, glucosyl-β-cyclodextrin, dimaltosyl-β-cyclodextrin, diglucosyl-β-cyclodextrin, succinyl-β-cyclodextrin, triacetyl-β-cyclodextrin, diethyl-β-cyclodextrin, carboxymethylethyl-β-cyclodextrin, dipentyl-β-cyclodextrin, tripentyl-β-cyclodextrin, or acetyldipentyl-β-cyclodextrin; inclusion complexes of optically active S-(+)-2-(4-isobutylphenyl)-propiohydroxamic acid (ibuproxam) of the formula

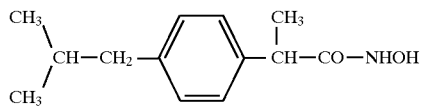

with a cyclodextrin derivative wherein said derivative is selected from the group consisting of dimethyl-β-cyclodextrin, methyl-β-cyclodextrin, trimethyl-β-cyclodextrin, hydroxyethyl-β-cyclodextrin, hydroxypropyl-β-cyclodextrin, glucosyl-β-cyclodextrin, dimaltosyl-β-cyclodextrin, diglucosyl-β-cyclodextrin, succinyl-β-cyclodextrin, triacetyl-β-cyclodextrin, diethyl-β-cyclodextrin, carboxymethylethyl-β-cyclodextrin, dipentyl-β-cyclodextrin, tripentyl-β-cyclodextrin, or acetyldipentyl-β-cyclodextrin; and inclusion complex of said optically active S(+)-2-(4-isobutylphenyl)propiohydroxamic acid with β-cyclodextrin.

2. Inclusion complex according to claim 1, characterized in that the cyclodextrin derivative is selected from methyl-β-cyclodextrin, dimethyl-β-cyclodextrin, hydroxyethyl-β-cyclodextrin, hydroxypropyl-β-cyclodextrin or triacetyl-β-cyclodextrin.

3. Inclusion complex of claim 1 comprising optically active S-(+)-ibuproxam with β-cyclodextrin.

4. Inclusion complex of claim 1 comprising optically active S-(+)-ibuproxam with hydroxyethyl-β-cyclodextrin.

5. Inclusion complex of claim 1 comprising optically active S-(+)-ibuproxam with hydroxypropyl-β-cyclodextrin.

6. Inclusion complex of claim 1 comprising optically active S-(+)-ibuproxam with dimethyl-β-cyclodextrin.

7. Inclusion complex of claim 1 comprising optically active S-(+)-ibuproxam with methyl-β-cyclodextrin.

8. Inclusion complex of claim 1 comprising optically active S-(+)-ibuproxam with triacetyl-β-cyclodextrin.

9. Inclusion complex of claim 1 comprising racemic ibuproxam with hydroxyethyl-β-cyclodextrin.

10. Inclusion complex of claim 1 comprising racemic ibuproxam with hydroxypropyl-β-cyclodextrin.

11. Inclusion complex of claim 1 comprising racemic ibuproxam with dimethyl-β-cyclodextrin.

12. Inclusion complex of claim 1 comprising racemic ibuproxam with methyl-β-cyclodextrin.

13. Inclusion complex of claim 1 comprising racemic ibuproxam with triacetyl-β-cyclodextrin.

14. Inclusion complex according to claim 1, wherein the molar ratio between racemic ibuproxam or optically active S-(+)-ibuproxam and said cyclodextrin derivative or, in the case of optically active S-(+)-ibuproxam, with β-cyclodextrin is 1:5 to 5:1.

15. Inclusion complex according to claim 14, wherein the molar ratio between racemic ibuproxam or optically active S-(+)-ibuproxam and said cyclodextrin derivative or, in the case of optically active S-(+)-ibuproxam, with β-cyclodextrin is to 1:2 to 2:1.

16. Pharmaceutical preparation for the treatment of inflammations and febrile conditions and for alleviating pain, characterized in that it contains a therapeutically active amount which provides an average daily dose of 200 mg/day to 2000 mg/day of an inclusion complex selected from the group consisting of inclusion complex of racemic ibuproxam with a cyclodextrin derivative wherein said derivative is selected from the group consisting of dimethyl-β-cyclodextrin, methyl-β-cyclodextrin, trimethyl-β-cyclodextrin, hydroxyethyl-β-cyclodextrin, hydroxypropyl-β-cyclodextrin, glucosyl-β-cyclodextrin, dimaltosyl-βcyclodextrin, diglucosyl-β-cyclodextrin, succinyl-β-cyclodextrin, triacetyl-βcyclodextrin, diethyl-βcyclodextrin, crboxymethylethyl-βcyclodextrin, dipentyl-β-cyclodextrin, tripentyl-β-cyclodextrin, or acetyldipentyl-β-cyclodextrin; optically active S-(+)-ibuproxam with cyclodextrin derivative wherein said derivative is selected from the group consisting of dimethyl-β-cyclodextrin, methyl-β-cyclodextrin, trimethyl-β-cyclodextrin, hydroxyethyl-βcyclodextrin, hydroxypropyl-β-cyclodextrin, glucosyl-β-cyclodextrin, dimaltosyl-β-cyclodextrin, diglucosyl-β-cyclodextrin, succinyl-β-cyclodextrin, triacetyl-βcyclodextrin, diethyl-β-cyclodextrin, carboxymethylethyl-β-cyclodextrin, dipentyl-β-cyclodextrin, tripentyl-β-cyclodextrin, or acetyldipentyl-β-cyclodextrin and inclusion complex of said optically active S(+)-2-(4-isobutylphenyl)-propiohydroxamic acid with β-cyclodextrin according to claim 1; together with a conventional pharmaceutically acceptable carrier and other adjuvants.

17. Pharmaceutical preparation for the treatment of inflammations and febrile conditions and for alleviating pain, characterized in that it contains a therapeutically active amount which provides an average daily dose of 200 mg/day to 2000 mg/day of inclusion complex of racemic ibuproxam or optically active S-(+)-ibuproxam with β-cyclodextrin derivative selected from hydroxyethyl-β-cyclodextrin, hydroxypropyl-β-cyclodextrin, dimethyl-β-cyclodextrin, methyl-β-cyclodextrin or triacetyl-β-cyclodextrin according to claim 2.

18. Pharmaceutical preparation for the treatment of inflammations and febrile conditions and for alleviating pain, characterized in that it contains a therapeutically active amount which provides an average daily dose of 200 mg/day to 2000 mg/day of inclusion complex of optically active S-(+)-ibuproxam with β-cyclodextrin together with a conventional pharmaceutically acceptable carrier and other adjuvants.

19. A method for treating at least one condition selected from the group consisting of inflammation, febrile condition or pain which comprises administering to a patient suffering from said condition a therapeutically active amount of an inclusion complex of optically active S-(+)-ibuproxam with β-cyclodextrin according to claim 3 with a lower ulcerogenic activity.

20. A method for treating at least one condition selected from the group consisting of inflammation, febrile condition or pain which comprises administering to a patient suffering from said condition a therapeutically active amount of an inclusion complex according to claim 1 with a lower ulcerogenic activity.

21. A method for treating at least one condition selected from the group consisting of inflammation, febrile condition or pain which comprises administering to a patient suffering from said condition a therapeutically active amount of inclusion complex according to claim 2 with a lower ulcerogenic activity.

22. A method for treating at least one condition selected from the group consisting of inflammation, febrile condition or pain which comprises administering to a patient suffering from said condition a therapeutically active amount of optically active S-(+)-ibuproxam.

23. A method for treating at least one condition selected from the group consisting of inflammation, febrile condition or pain which comprises administering to a patient suffering from said condition a therapeutically active amount of an inclusion complex according to claim 14 with a lower ulcerogenic activity.

24. A method for treating at least one condition selected from the group consisting of inflammation, febrile condition or pain which comprises administering to a patient suffering from said condition a therapeutically active amount of an inclusion complex according to claim 15 with a lower ulcerogenic activity.

25. A method for reducing gastric irritations when treating at least one condition selected from the group consisting of inflammation, febrile condition or pain by administering to a patient suffering from said condition a therapeutically active amount of an inclusion complex according to claim 1.

26. A method for reducing gastric irritations when treating at least one condition selected from the group consisting of inflammation, febrile condition or pain by administering to a patient suffering from said condition a therapeutically active amount of an inclusion complex according to claim 2.

27. A method for reducing gastric irritations when treating at least one condition selected from the group consisting of inflammation, febrile condition or pain by administering to a patient suffering from said condition a therapeutically active amount of an inclusion complex of optically active S-(+)-ibuproxam with β-cyclodextrin according to claim 3.

28. A method for reducing gastric irritations when treating at least one condition selected from the group consisting of inflammation, febrile condition or pain by administering to a patient suffering from said condition a therapeutically active amount of an inclusion complex according to claim 14.

29. A method for reducing gastric irritations when treating at least one condition selected from the group consisting of inflammation, febrile condition or pain by administering to a patient suffering from said condition a therapeutically active amount of an inclusion complex according to claim 15.

\* \* \* \* \*